(12) United States Patent
Lee et al.

(10) Patent No.: US 11,471,634 B1
(45) Date of Patent: Oct. 18, 2022

(54) ORO-PILLOW CUSHION ASSEMBLY

(71) Applicant: ResMed Pty Ltd, Bella Vista (AU)

(72) Inventors: Deng Siong Lee, Singapore (SG); Robin Yew, Singapore (SG); Han Seong Chew, Singapore (SG); Teong Hong Chuah, Singapore (SG); Shannon Day, Sydney (AU); Christopher Daniel Parker, Sydney (AU); Vinay Manjunath, Sydney (AU); Nigel Paul Greig, Sydney (AU); Albert Jack Greenwood Woffenden, Sydney (AU); Chuan Foong Lee, Kulaijaya (MY); Muhammad Adil Bin Abdul Halim, Singapore (SG); Andrew William Gillett, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/550,168

(22) Filed: Dec. 14, 2021

(51) Int. Cl.
*A61M 16/06* (2006.01)

(52) U.S. Cl.
CPC .... *A61M 16/0622* (2014.02); *A61M 16/0627* (2014.02); *A61M 16/0672* (2014.02)

(58) Field of Classification Search
CPC .............. A61M 16/06; A61M 16/0616; A61M 16/0622; A61M 16/0627; A61M 16/0666; A61M 16/0672; A61M 2016/0661
See application file for complete search history.

(56) References Cited

U.S. PATENT DOCUMENTS

| 4,782,832 A | 11/1988 | Trimble et al. |
| 4,944,310 A | 7/1990 | Sullivan |
| 6,532,959 B1 | 3/2003 | Berthon-Jones |
| 6,581,594 B1 | 6/2003 | Drew et al. |
| 7,866,944 B2 | 1/2011 | Kenyon et al. |

(Continued)

FOREIGN PATENT DOCUMENTS

| WO | WO 98/004310 A1 | 2/1998 |
| WO | WO 98/034665 A1 | 8/1998 |

(Continued)

OTHER PUBLICATIONS

"Respiratory Physiology", by John B. West, Lippincott Williams & Wilkins, $9^{th}$ edition published 2012 (8 pages).

*Primary Examiner* — Justine R Yu
*Assistant Examiner* — Matthew D Ziegler
(74) *Attorney, Agent, or Firm* — Nixon & Vanderhye P.C.

(57) ABSTRACT

A patient interface including a seal-forming structure having a mouth portion that forms at least part of the mouth plenum and is configured to seal around the patient's mouth and a nasal portion that is configured to seal with the patient's nares. The nasal portion includes a nasal plenum positioned to receive pressurized gas from the mouth plenum. The seal-forming structure also includes a clip configured to connect the mouth plenum to the nasal plenum and act as a conduit for the flow of the pressurized gas from the mouth plenum to the nasal plenum. The clip includes a mouth portion end configured to engage the mouth portion, a nasal portion end configured to engage the nasal portion, and a pair of wings protruding from the nasal portion end into an interior of the nasal plenum so that the wings engage an interior surface of the nasal plenum.

29 Claims, 43 Drawing Sheets

(56) References Cited

U.S. PATENT DOCUMENTS

| | | |
|---|---|---|
| 8,528,558 B2 | 9/2013 | Drew et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,826,910 B2 | 9/2014 | Kwok et al. |
| 9,038,635 B2 * | 5/2015 | Brambilla ................ A61B 5/03 128/207.18 |
| 9,427,544 B2 * | 8/2016 | Frater ................ A61M 16/0666 |
| 10,543,333 B2 | 1/2020 | Ng et al. |
| 10,744,289 B2 | 8/2020 | Lynch et al. |
| 10,744,290 B2 | 8/2020 | Formica et al. |
| 10,806,886 B2 | 10/2020 | Davidson et al. |
| 11,007,337 B2 | 5/2021 | Burnham et al. |
| 11,052,211 B2 | 7/2021 | Ng et al. |
| 11,147,940 B2 | 10/2021 | Dantanarayana et al. |
| 11,160,944 B2 | 11/2021 | Chow et al. |
| 2004/0118406 A1 * | 6/2004 | Lithgow ................ A61M 16/08 128/206.26 |
| 2009/0032026 A1 * | 2/2009 | Price ................ A61M 16/06 128/207.11 |
| 2009/0044808 A1 | 2/2009 | Guney et al. |
| 2009/0050156 A1 | 2/2009 | Ng et al. |
| 2010/0000534 A1 | 1/2010 | Kooij et al. |
| 2013/0199537 A1 * | 8/2013 | Formica ............ A61M 16/0616 128/205.25 |
| 2016/0082214 A1 * | 3/2016 | Barlow .............. A61M 16/0611 128/206.24 |
| 2017/0028153 A1 | 2/2017 | Judson et al. |
| 2018/0078726 A1 * | 3/2018 | Barraclough ..... A61M 16/0495 |
| 2020/0197649 A1 | 6/2020 | Haibach |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | 2014/045245 A1 | 3/2014 |
| WO | 2018/007966 A1 | 1/2018 |
| WO | WO 2020/208523 A1 | 10/2020 |

* cited by examiner

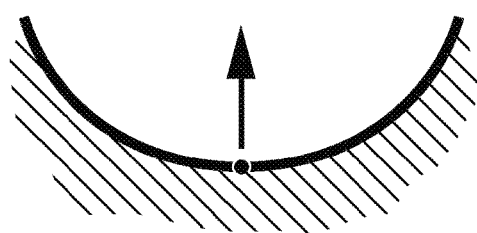
FIG. 3B — Relatively Large Positive Curvature
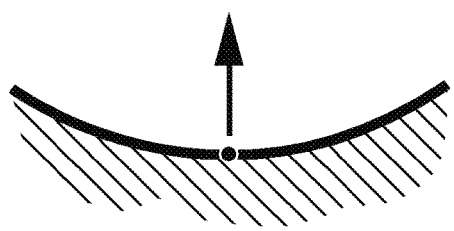
FIG. 3C — Relatively Small Positive Curvature
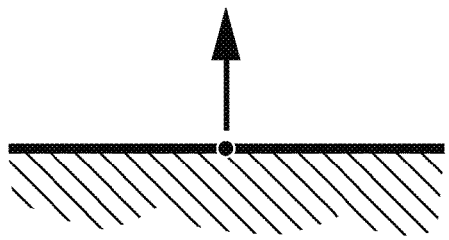
FIG. 3D — Zero Curvature
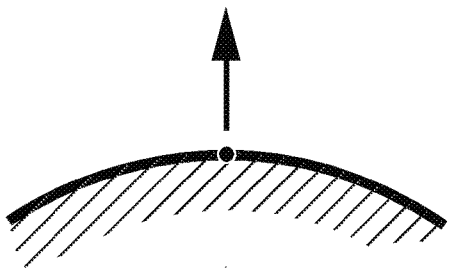
FIG. 3E — Relatively Small Negative Curvature
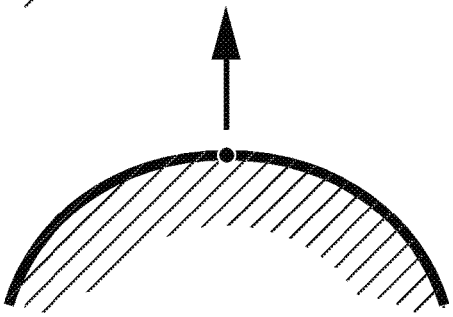
FIG. 3F — Relatively Large Negative Curvature
Copyright 2015 ResMed Limited

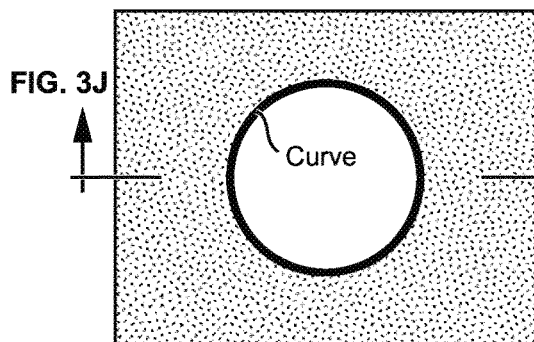
FIG. 3I
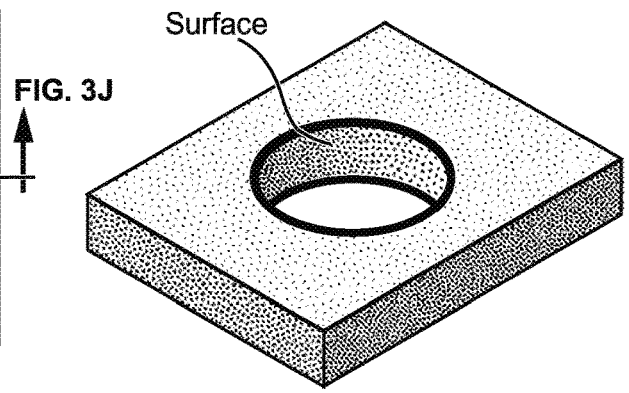
FIG. 3K
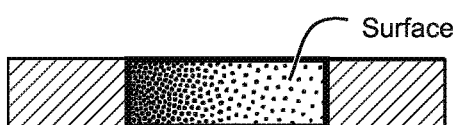
FIG. 3J
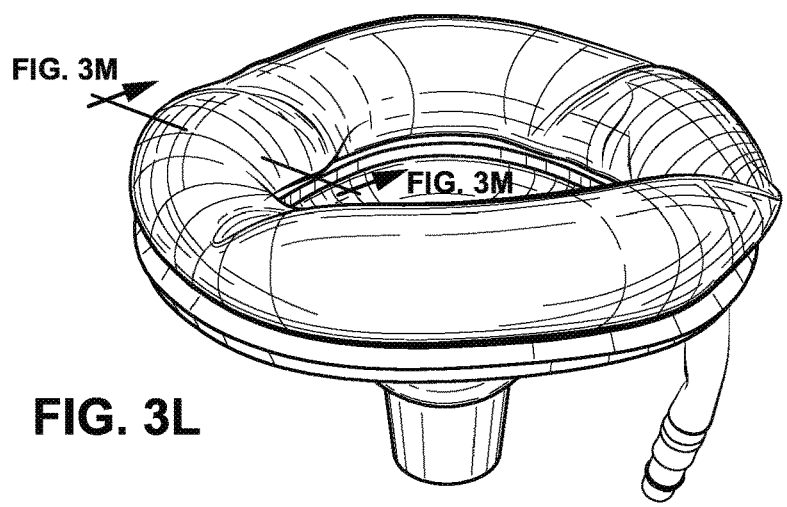
FIG. 3L
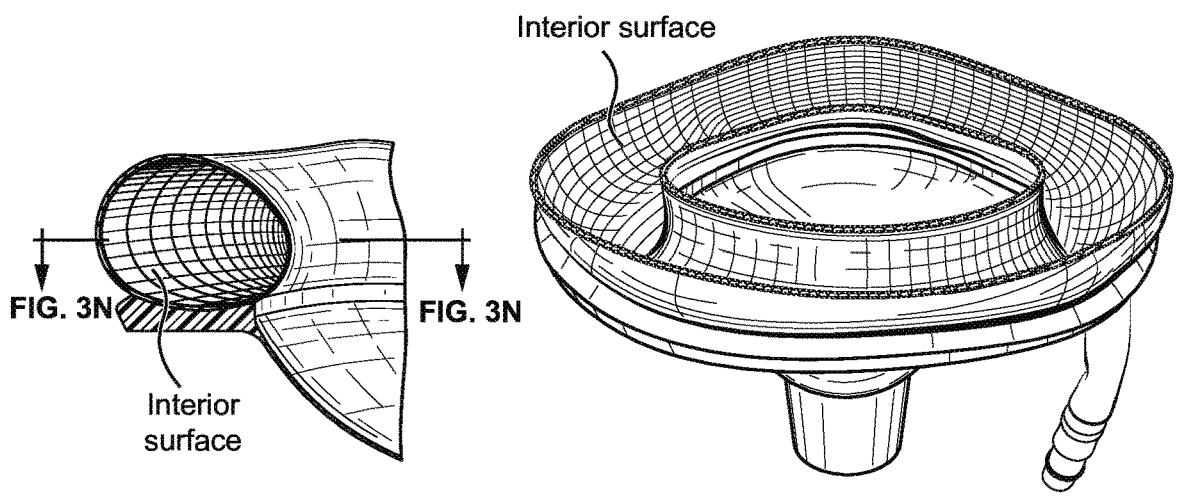
FIG. 3M      FIG. 3N
Copyright 2015 ResMed Limited

Left-hand rule

Right-hand rule

Left ear helix

Right-hand helix
Right-hand positive

Right ear helix

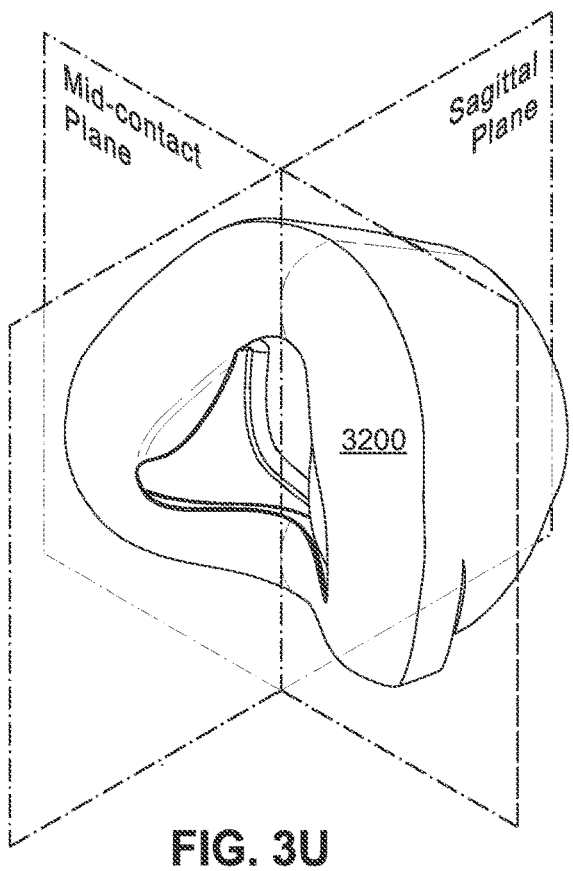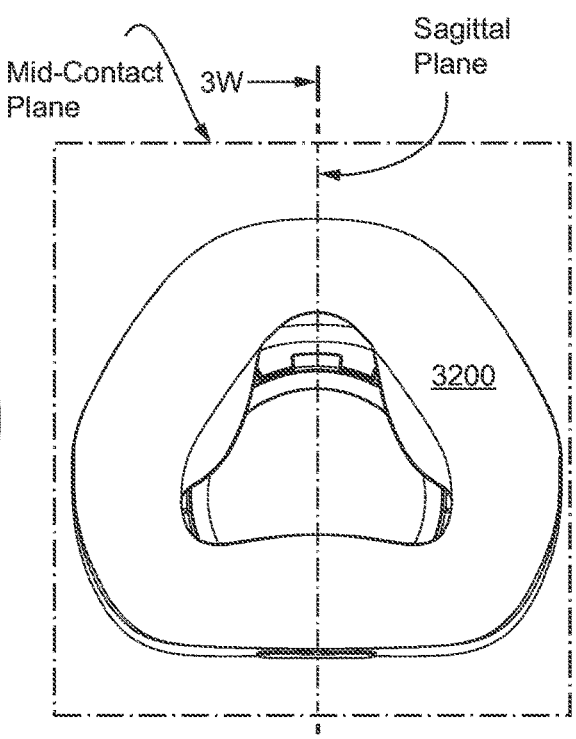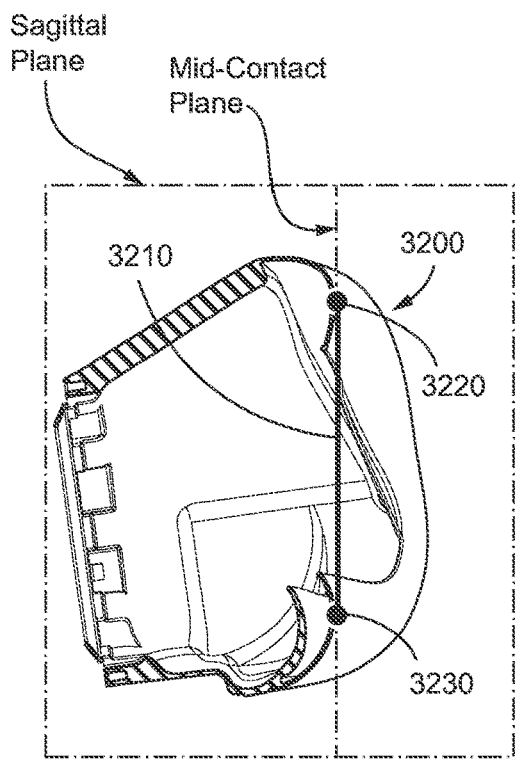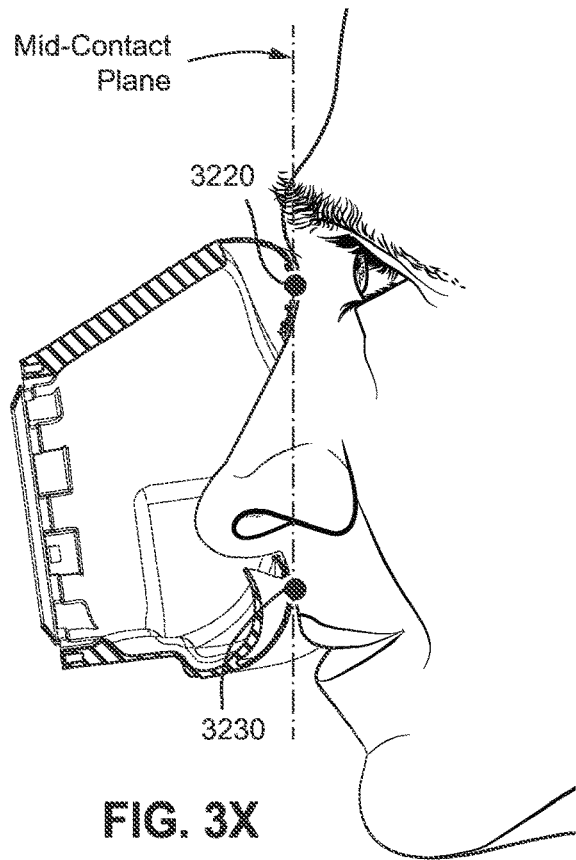
FIG. 3U
FIG. 3V
FIG. 3W
FIG. 3X

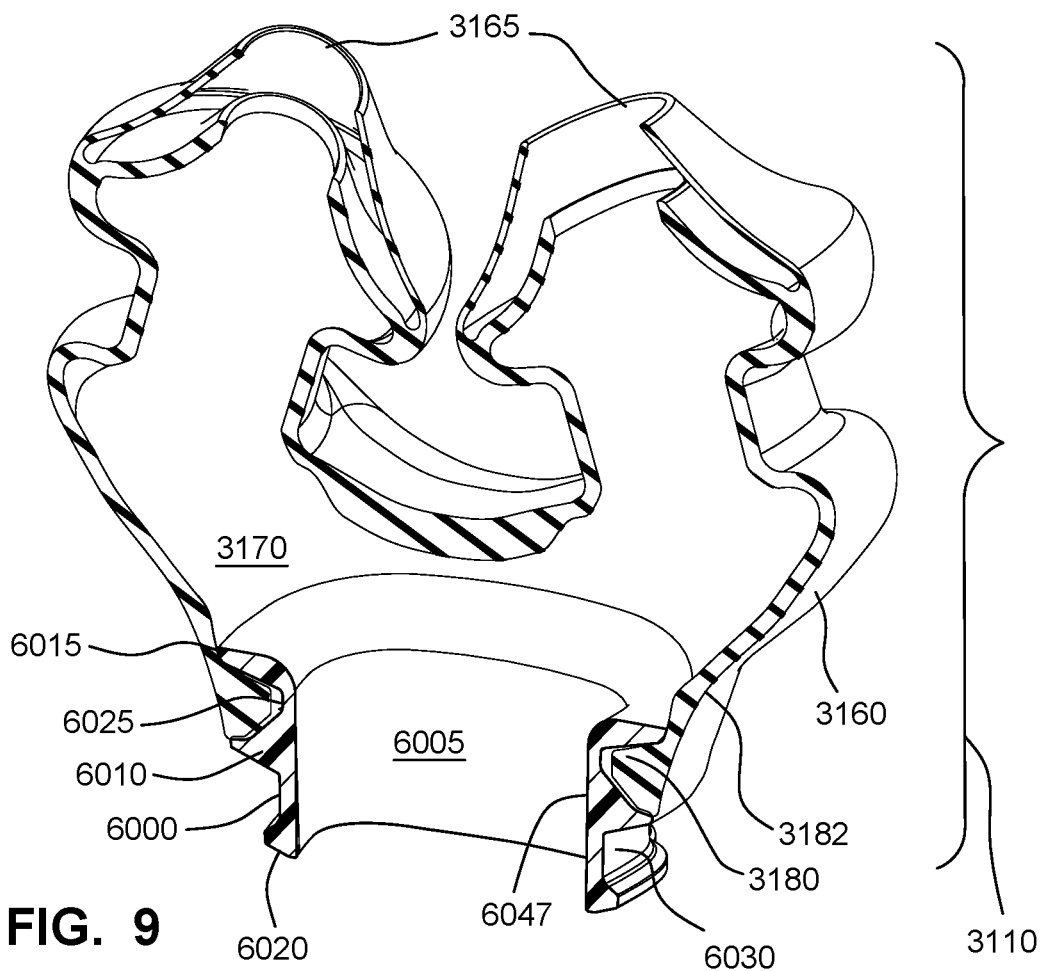
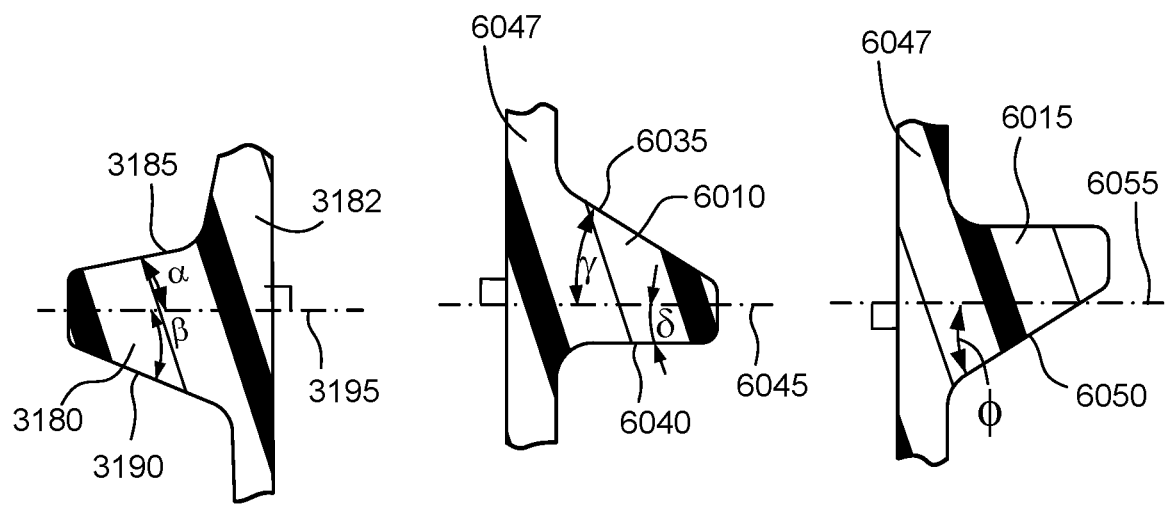
FIG. 9   FIG. 9A   FIG. 9B   FIG. 9C

ORO-PILLOW CUSHION ASSEMBLY

1 BACKGROUND OF THE TECHNOLOGY

1.1 Field of the Technology

The present technology relates to one or more of the screening, diagnosis, monitoring, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

1.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

1.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube or endotracheal tube. In some forms, the comfort and effectiveness of these therapies may be improved.

1.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that may be held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

1.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 98/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

1.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

1.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

1.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

Table of noise of prior masks (ISO 17510-2:2007, 10 cmH2O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO 3744 in CPAP mode at 10 cmH2O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises patient interface with a sealing portion configured to seal against a patient's face.

Another aspect of the present technology comprises a mouth cushion configured to seal around a patient's mouth and a nasal cushion configured to seal around a patient's nares.

Another aspect of the present technology comprises a mouth cushion configured to seal around a patient's mouth and a nasal cushion configured to seal against an interior of the patient's nostrils.

Another aspect of the present technology comprises a nasal cushion configured to seal a patient's nasal airways.

Another aspect of the present technology comprises headgear comprising an air delivery conduit configured to support a patient interface on a patient's head.

Another aspect of the technology comprises a vent for a patient interface that includes a surface with at least one vent hole in the surface.

An aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a mouth portion that forms at least part of the mouth plenum and is configured to seal around the patient's mouth; a nasal portion that is configured to seal with the patient's nares, the nasal portion comprising a nasal plenum positioned to receive pressurized gas from the mouth plenum; and a clip configured to connect the mouth plenum to the nasal plenum and act as a conduit for the flow of the pressurized gas from the mouth plenum to the nasal plenum, the clip comprising: a mouth portion end configured to engage the mouth portion; a nasal portion end configured to engage the nasal portion; and a pair of wings protruding from the nasal portion end into an interior of the nasal plenum so that the wings engage an interior surface of the nasal plenum, a base of each wing being positioned on opposing lateral sides of the clip, a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breathe from ambient through their mouth in the absence of a flow of pressurised air through the plenum chamber inlet port.

In examples, (a) the wings may be separate and distinct from each other (b) a height of each wing may be a distance each wing projects from the nasal portion end of the clip, and the maximum height of each wing may be at the laterally furthest point on the wing, (c) the height of each wing may vary so that the height of each wing increases toward the laterally furthest point on the wing, (d) the height of each wing may vary gradually to form a smooth curve, the height of each wing may decrease to a value of zero toward a central region of the nasal portion end of the clip, (e) the nasal plenum may comprise an inlet opening, and the clip may comprise a nasal end flange and a middle flange that together may form a nasal end channel configured to receive a rim of the inlet opening of the nasal plenum, the nasal end flange may be configured to be inserted into the inlet opening of the nasal plenum, (f) the pair of wings may extend from the nasal end flange, (g) the mouth plenum may comprise an outlet opening, and the clip may comprise a mouth end flange that together forms a mouth end channel that may receive a rim of the outlet opening of the mouth plenum, (h) the mouth end flange may be configured to be inserted into the mouth plenum, (i) a rim of the outlet opening of the mouth plenum may comprise a tab and there may be a notch in the mouth end flange of the clip, and the notch may be positioned to receive the tab when the nasal portion is connected to the mouth portion in the correct orientation, (j) the tab may be configured to prevent the nasal portion from being secured to the mouth portion in a wrong orientation, (k) an outer surface of the mouth portion may comprise a first printed indicia, an outer surface of the nasal portion may comprise a second printed indicia that lines up with the first printed indicia when the nasal portion is connected to the mouth portion in the correct orientation, and (l) the nasal portion may comprise a flexible base and a pair of nasal pillows attached to the flexible base, the nasal pillows may be configured to seal with an interior of the patient's nostrils.

In further example, (a) the mouth portion may comprise a flange having an inside surface and an outside surface, and the flange may comprise a target seal-forming region located on an outside surface thereof, (b) the outside surface may comprise a lip region constructed to have a lip saddle-shaped region, (c) at a point on the outside surface of the mouth portion where the mid-contact plane may touch the target seal-forming region, the curvature of the lip saddle-shaped region in the inferior-superior direction may have a negative sign and a magnitude that is larger than a magnitude of the curvature of the lip saddle-shaped region in the left-right direction, (d) the outside surface may comprise a left corner region and a right corner region, (e) the outside surface may be constructed to have a first convex dome-shaped region in said left corner region, (f) the outside surface may be constructed to have a second convex dome-shaped region in said right corner region, (g) the outside surface of said flange may have an inner edge, said hole may be bounded by said inner edge, and said inner edge may include an inner edge lip region, (h) the inner edge of said flange may be constructed so that a space curve on the outside surface of the flange at said inner edge in said left corner region may have a left-hand positive torsion, (i) the inner edge of said flange may be constructed so that a space curve on the outside surface of the flange at said inner edge in said right corner region has a right-hand positive torsion, (j) the mouth plenum may be partly formed by a shell, which has a shell inside surface and shell outside surface, and the shell inside surface may be arranged to be at said therapeutic pressure in use, and said shell outside surface may be arranged to be at ambient pressure in use, (k) the shell may be structured to be rigid when subject to an internal pressure of less than about 30 cmH2O above ambient pressure, (l) the shell may be constructed from a hard plastic material, (m) the shell may be constructed from a transparent material, (n) the shell inside surface may be constructed to include a concave dome-shaped region, (o) the positioning and stabilising structure may include a second tie, the second tie being constructed and arranged so that at least a portion of a superior edge thereof passes inferior to an otobasion inferior of the patient's head and to overlay or lie inferior to the occipital bone of the patient's head (p) the positioning and stabilising structure may include a low profile side portion configured to be positioned under the patient's head while the patient is lying in a side sleeping position, (q) the mouth plenum may be constructed from a transparent material, (r) the patient interface may be configured so that no part of the patient interface structure enters the mouth in use, or (s) the patient interface may be constructed and arranged so that the mouth plenum does not cover the eyes in use.

Another aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a nasal portion that is configured to seal with the patient's nares, the nasal portion comprising a nasal plenum positioned to receive pressurized gas from the mouth plenum chamber; and a clip configured to connect the mouth plenum chamber to the nasal plenum and act as a conduit for the flow of the pressurized gas from the mouth plenum chamber to the nasal plenum, the clip comprising: a mouth portion end configured to engage an outlet of the mouth plenum chamber; and a nasal portion end configured to engage the nasal portion, the clip being configured to add rigidity to the lateral sides of the nasal plenum so that the lateral sides of the nasal plenum are more rigid than the central portion of the nasal plenum when the clip is attached to the nasal plenum, a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breathe from ambient through their mouth in the absence of a flow of pressurised air through the plenum chamber inlet port.

In examples, (a) the clip may comprise a pair of lateral wings that extend from an end of the clip, each lateral wing may be located on opposite sides of a lumen in the clip and may be configured to increase the rigidity of the nasal plenum when the clip is attached to the nasal plenum, (b) a height of each wing may be a distance each wing projects from the end of the clip, and the maximum height of each wing may be at the laterally furthest point on the wing, (c) the height of each wing may vary so that the height of each wing increases toward the laterally furthest point on the wing, (d) the height of each wing may decrease to a value of zero toward a central region of the nasal portion end of the clip, (e) the nasal portion may comprise a nasal base and a pair of nasal pillows extending from the nasal base, (f) the nasal base may form the nasal plenum, (g) the nasal base and the nasal pillows may be formed from a flexible material, (h) the clip may be made of a material that is more rigid than the nasal portion and the mouth portion, (i) the wings may be configured to be inserted into the nasal plenum when the clip is attached to the nasal portion, (j) the wings may be configured to lodge against an interior of the nasal plenum when the clip is attached to the nasal plenum, (k) the clip may be removable from the mouth plenum, (l) the clip may be removable from the nasal plenum.

Another aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a nasal portion that is configured to seal with the patient's nares, the nasal portion comprising a nasal plenum, the nasal plenum comprising an air inlet configured to receive pressurized gas from the mouth plenum chamber; and a clip configured to connect the mouth plenum chamber to the nasal plenum and act as a conduit for the flow of the pressurized gas from the mouth plenum chamber to the nasal plenum, the clip comprising: a mouth portion end configured to engage an outlet of the mouth plenum chamber; a nasal portion end configured to engage the nasal portion; a lumen extending from the mouth portion to the nasal portion; and a pair of wings protruding from the nasal portion end into an interior of the nasal plenum, the wings being anchored to the nasal portion end at respective bases located on opposite lateral sides of the lumen, each wing extending laterally away from the lumen and terminating at a free end, a distance between the free ends of the wings being greater than a diameter of the air inlet of the nasal plenum; a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breathe from ambient through their mouth in the absence of a flow of pressurised air through the plenum chamber inlet port.

In examples, (a) the wings may engage an interior surface of the nasal plenum, (b) the clip may be configured so that a force necessary to insert the clip into the nasal plenum is less than a force necessary to remove the clip from the nasal plenum, (c) a force necessary to remove the clip from the nasal plenum may be between 19 and 20 N, (d) each wing may be movable relative to the interior surface of the nasal plenum base after the clip is secured to the nasal plenum, (e) the wings may resist the removal of the clip from the nasal plenum, (f) the clip may comprise a nasal end flange and a middle flange that together form a nasal end channel configured to receive a rim of the air inlet of the nasal plenum, the nasal end flange may be configured to be inserted into the inlet opening of the nasal plenum, (g) the pair of wings may extend from the nasal end flange, the mouth plenum may comprise an outlet opening, and the clip may comprise a mouth end flange that together forms a mouth end channel that receives a rim of the outlet opening of the mouth plenum, (h) the mouth end flange may be configured to be inserted into the mouth plenum.

Another aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a mouth portion that forms at least part of the mouth plenum and is configured to seal around the patient's mouth, the mouth portion comprising a receptacle with an outlet opening and a pair of mouth portion magnets positioned on opposite sides of the outlet opening; and a nasal portion that is configured to seal with the patient's nares, the nasal portion comprising a nasal plenum with an inlet opening and a pair of nasal portion magnets positioned on opposite sides of the inlet opening, the nasal plenum being configured to be received within the receptacle and the nasal portion magnets being positioned so that both of the nasal portion magnets are between the mouth portion magnets when the nasal plenum is received within the receptacle; a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use; wherein the patient interface is configured to allow the patient to breathe from ambient through their mouth in the absence of a flow of pressurised air through the plenum chamber inlet port.

In examples, (a) the receptacle may comprise at least one side wall extending from the base, and the mouth portion magnets may be positioned on the at least one side wall, (b) the nasal plenum may comprise at least one side wall and the nasal portion magnets may be positioned on the at least one side wall, (c) the nasal portion magnets may be on lateral sides of the nasal plenum, (d) the mouth portion magnets may be on lateral sides of the receptacle, (e) the nasal portion magnets may be oriented to present different polarities toward the mouth portion magnets, (f) the mouth portion magnets may be oriented to present different polarities toward the nasal portion magnets, (g) the nasal portion magnets and the mouth portion magnets may be oriented to repel each other when the nasal plenum is inserted into the receptacle in the wrong orientation, (h) the nasal portion magnets and the mouth portion magnets may be configured to connect two flexible bodies, (i) the nasal portion magnets may be molded to the nasal plenum and the mouth portion magnets may be molded to the receptacle, (j) a bottom of a rim of the inlet opening in the nasal plenum may comprise a lip seal, (k) the lip seal may be configured to engage a rim of the outlet opening of the receptacle when the nasal plenum may be secured within the receptacle, (l) the lip seal may be positioned below the nasal portion magnets, (m) the nasal portion magnets may face each other (n) the mouth portion magnets may face each other.

Another aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a mouth portion that forms at least part of the mouth plenum and is configured to seal around the patient's mouth; and a nasal portion that is configured to seal with the patient's nares, the nasal portion comprising a nasal plenum with an inlet opening, the nasal plenum being configured to be received within the receptacle; a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use, the vent structure comprising: a main body configured to be secured to the mouth portion, the main body comprising a vent wall with a plurality of vent holes, a receptacle, and a pair of anchor sockets located on opposing lateral sides of the receptacle; a cover comprising a pair of anchor pegs on lateral sides of the cover, the anchor pegs being configured to be inserted into the anchor sockets to secure the cover to the main body; and a diffuser received within the receptacle between the anchor sockets, the diffuser being sandwiched between the main body and the cover, wherein the patient interface is configured to allow the patient to breathe from ambient through their mouth in the absence of a flow of pressurised air through the plenum chamber inlet port.

In examples, (a) the anchor sockets may be keyed with the anchor pegs so that only anchor pegs with the same shape as the anchor sockets are receivable within the anchor sockets, (b) the anchor sockets may be tapered so that the anchor pegs become wedged in the anchor sockets when the cover is secured to the main body, (c) the main body may comprise a first flange and a second flange that forms a channel with the first flange, the mouth portion may comprise a vent opening and a rim of the vent opening may be received in the channel when the main body is secured to the mouth portion, (d) the anchor sockets may extend deeper than the channel, (e) the vent wall may enclose an end of the receptacle that is closest to the interior of the mouth plenum, (f) the diffuser may be spaced apart from the vent holes, (g) each anchor socket may have a different size, (h) each anchor socket may have a different shape, (i) the anchor sockets may be configured to prevent the cover from being secured to the main body in the wrong orientation, (j) a perimeter of the cover may be smaller than a perimeter of the main body so that a gap may be formed between the main body and the cover when the cover is secured to the main body, (k) the vent holes may be tapered so that the vent holes narrow in a direction toward the diffuser, (l) opposing sides of the interior wall of each vent hole may form an angle of taper 10 to 35 degrees, (m) the angle of taper may be about 10 degrees, (n) the angle of taper may be about 35 degrees, (o) a base of each vent hole may be flared, (p) the flared portion of the vent hole may have a radius of curvature of 0.2 mm to 0.4 mm, (q) the radius of curvature may be about 0.25 mm, (r) the radius of curvature may be about 0.3 mm, (s) a smallest diameter of each vent hole may be 0.5 mm to 2.0 mm, (t) the smallest diameter may be 0.89 mm, (u) the smallest diameter may be 0.98 mm, (v) the smallest diameter may be 1.01 mm, (w) the smallest diameter may be 1.17 mm.

Another aspect of the present technology is directed to a patient interface that includes: a mouth plenum chamber pressurisable to a therapeutic pressure of at least 6 cmH$_2$O above ambient air pressure, said mouth plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, the seal-forming structure comprising: a mouth portion that forms at least part of the mouth plenum and is configured to seal around the patient's mouth; and a nasal portion that is configured to seal with the patient's nares, the nasal portion comprising a nasal plenum with an inlet opening, the nasal plenum being configured to be received within the receptacle; a positioning and stabilising structure to provide a force to hold the seal-forming structure in a therapeutically effective position on the patient's head; and a vent structure to allow a continuous flow of gases exhaled by the patient from an interior of the plenum chamber to ambient, said vent structure being sized and shaped to maintain the therapeutic pressure in the plenum chamber in use, the vent structure comprising: a vent wall with a plurality of vent openings and a trough on an outwardly facing surface that completely encircles the vent openings; at least one side wall extending from the vent wall; and a flange extending from an end of the at least one side wall so that an edge of the vent wall, an outer surface of the at least one side wall, and the flange together form a channel configured to receive a rim around the vent opening in the mouth portion, the flange being configured to be received inside the mouth plenum, wherein the patient interface is configured to allow the patient to breathe from ambient through their mouth in the absence of a flow of pressurised air through the plenum chamber inlet port.

In examples, (a) the outwardly facing surface of the vent wall may be convex and an inwardly facing surface of the vent wall opposite the outwardly facing surface may be convex, (b) the vent holes may be tapered so that the vent holes narrow in a direction toward the outwardly facing surface of the vent wall, (c) opposing sides of the interior wall of each vent hole may form an angle of taper 10 to 35 degrees, (d) the angle of taper may be about 10 degrees, (e) the angle of taper may be about 35 degrees, (f) a base of each vent hole may be flared, (g) the flared portion of the vent hole may have a radius of curvature of 0.2 mm to 0.4 mm, (h) the radius of curvature may be about 0.25 mm, (i) the radius of curvature may be about 0.3 mm, (j) a smallest diameter of each vent hole may be 0.5 mm to 2.0 mm, (k) the smallest diameter may be 0.89 mm, (l) the smallest diameter may be 0.98 mm, (m) the smallest diameter may be 1.01 mm, (n) the smallest diameter may be 1.17 mm.

In yet another aspect of the present technology is directed to a respiratory therapy system that includes: the patient interface according to any of the aspects of the present technology discussed above; a respiratory pressure therapy device configured to generate the flow of air at the therapeutic pressure; and an air circuit configured to direct the flow of air at the therapeutic pressure from the respiratory pressure therapy device to the patient interface.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1A:
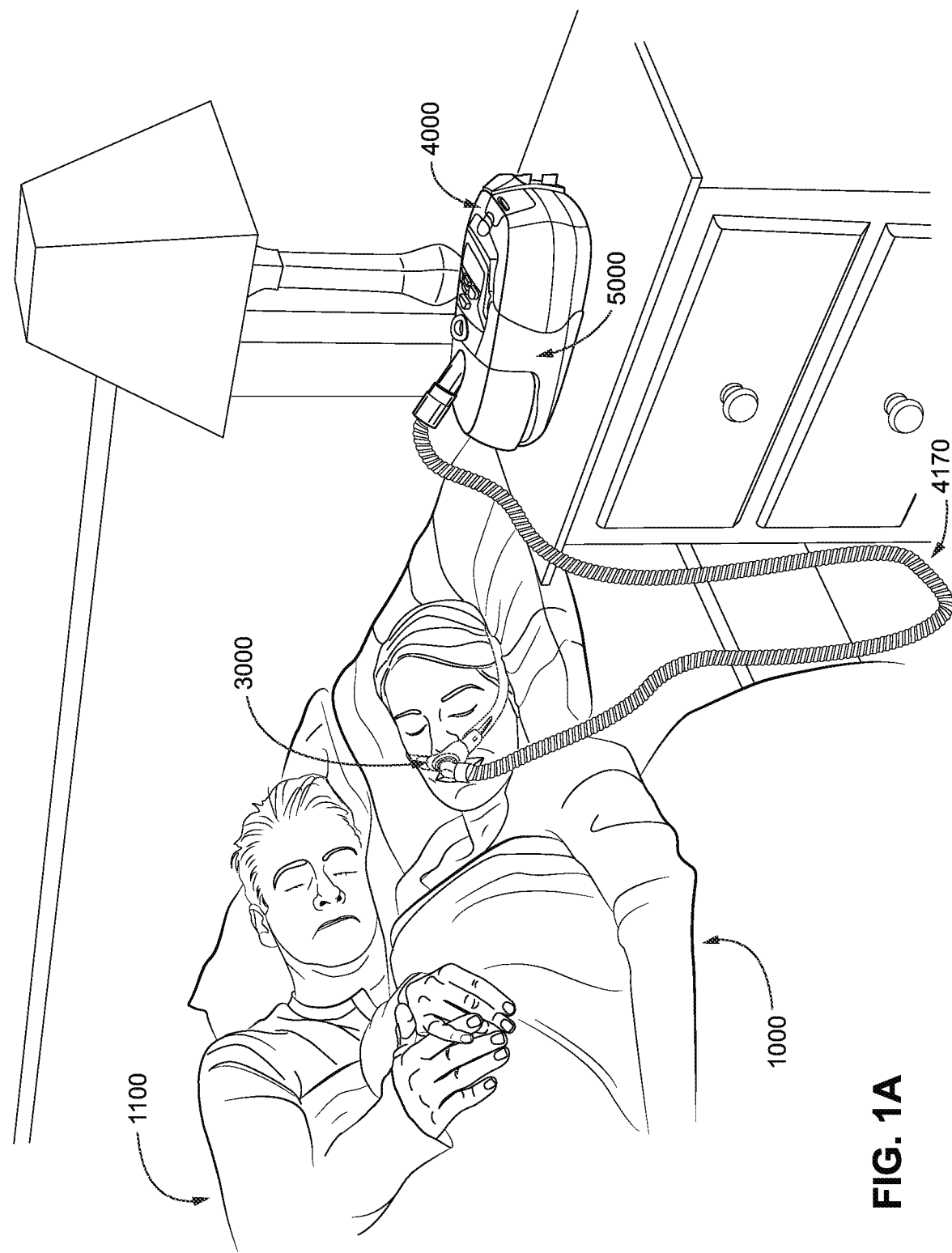
Figure 1B:
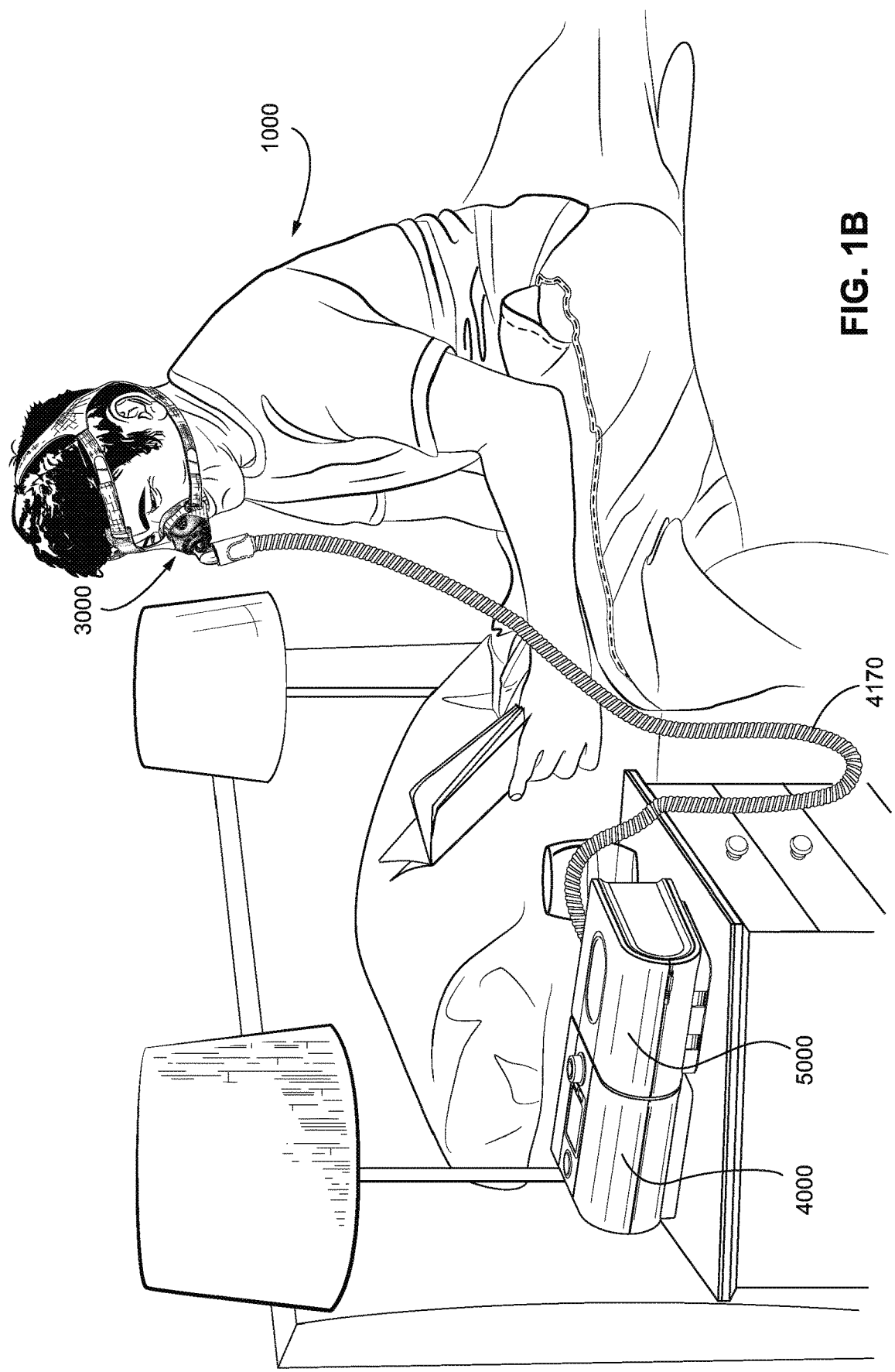
Figure 1C:
Figure 2A:
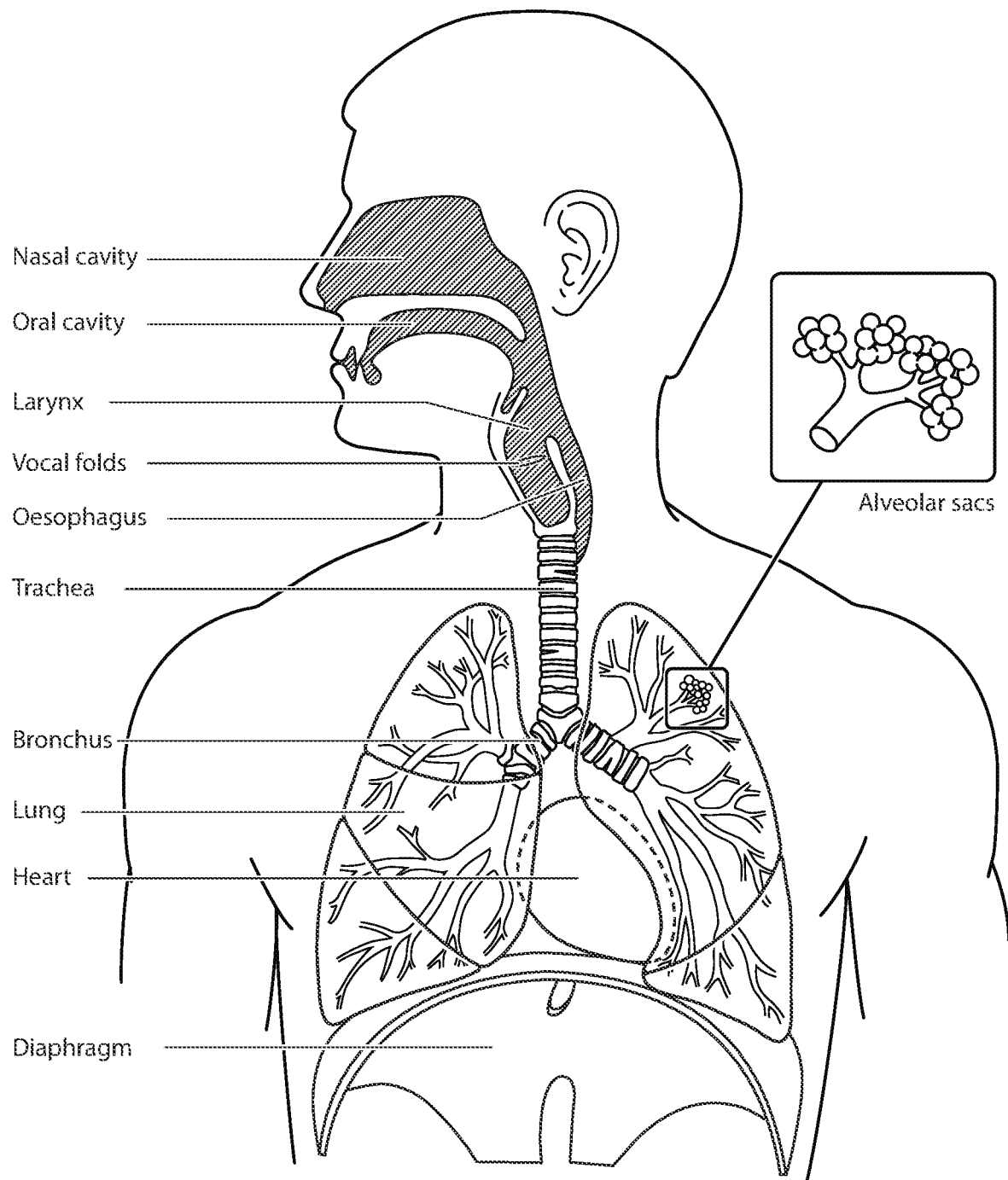
FIG. 2A shows an overview of a human respiratory system including the nasal and oral cavities, the larynx, vocal folds, oesophagus, trachea, bronchus, lung, alveolar sacs, heart and diaphragm.
Figure 2B:
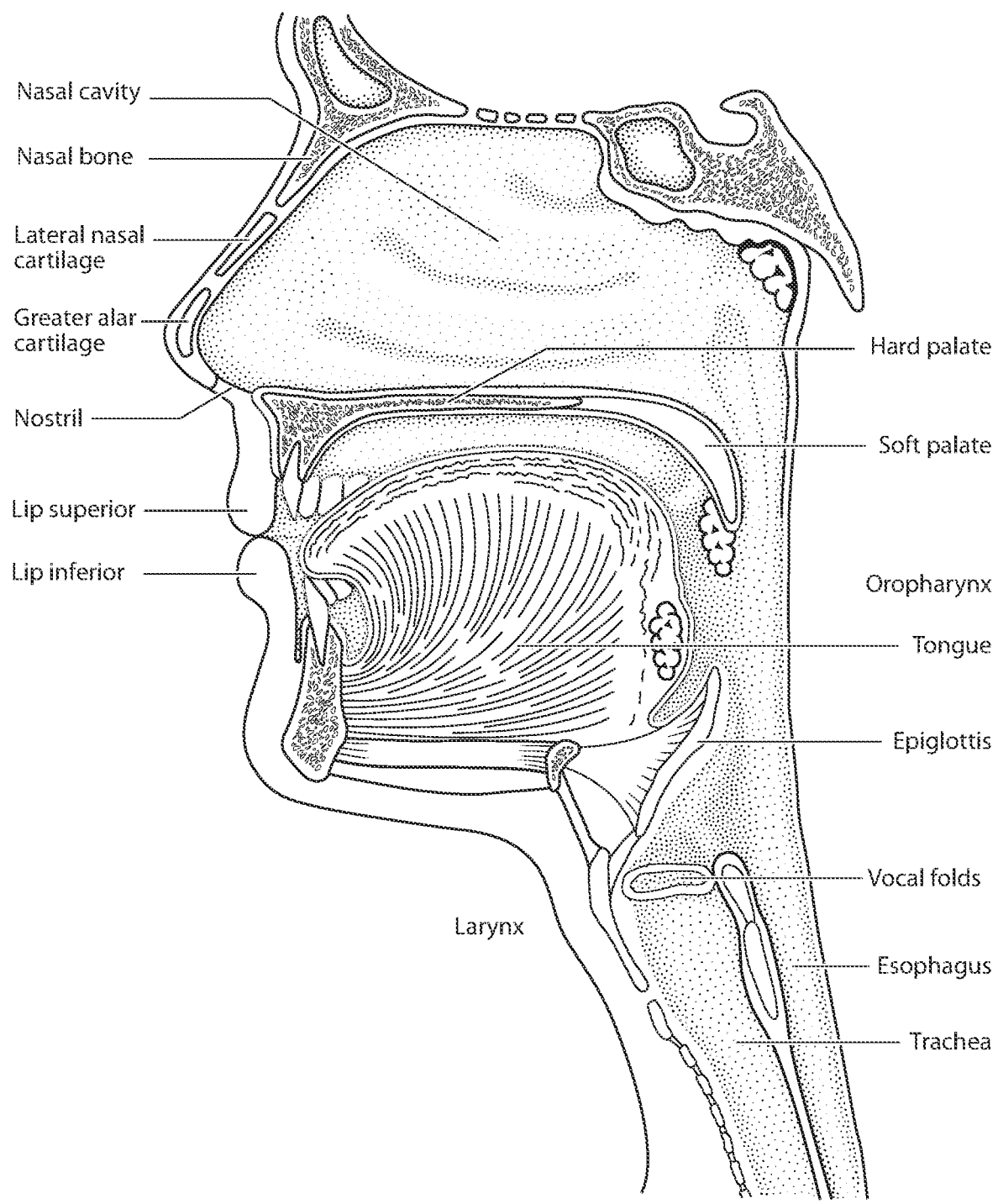
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
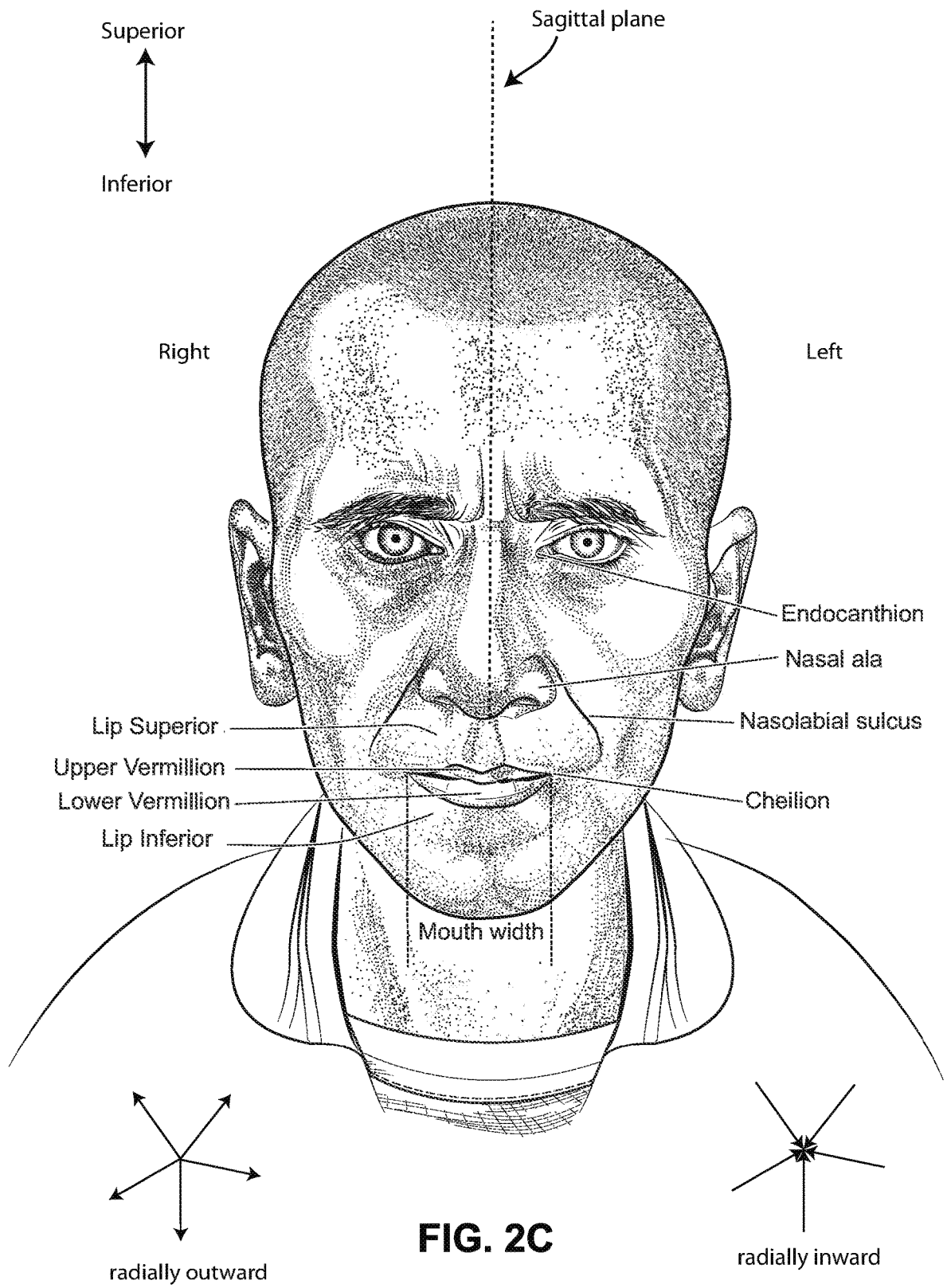
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
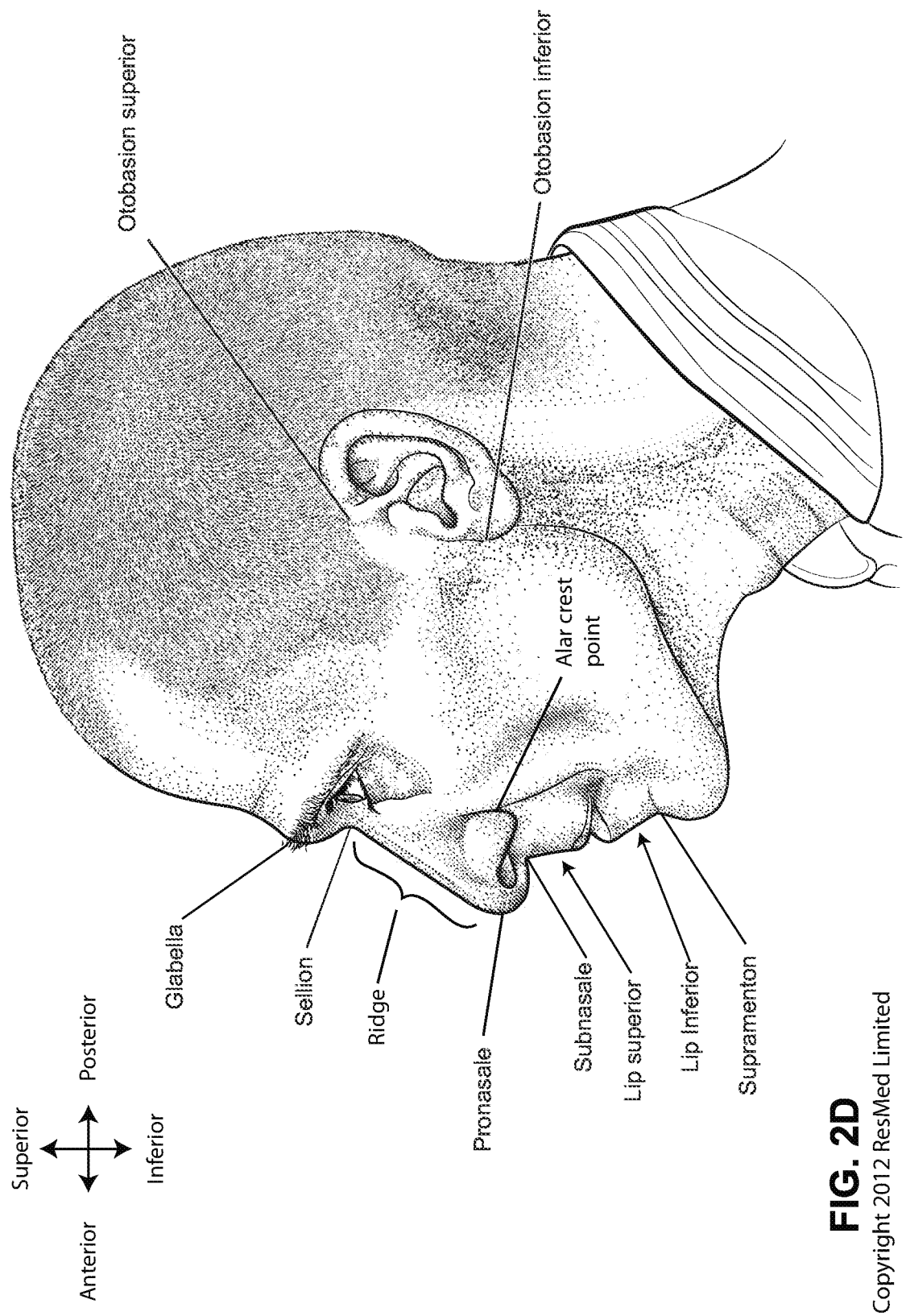
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
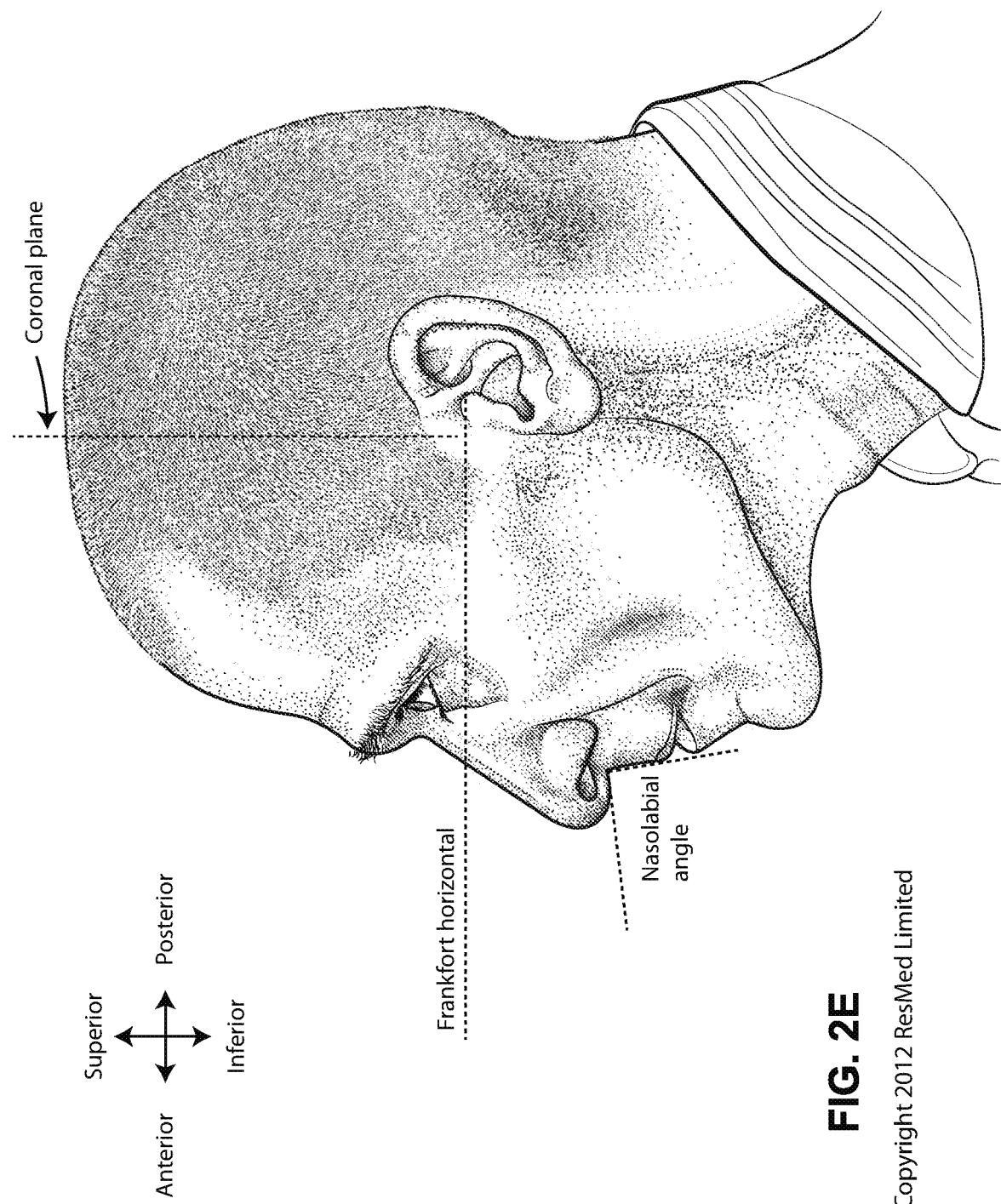

FIG. 2E is a further side view of a head. The approximate locations of the Frankfort horizontal and nasolabial angle are indicated. The coronal plane is also indicated.

Figure 2F:
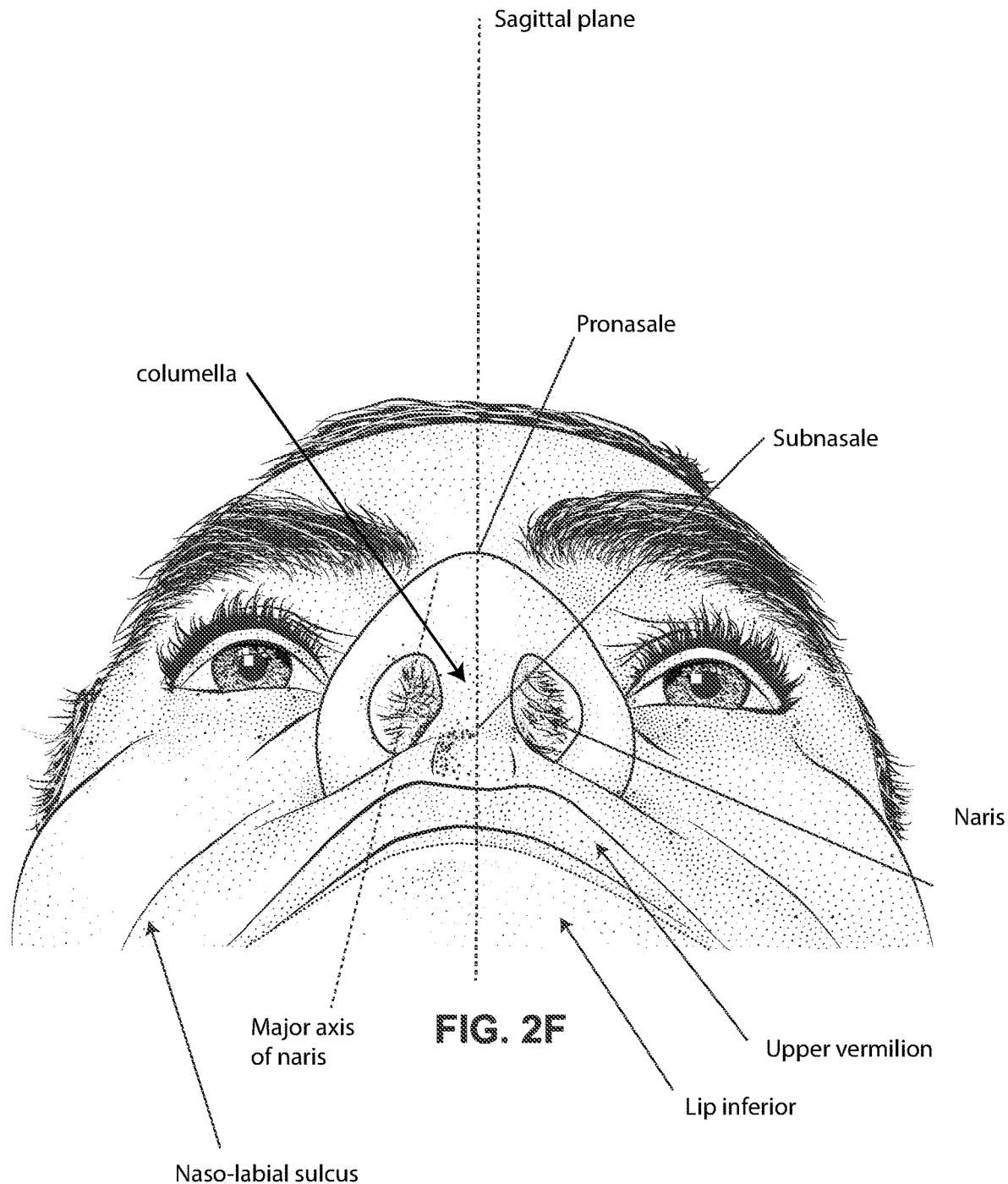

FIG. 2F shows a base view of a nose with several features identified including naso-labial sulcus, lip inferior, upper Vermilion, naris, subnasale, columella, pronasale, the major axis of a naris and the midsagittal plane.

Figures 2G, 2H, 2I:
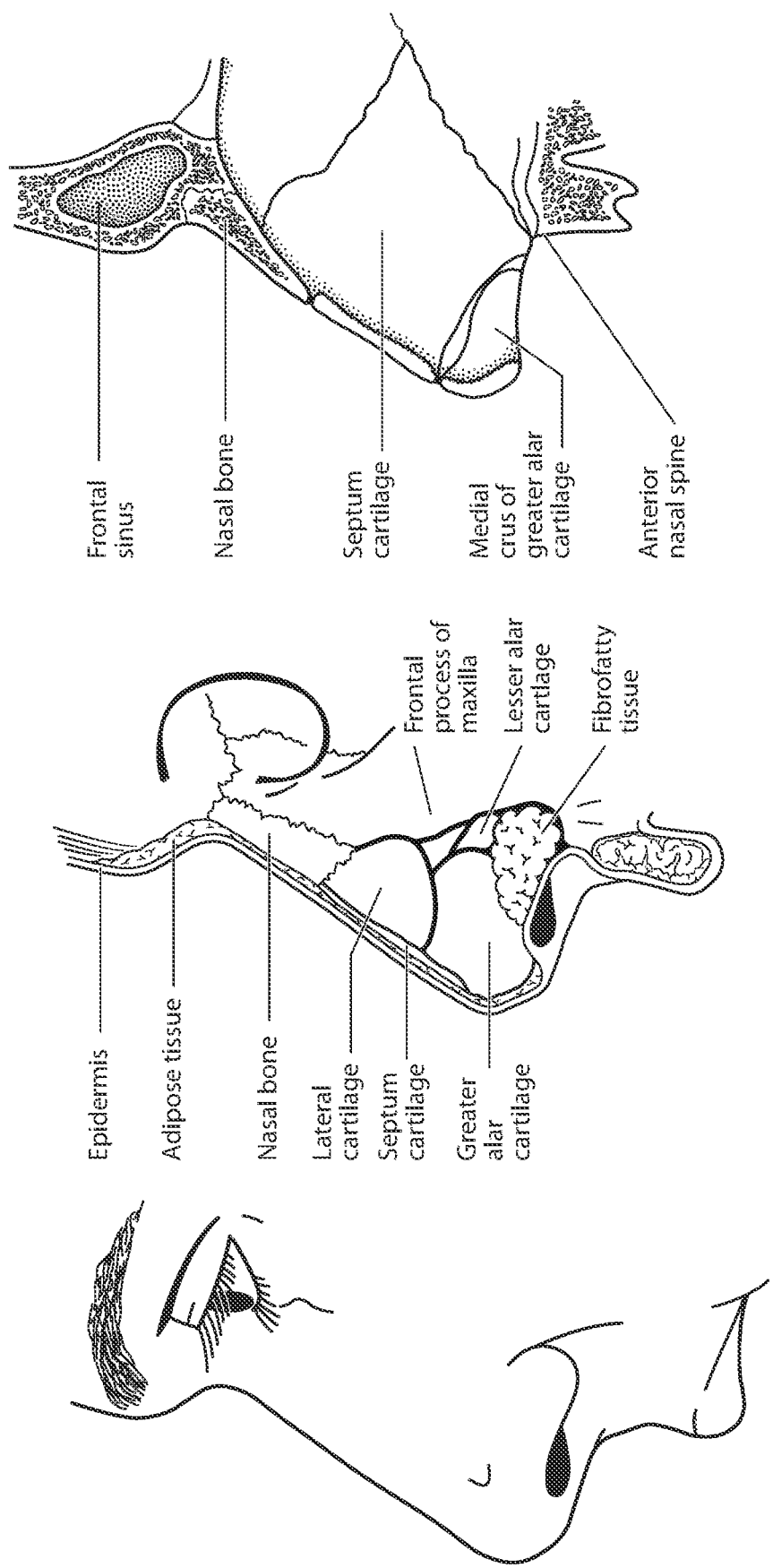

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
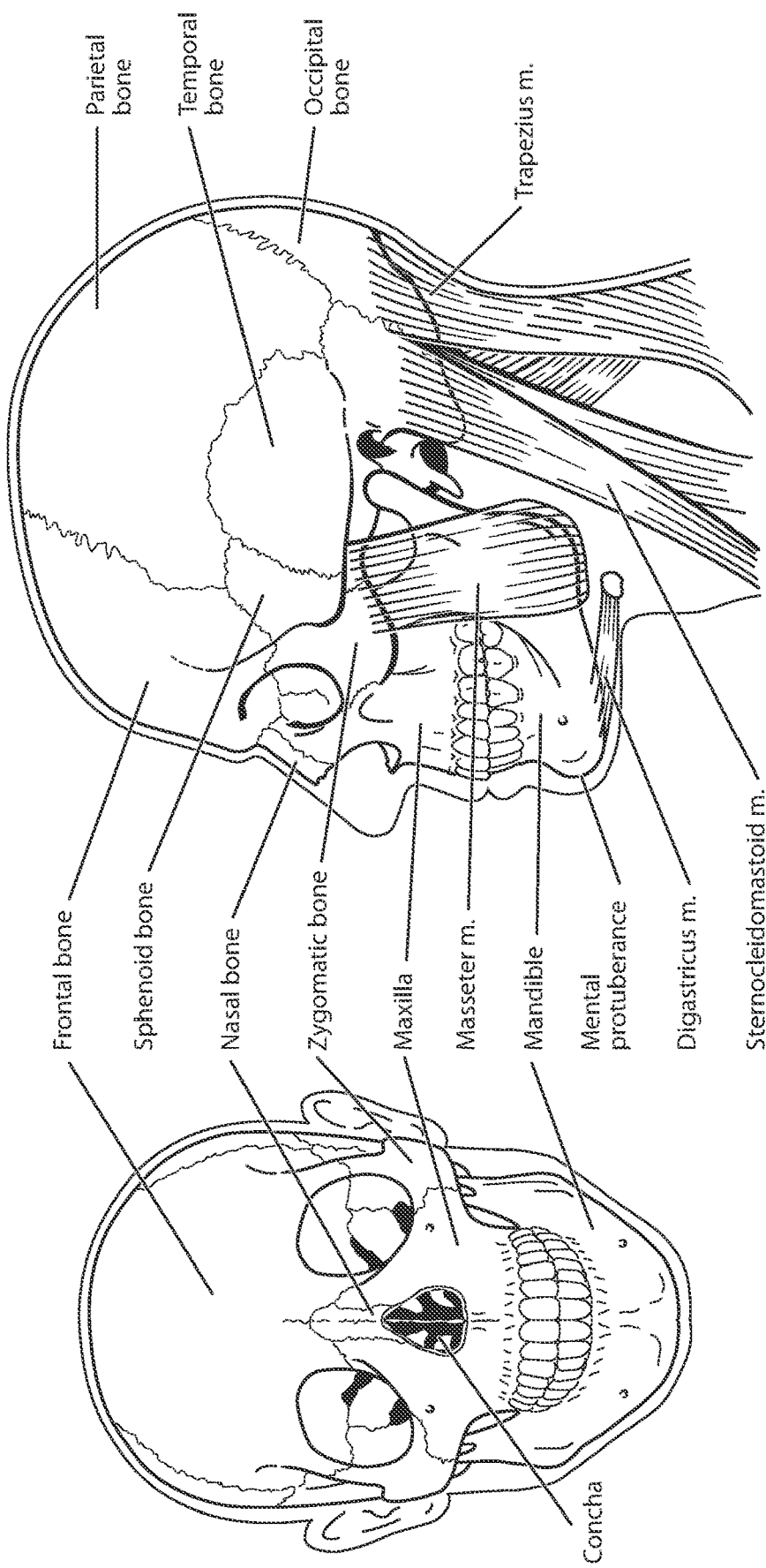

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
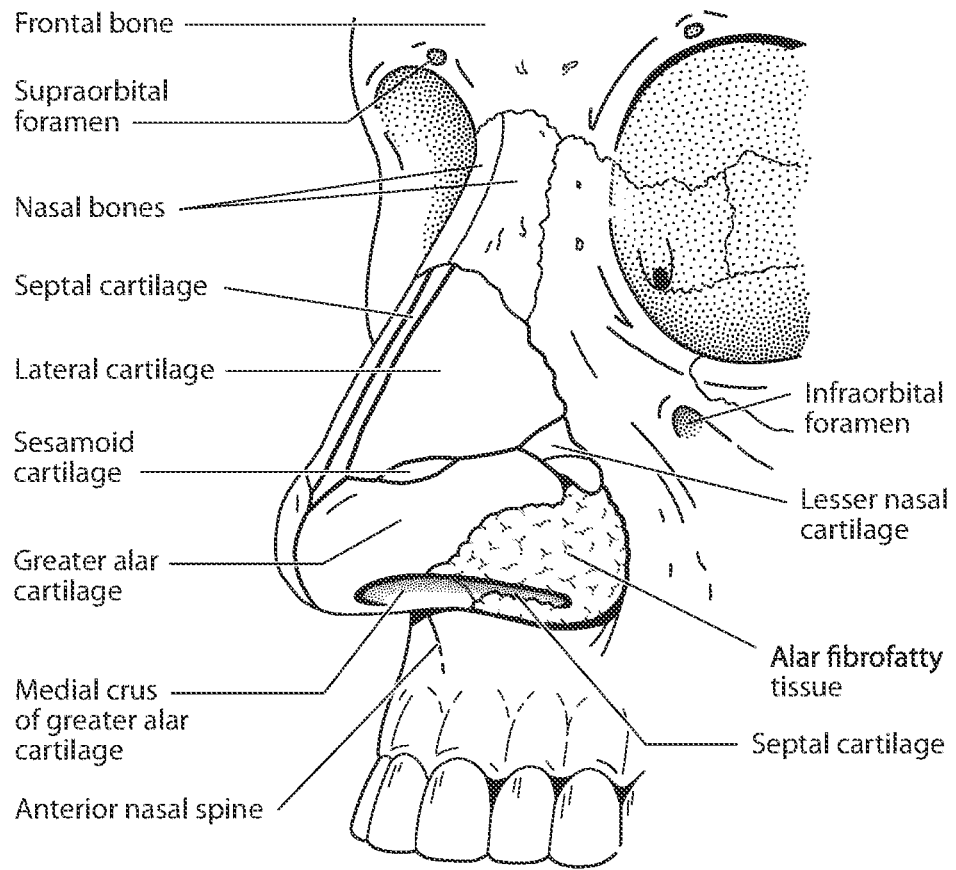

FIG. 2L shows an anterolateral view of a nose.

3.3 Patient Interface

Figure 3A:
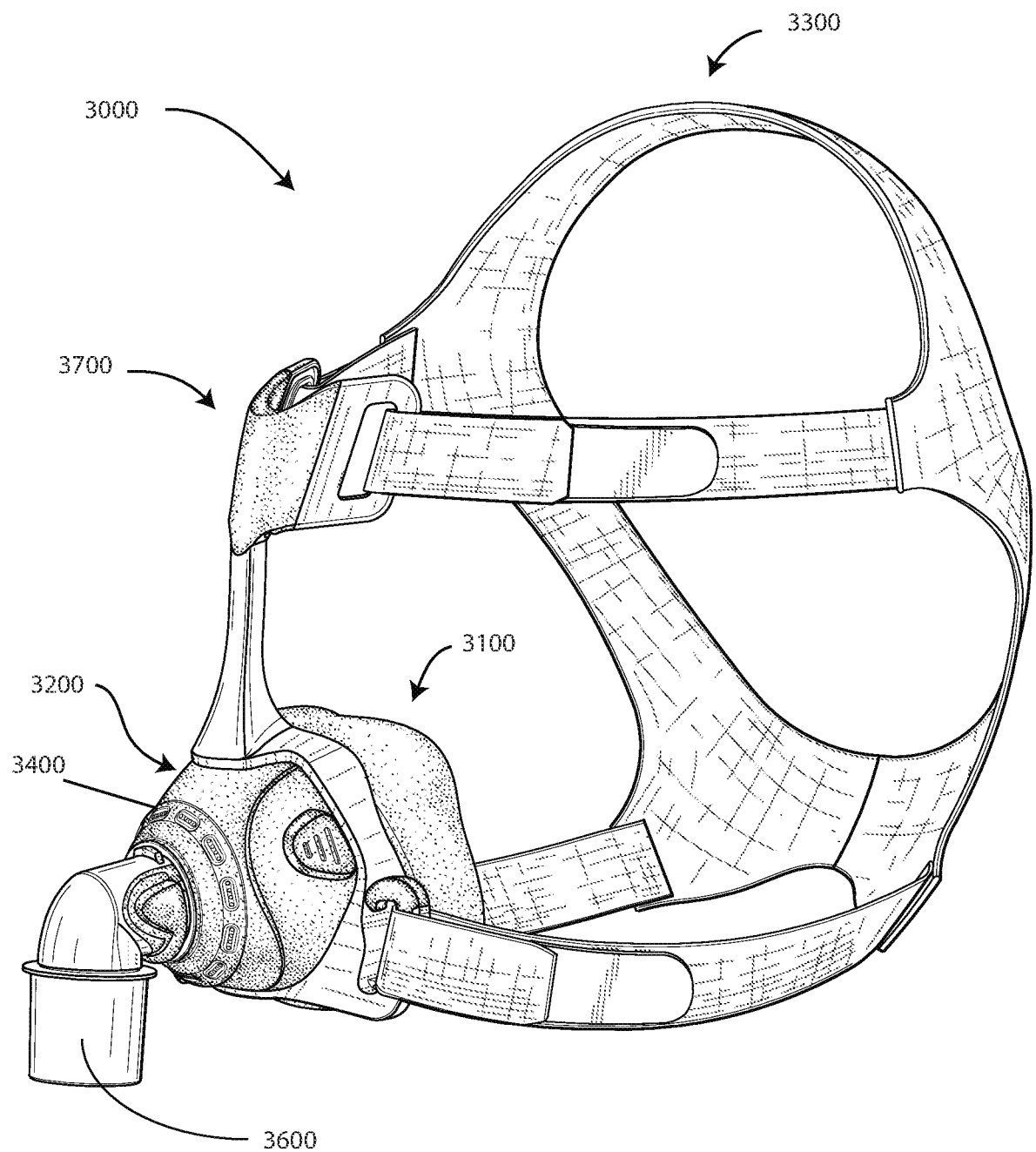

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
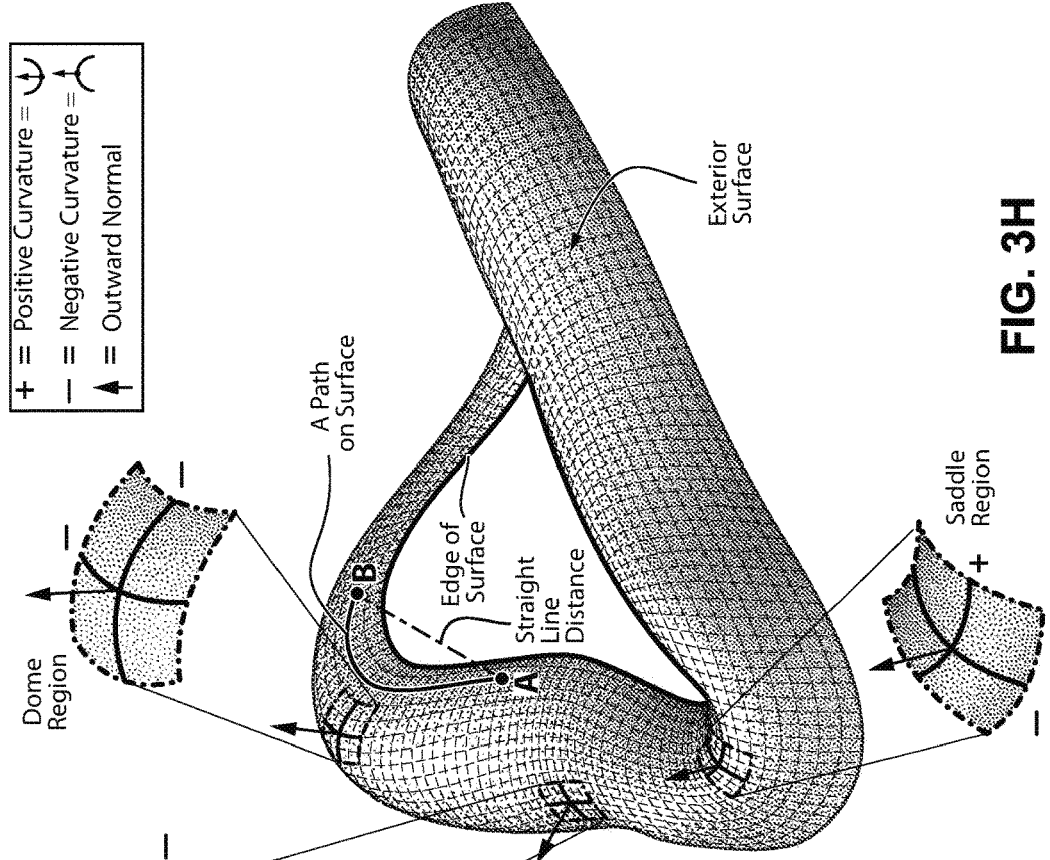
Figure 3G:
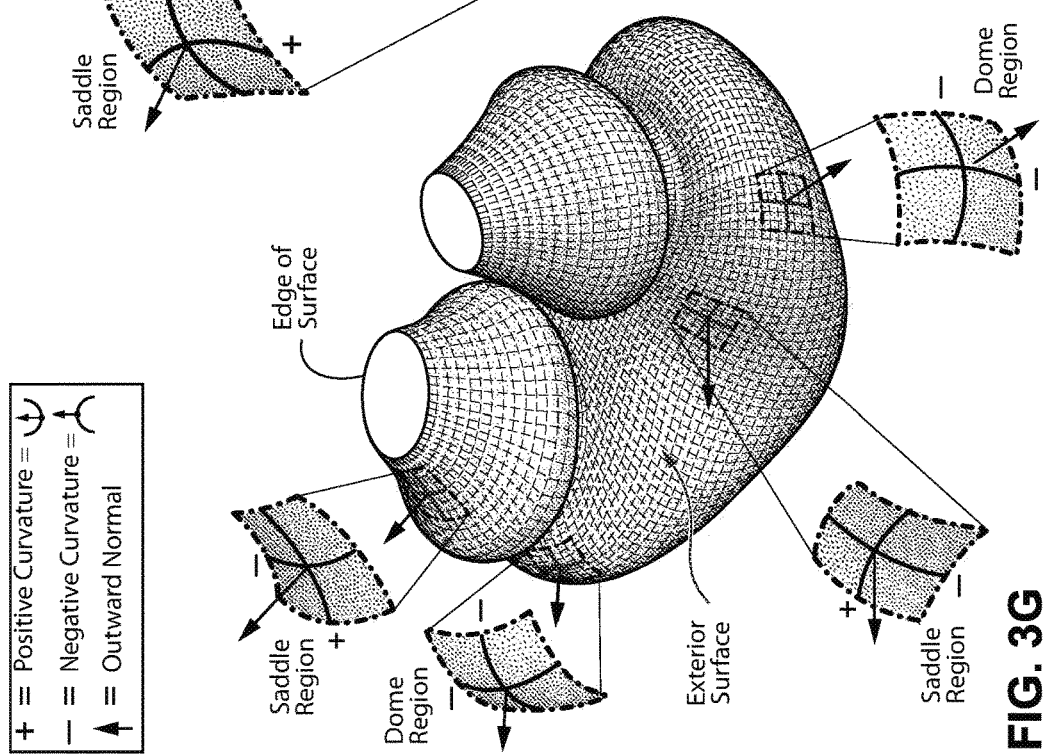

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
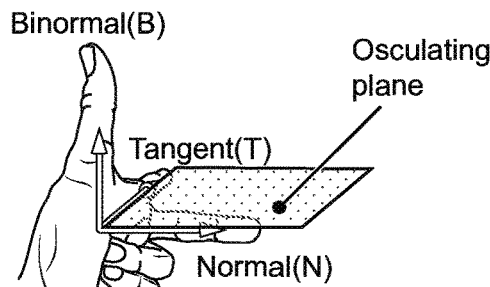

FIG. 3O illustrates a left-hand rule.

Figure 3P:
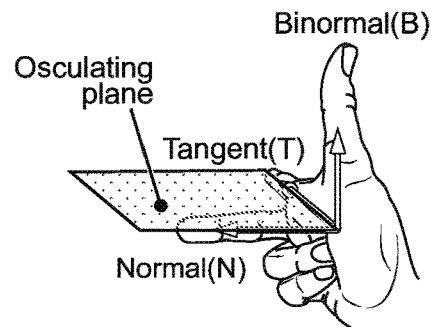

FIG. 3P illustrates a right-hand rule.

Figure 3Q:
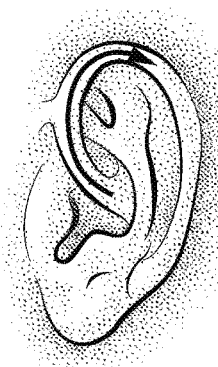

FIG. 3Q shows a left ear, including the left ear helix.

Figure 3S:
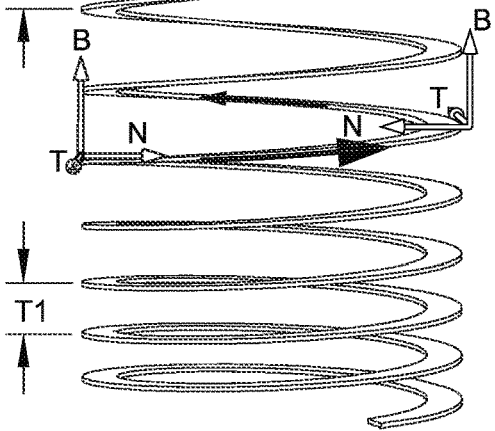
Figure 3R:
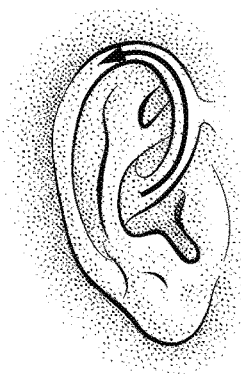

FIG. 3R shows a right ear, including the right ear helix.

FIG. 3S shows a right-hand helix.

Figure 3T:
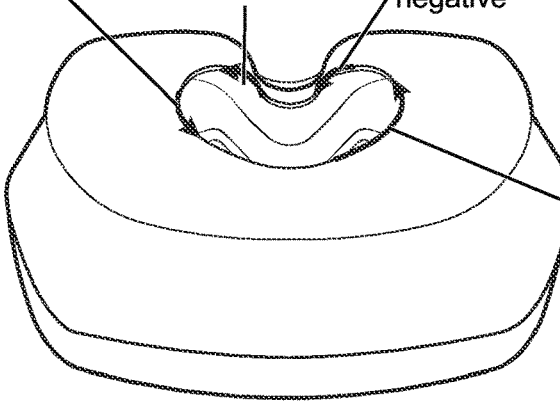

FIG. 3T shows a view of a mask, including the sign of the torsion of the space curve defined by the edge of the sealing membrane in different regions of the mask.

FIG. 3U shows a view of a plenum chamber 3200 showing a sagittal plane and a mid-contact plane.

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

Figure 3Y:
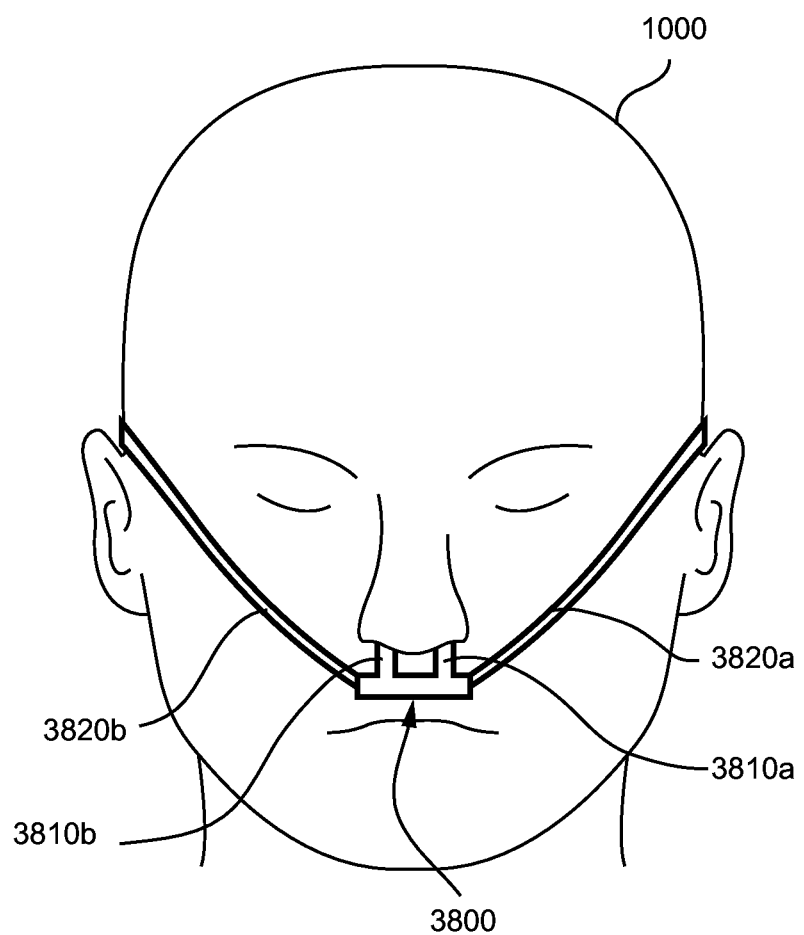

FIG. 3Y shows a patient interface in the form of a nasal cannula in accordance with one form of the present technology.

3.4 RPT Device

Figure 4A:
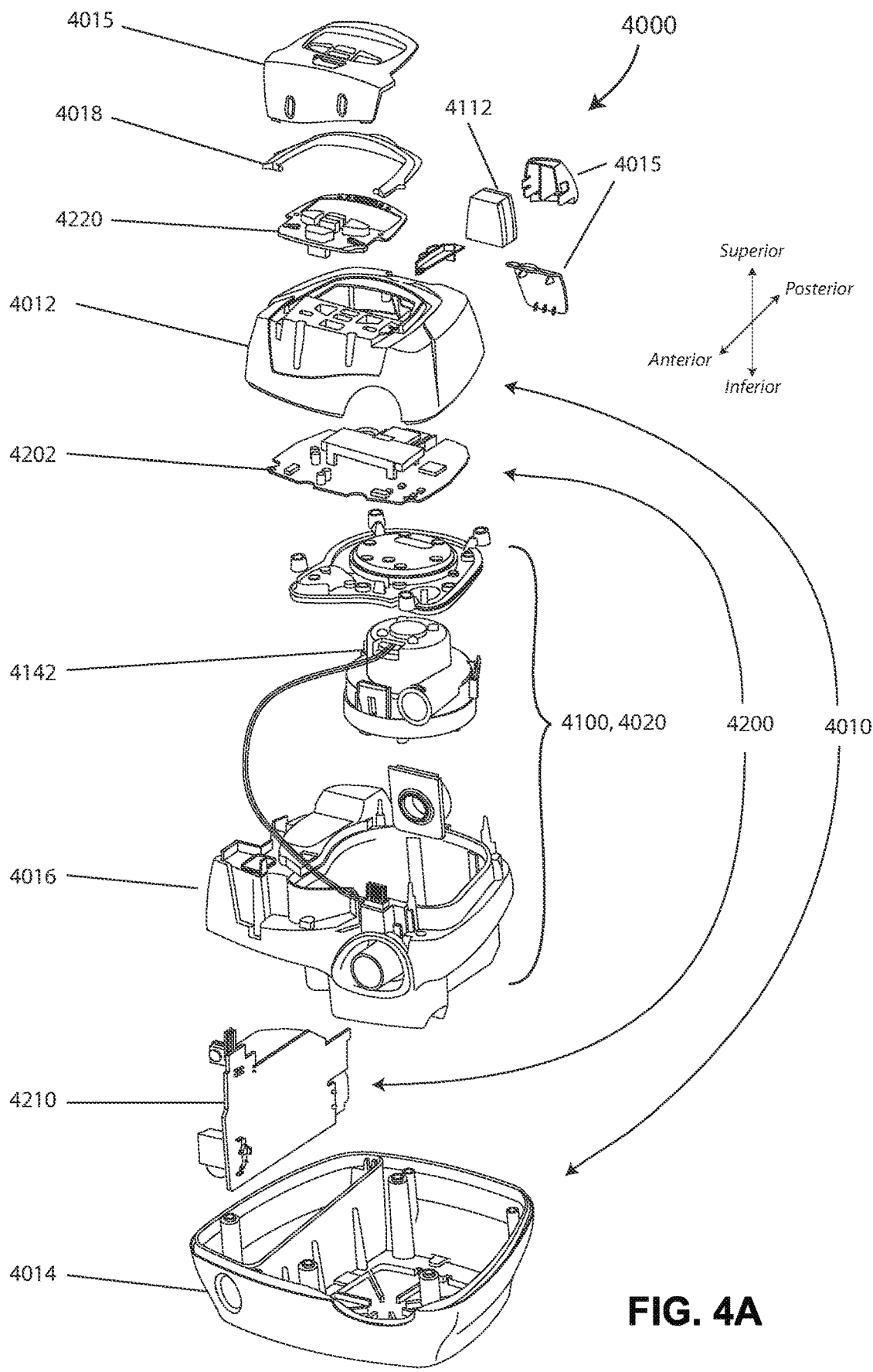

FIG. 4A shows an RPT device in accordance with one form of the present technology.

Figure 4B:
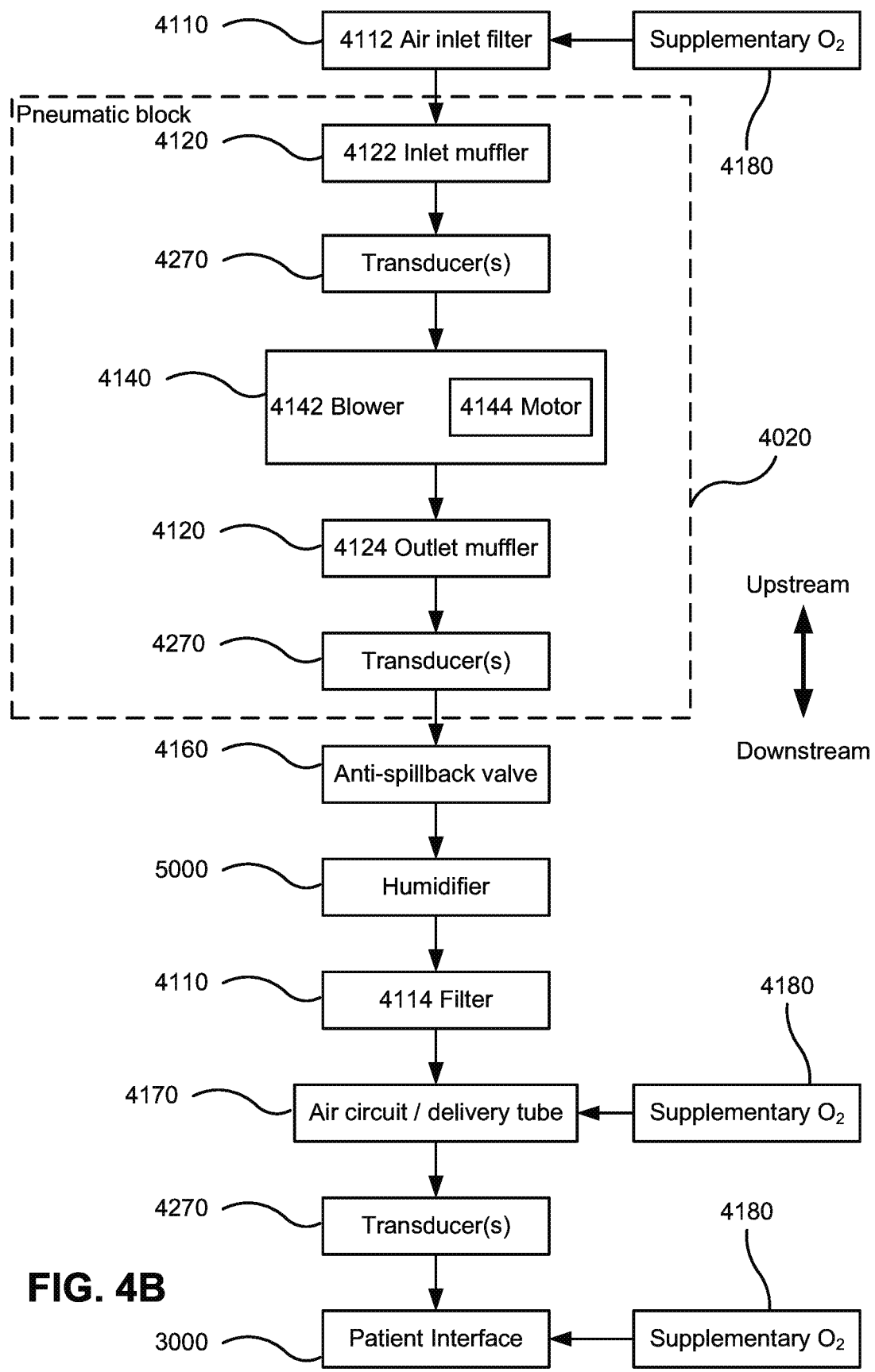

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

3.5 Humidifier

Figure 5A:
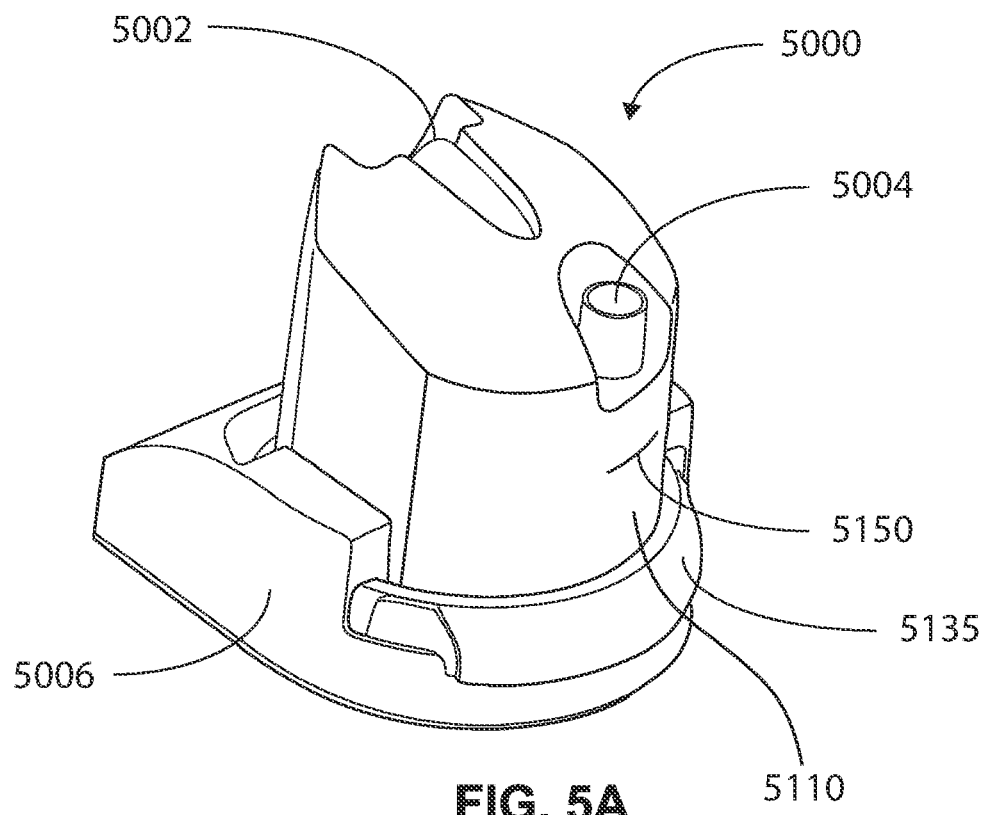

FIG. 5A shows an isometric view of a humidifier in accordance with one form of the present technology.

Figure 5B:
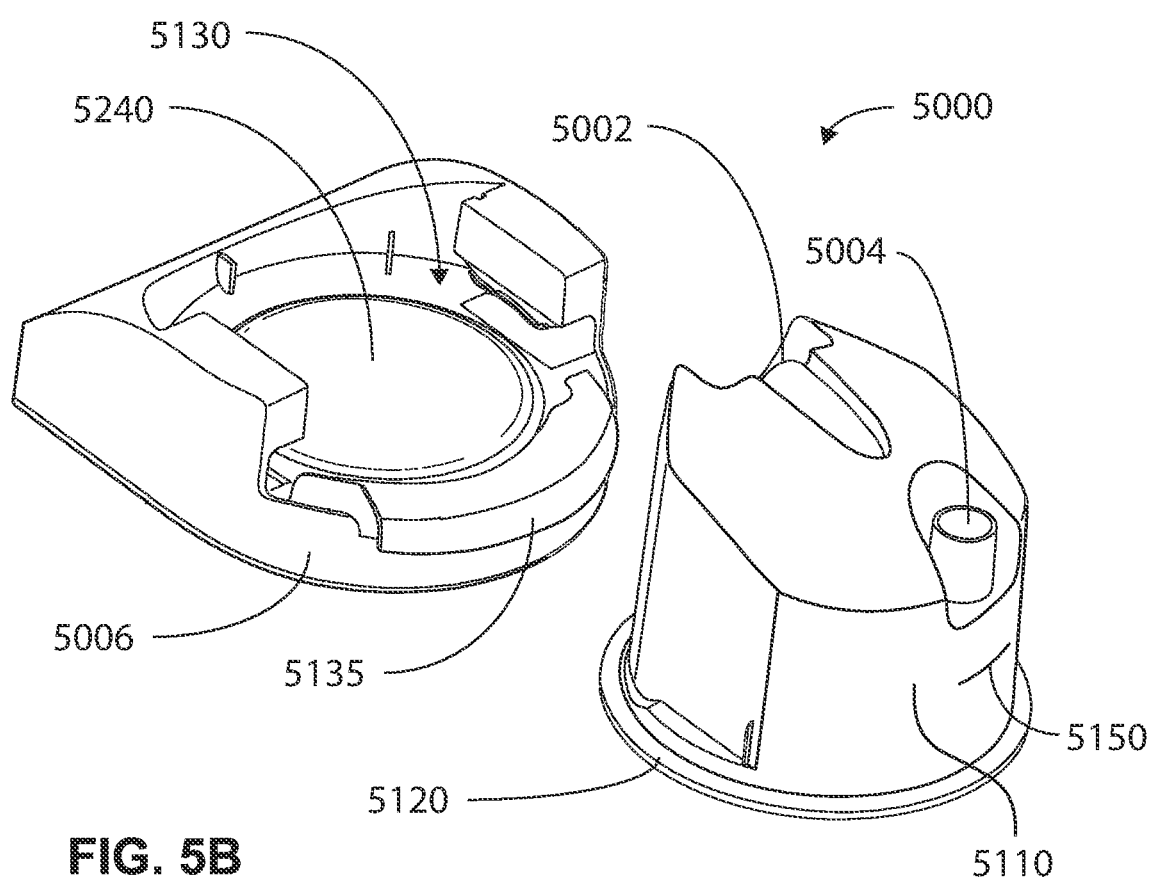

FIG. 5B shows an isometric view of a humidifier in accordance with one form of the present technology, showing a humidifier reservoir 5110 removed from the humidifier reservoir dock 5130.

3.6 Examples of the Present Technology

Figure 6:
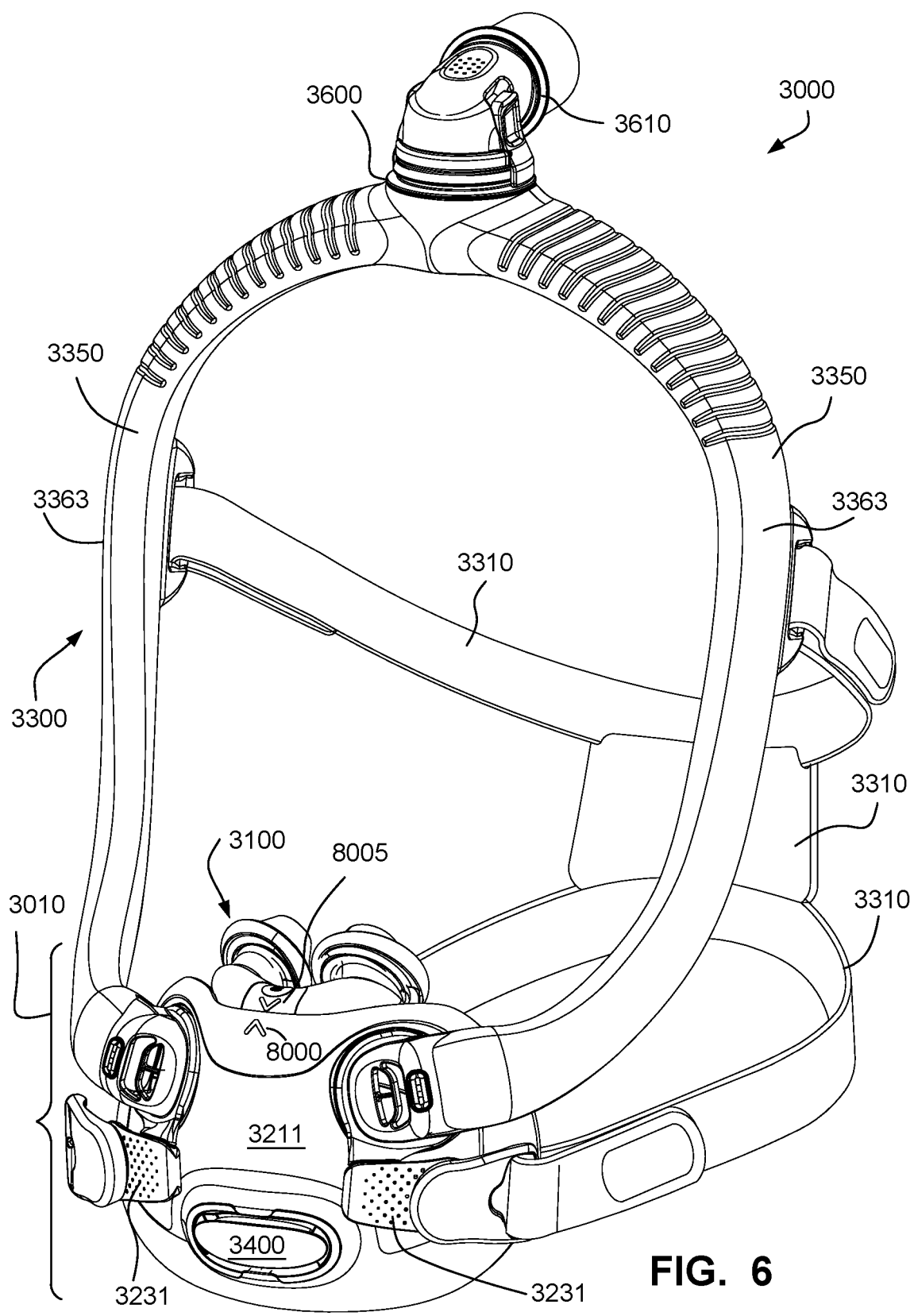

FIG. 6 shows an exemplary patient interface in accordance with one form of the present technology.

Figure 7:
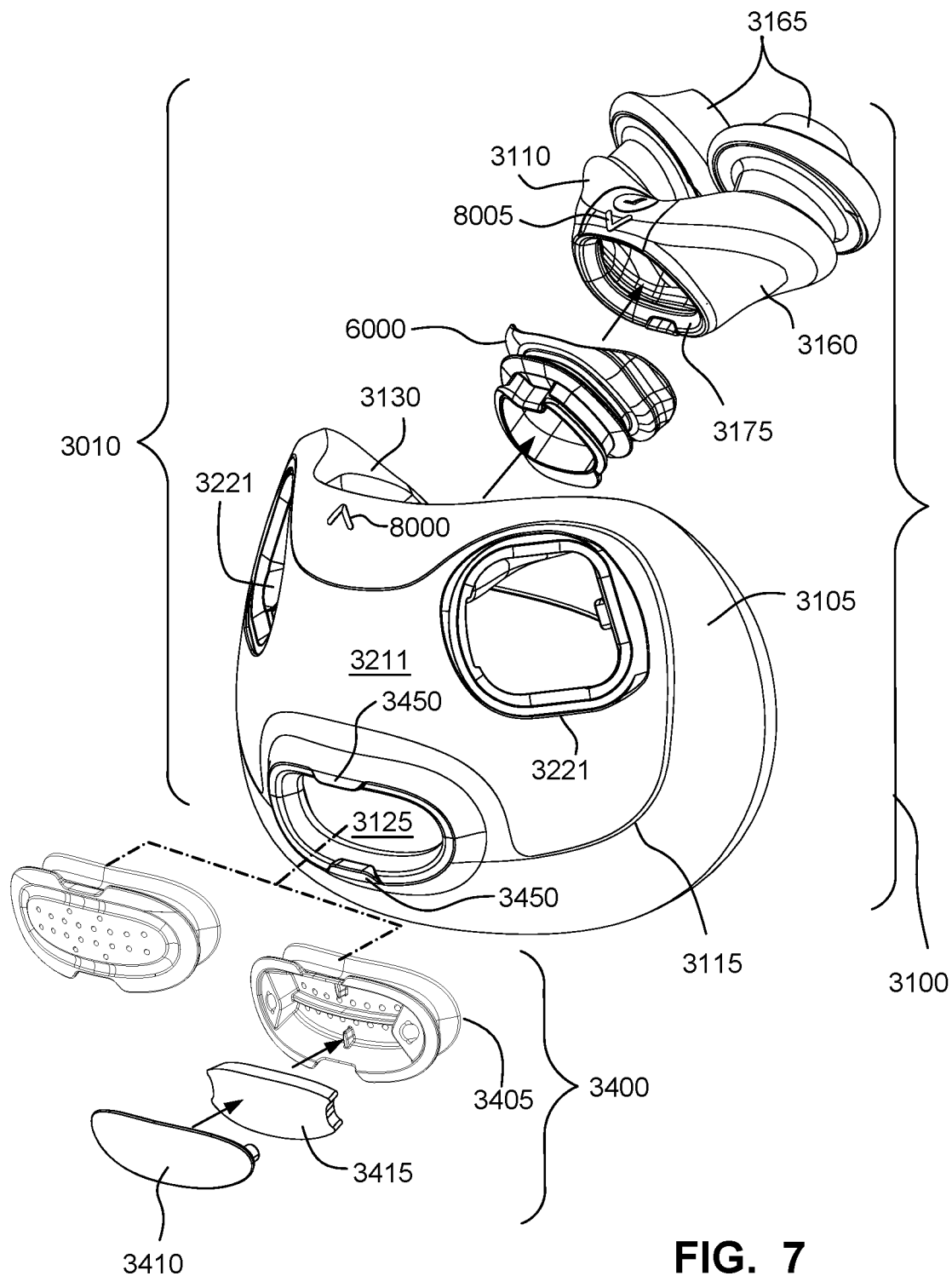

FIG. 7 shows an exploded view of the patient interface of FIG. 7.

Figure 8:
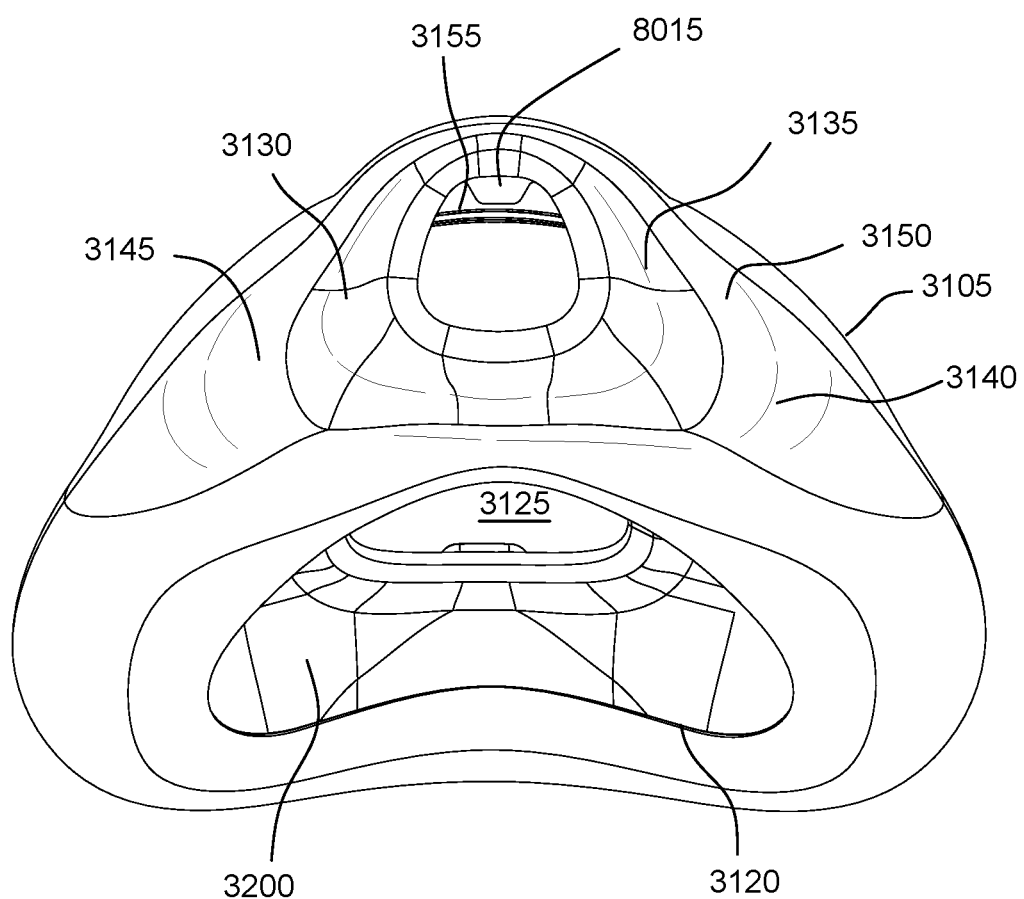

FIG. 8 shows a rear view of a main body of the patient interface of FIG. 7.

FIG. 9 shows a cross-sectional view of a nasal pillow module in accordance with an aspect of the technology.

FIGS. 9A-9C show cross-sectional views of flanges of the nasal pillow module.

Figure 10:
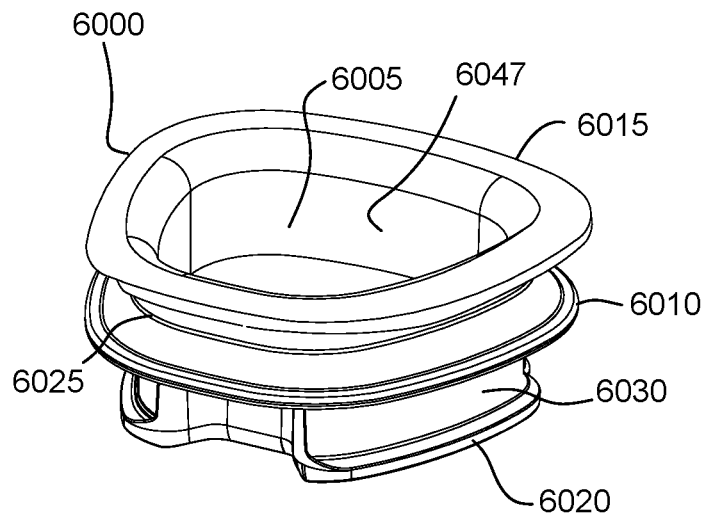
Figure 11:
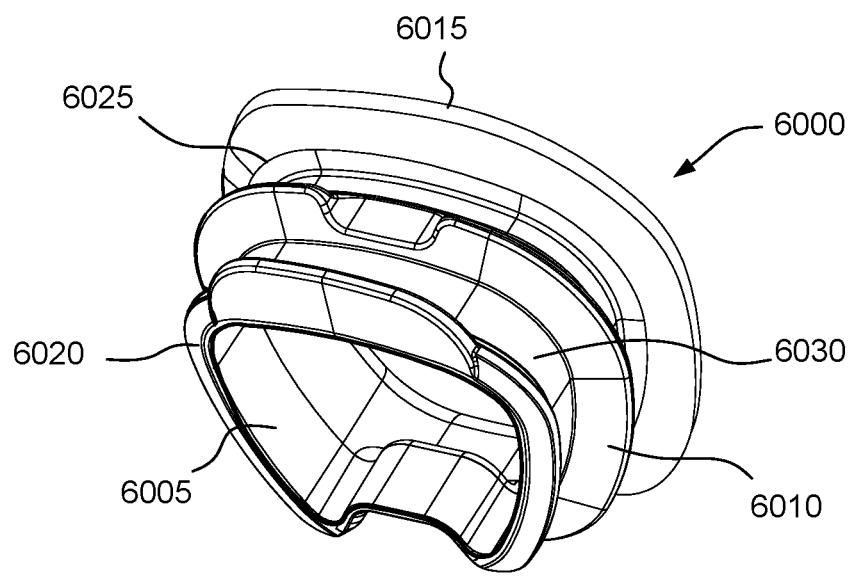
Figure 12:
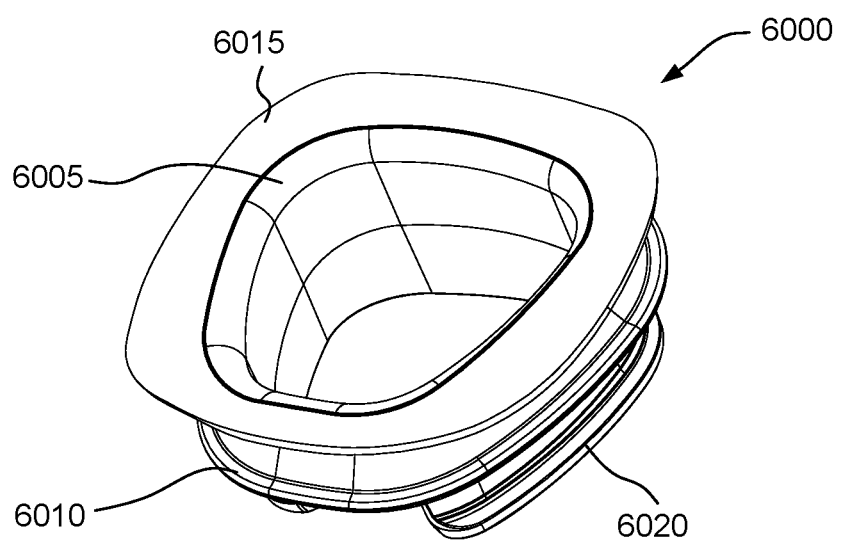

FIGS. 10-12 show different views of an exemplary cushion clip.

Figure 13:
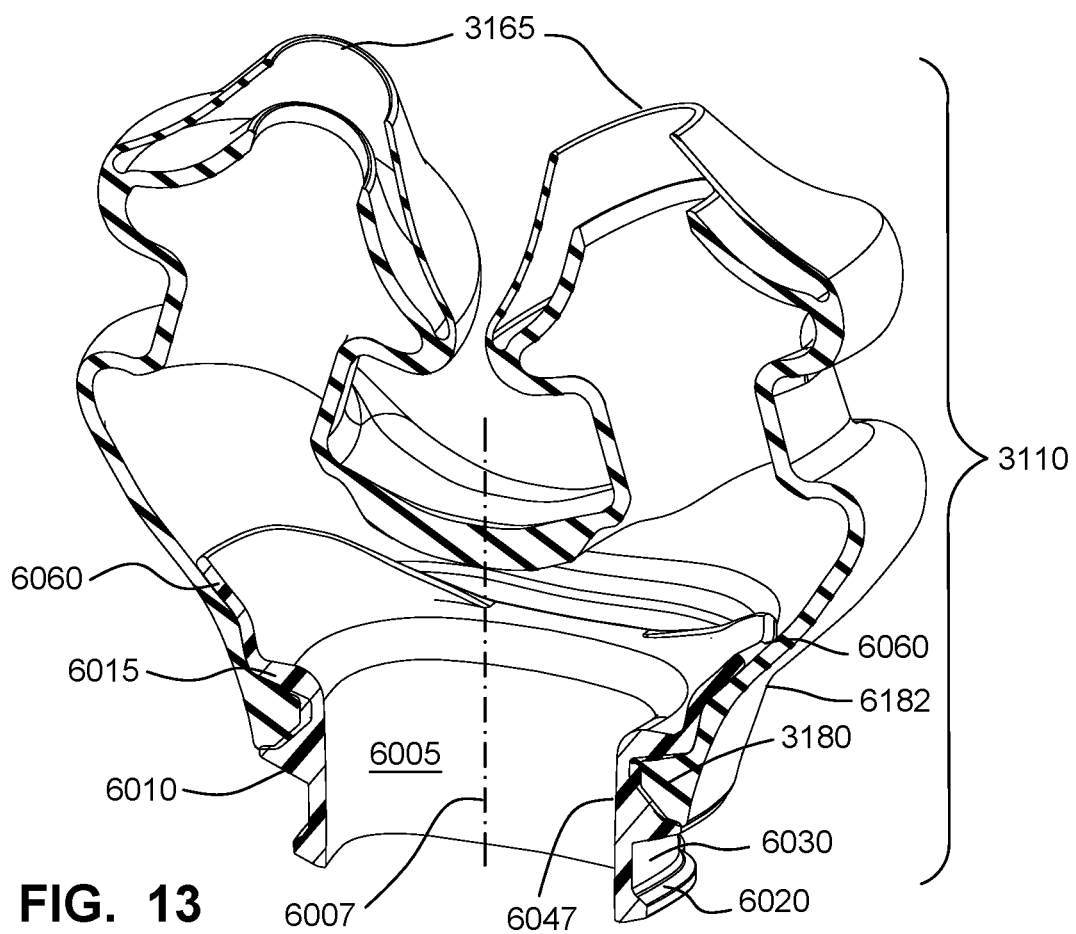

FIG. 13 shows a cross-sectional view of a nasal pillow module in accordance with another aspect of the technology.

Figure 14:
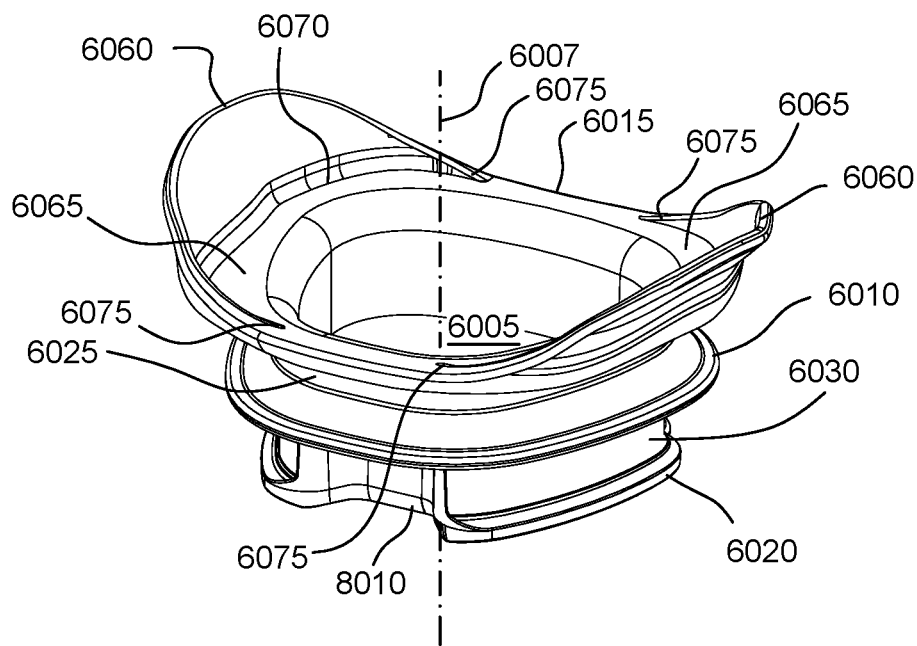
Figure 15:
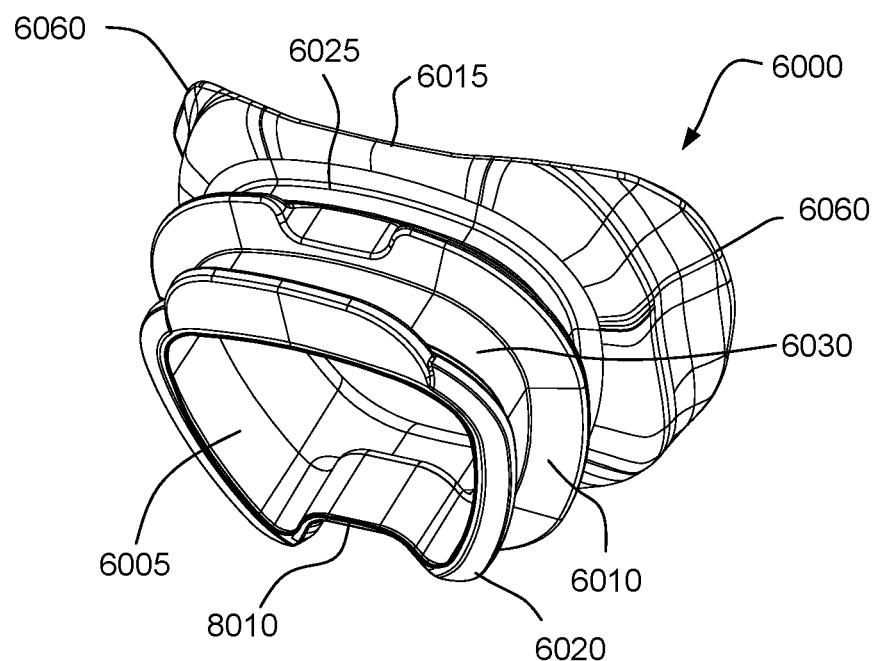
Figure 16:
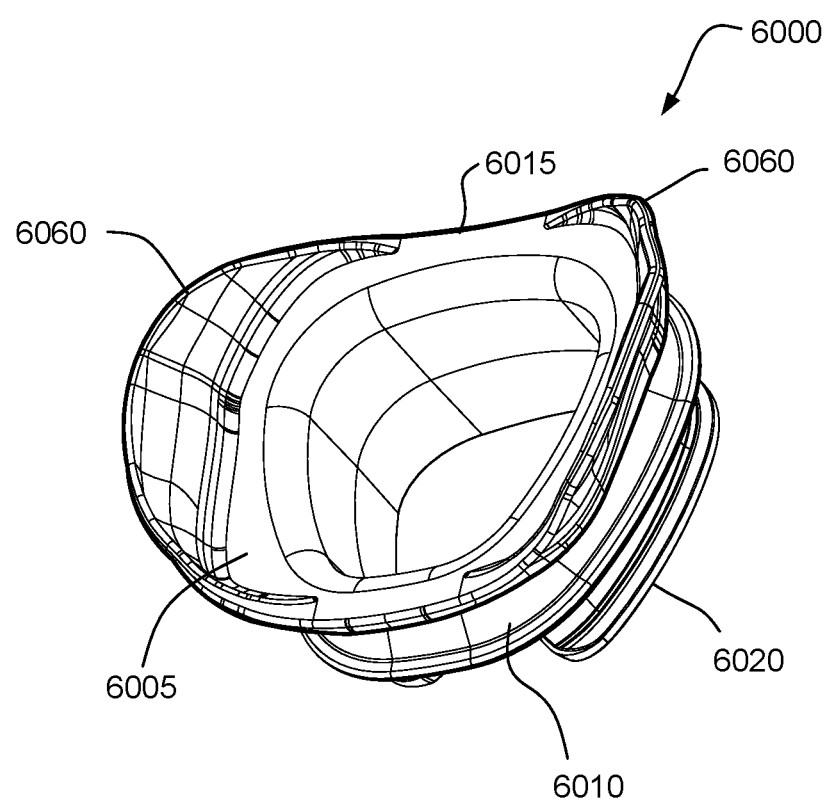

FIGS. 14-16 show different views of another exemplary cushion clip.

Figure 17:
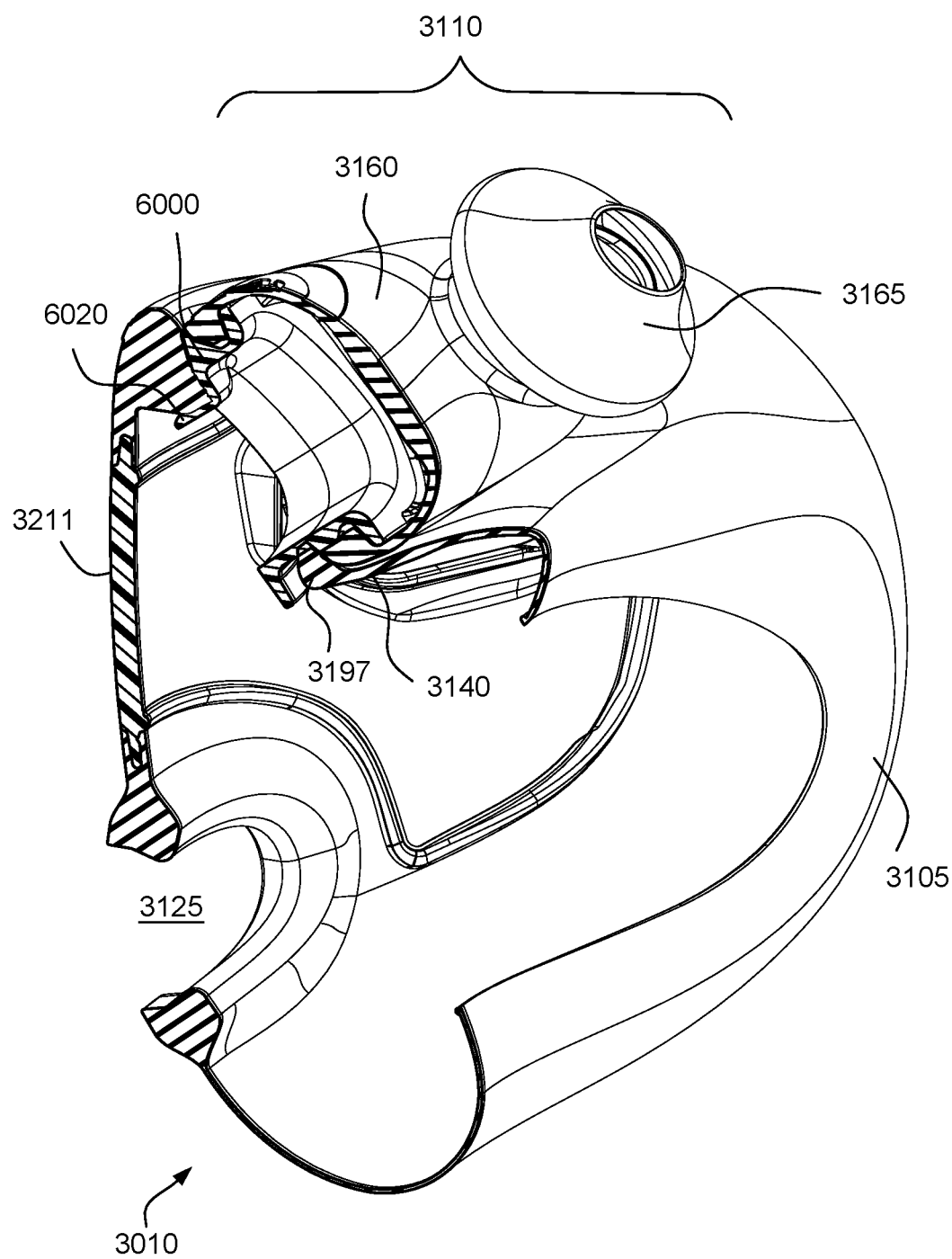

FIG. 17 shows a cross-sectional view of the main body of the patient interface.

Figure 18:
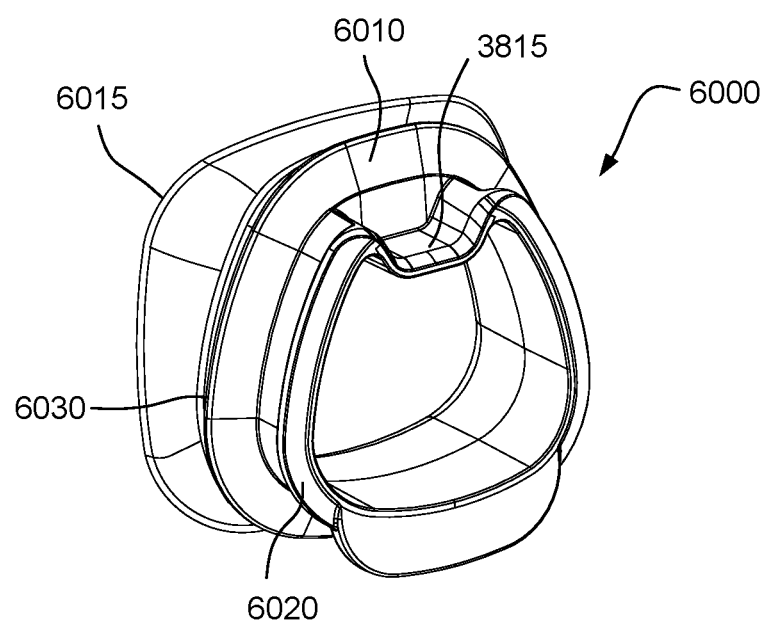

FIG. 18 shows another view of the cushion clip.

Figure 19:
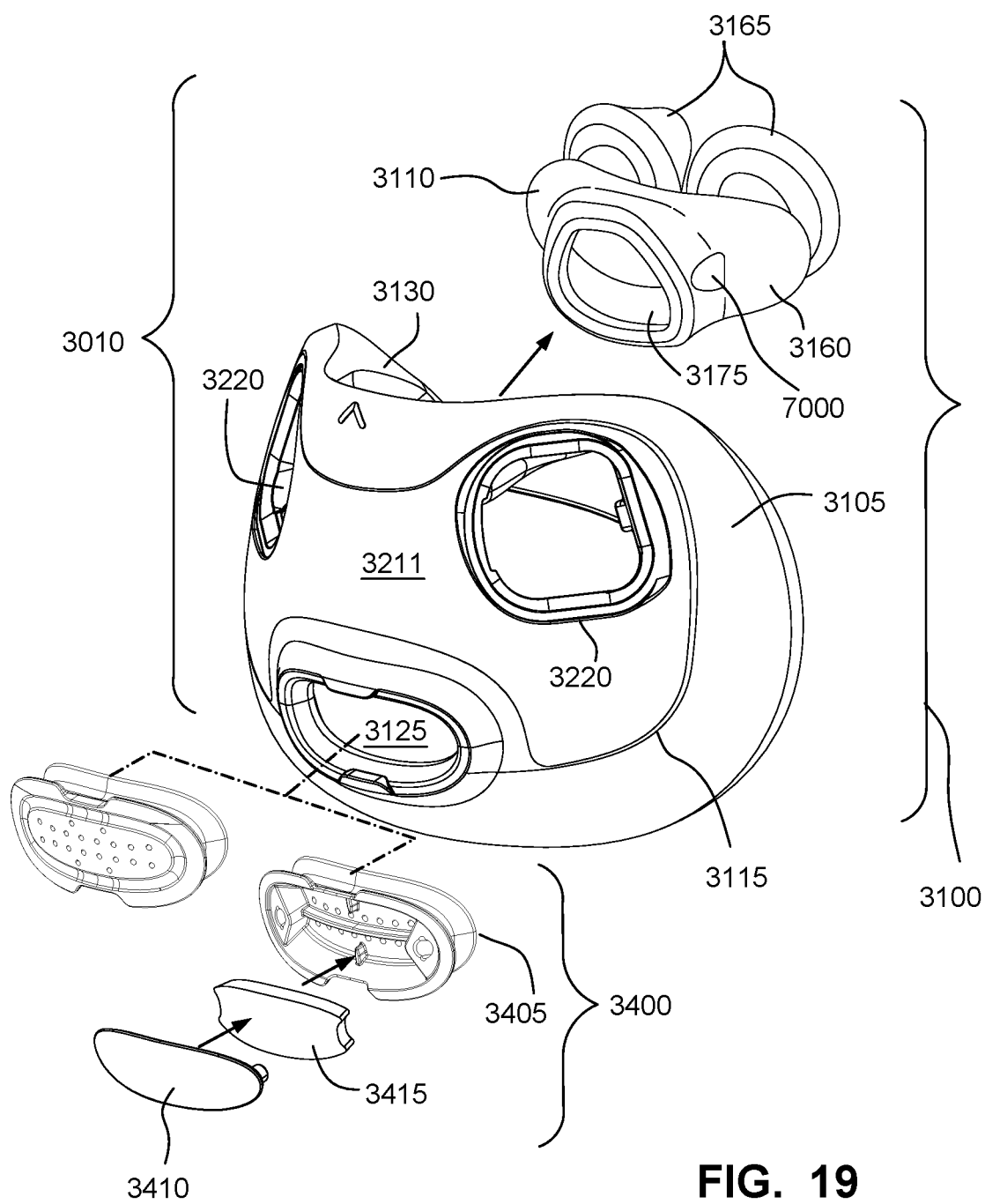

FIG. 19 shows an exploded view of another exemplary patient interface.

Figure 20:
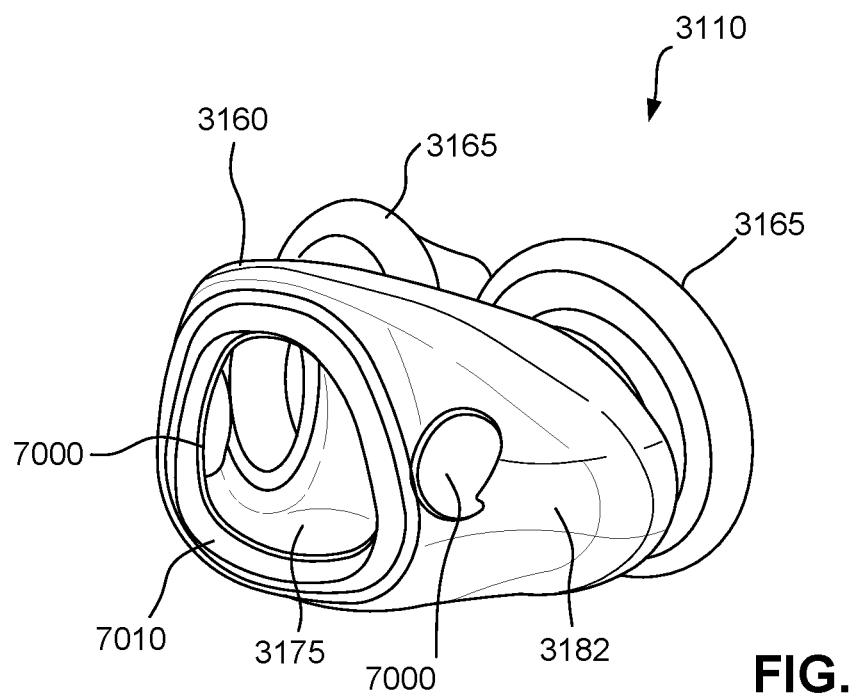

FIG. 20 shows a nasal pillow module according to another aspect of the technology.

Figure 21:
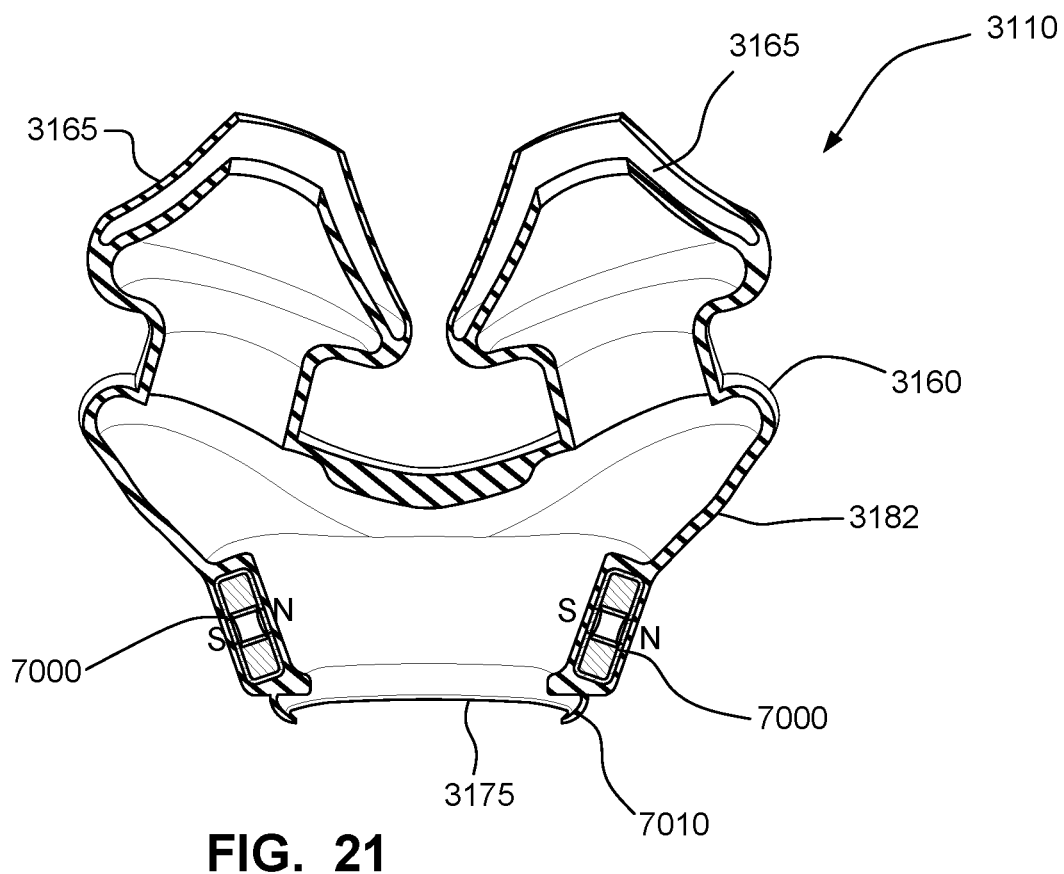

FIG. 21 shows another view of the nasal pillow module of FIG. 20.

Figure 22:
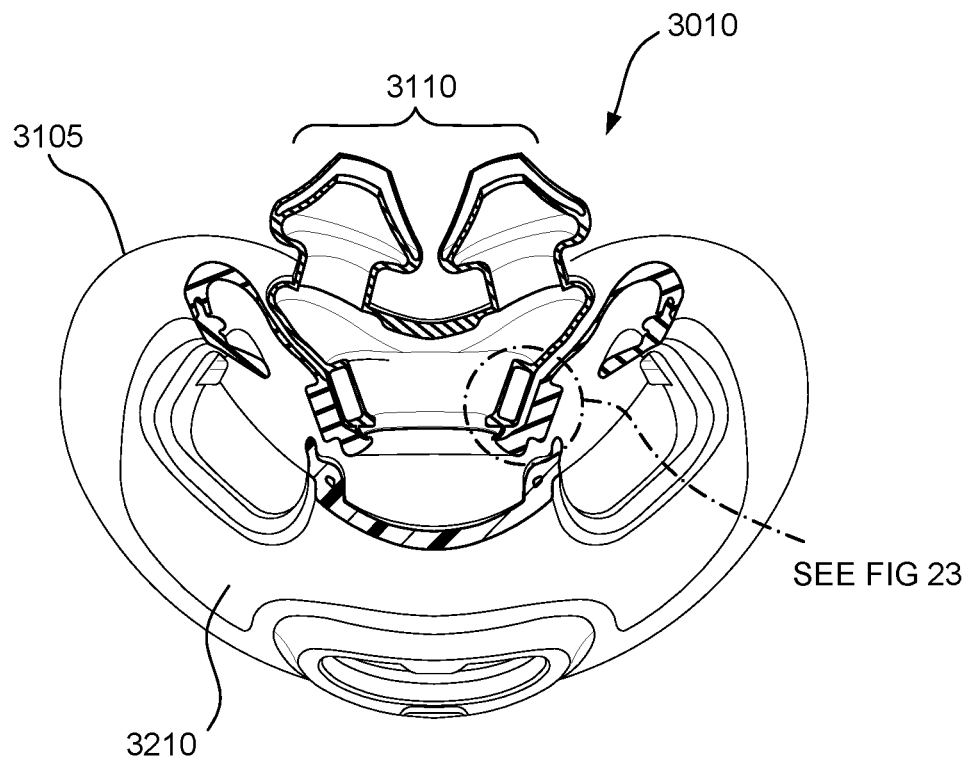

FIG. 22 shows a cross-sectional view of the patient interface of FIG. 19.

Figure 23:
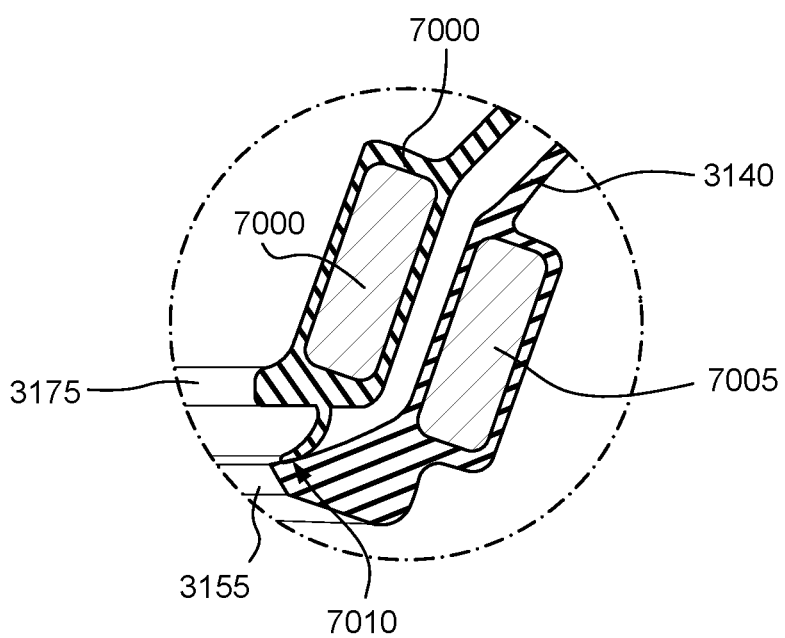

FIG. 23 shows an enlarged view of the connection between the nasal module and the mouth cushion.

Figure 24:
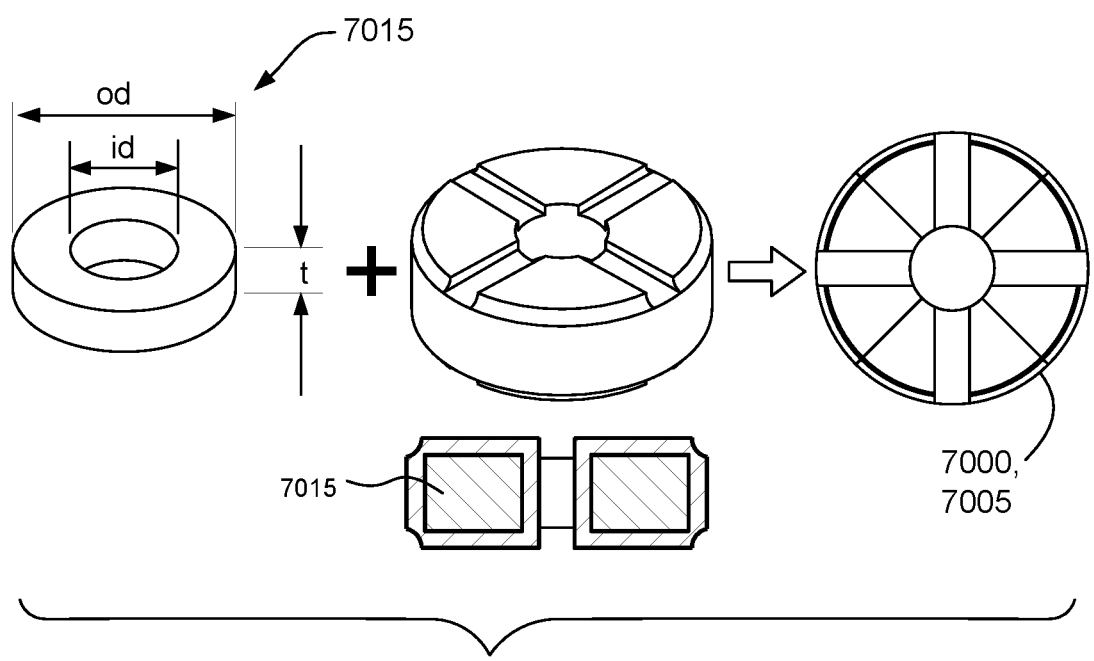

FIG. 24 shows an exemplary magnet according to an aspect of the present technology.

Figure 25:
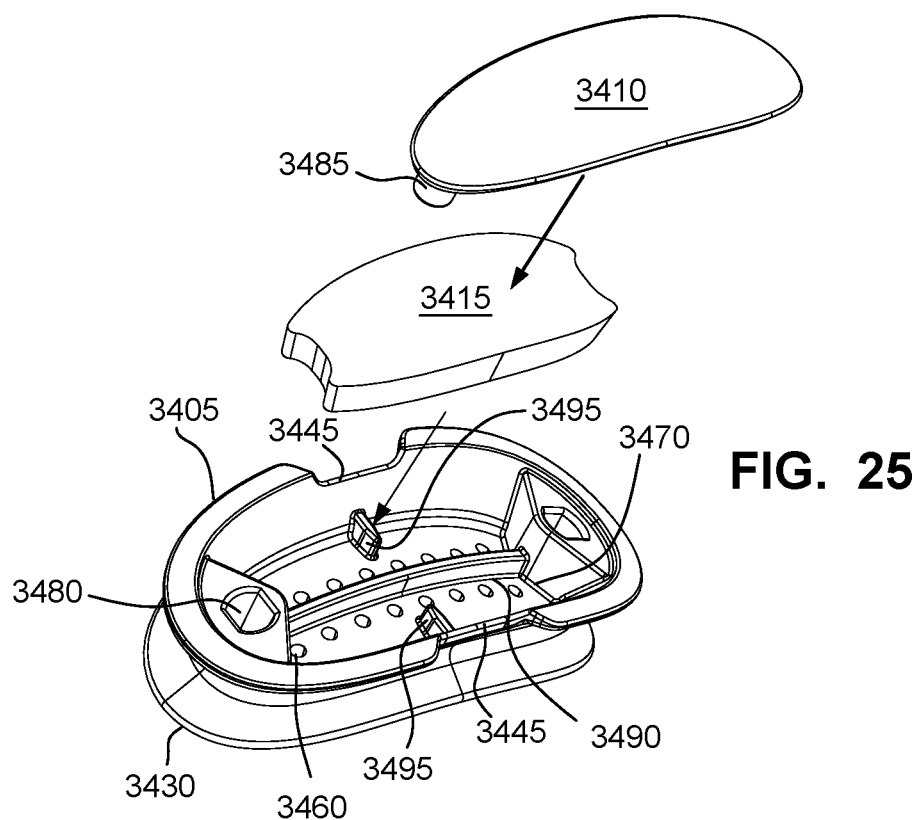

FIG. 25 shows an exploded view of an exemplary vent assembly.

Figure 26:
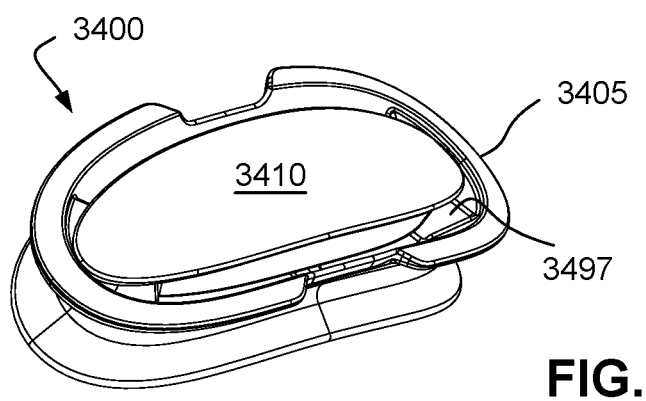

FIG. 26 shows the vent assembly of FIG. 25 in assembled form.

Figure 27:
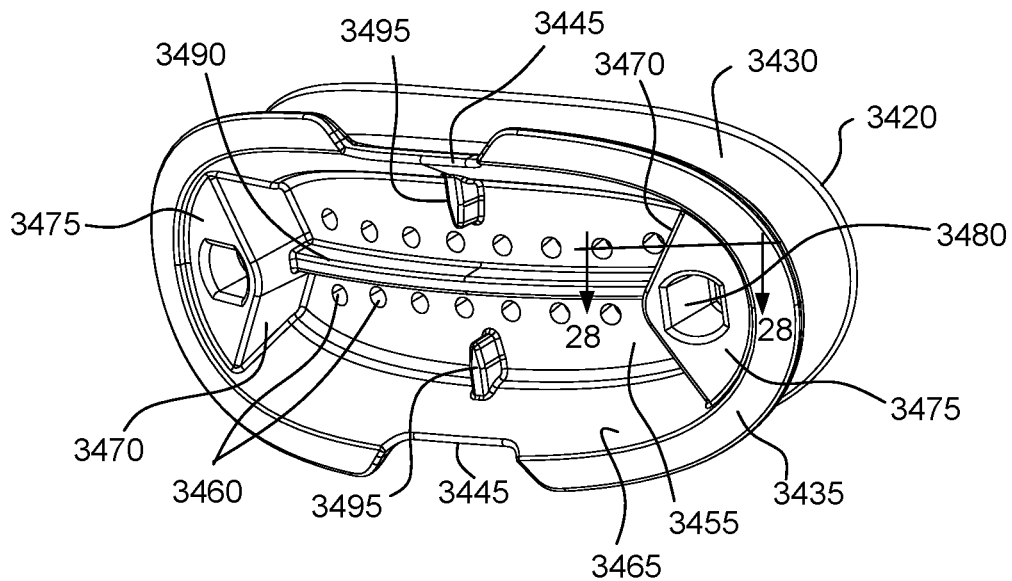

FIG. 27 shows a main body of the vent assembly of FIG. 25.

Figure 28:
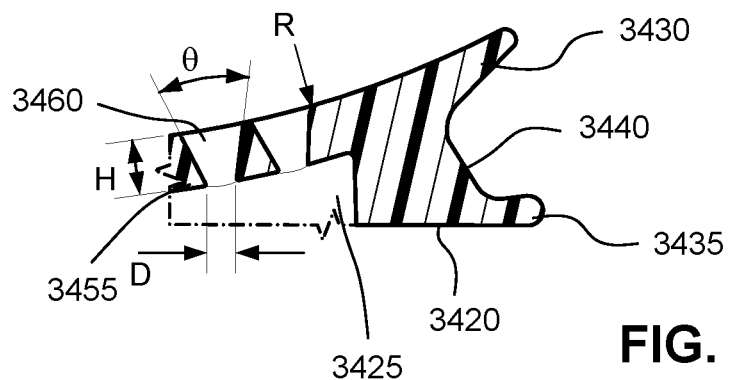

FIG. 28 shows a cross-sectional view of the main body of FIG. 27.

Figure 29:
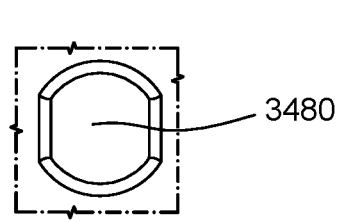
Figure 30:
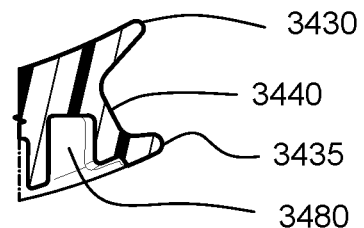

FIGS. 29 and 30 show detailed views of an anchor receptacle of the vent assembly.

Figure 31:
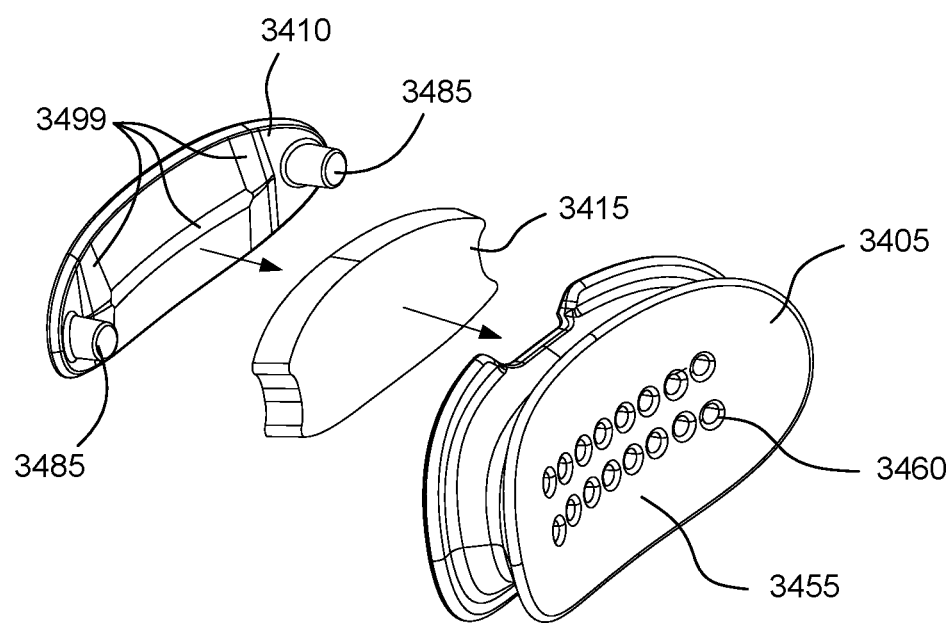

FIG. 31 shows another exploded view of the vent assembly of FIG. 25.

Figure 32:
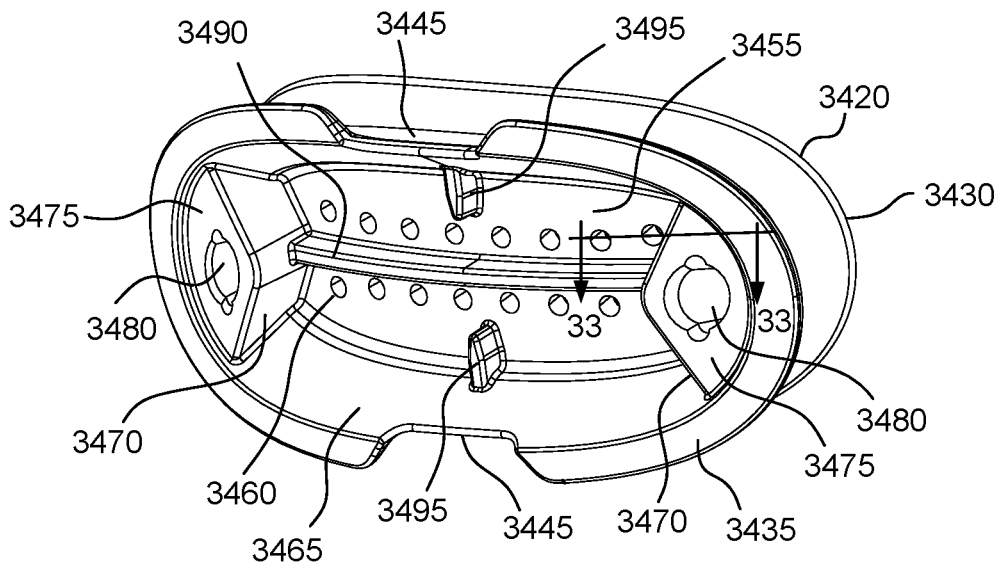

FIG. 32 shows a main body of a vent assembly according to another aspect of the technology.

Figure 33:
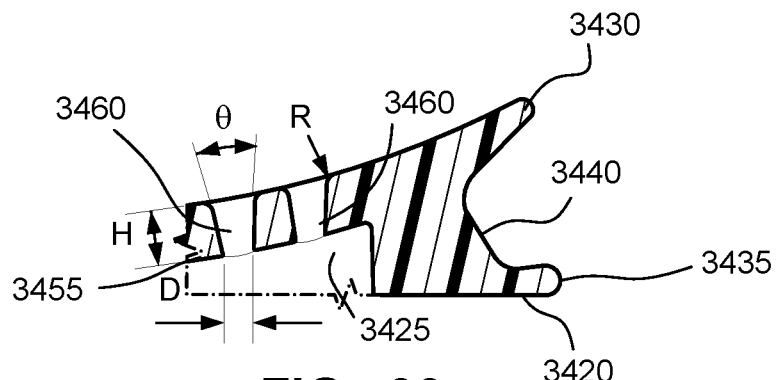

FIG. 33 shows a cross-sectional view of the main body of FIG. 32.

Figure 34:
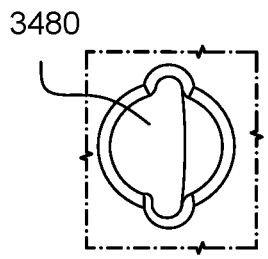
Figure 35:
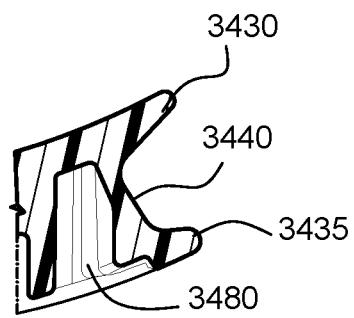

FIGS. 34 and 35 show detailed view of an anchor receptacle of the vent assembly.

Figure 36:
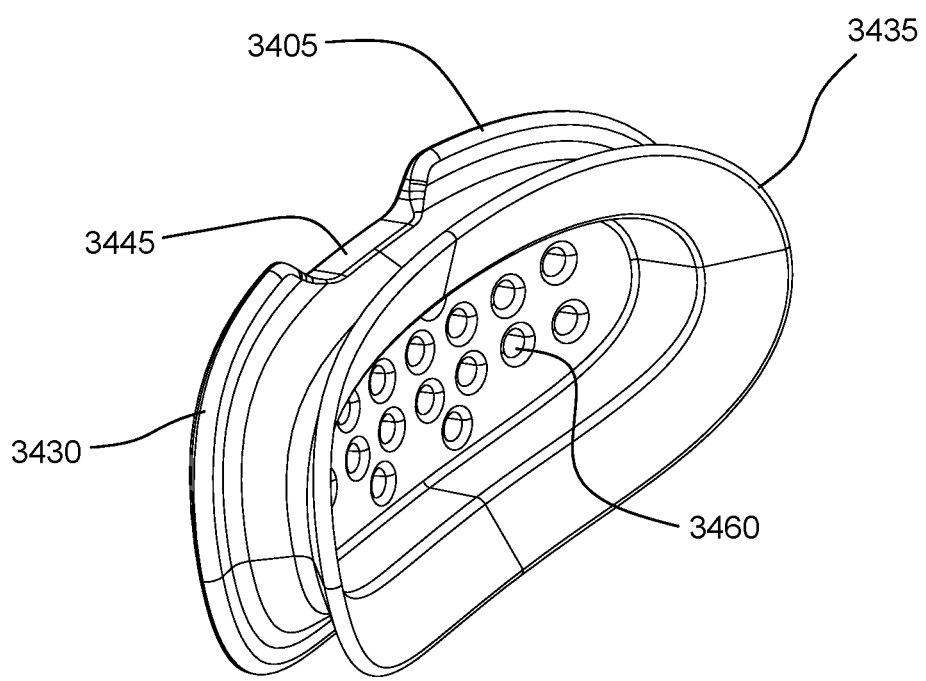

FIG. 36 shows a rear view of a vent according to another aspect of the present technology.

Figure 37:
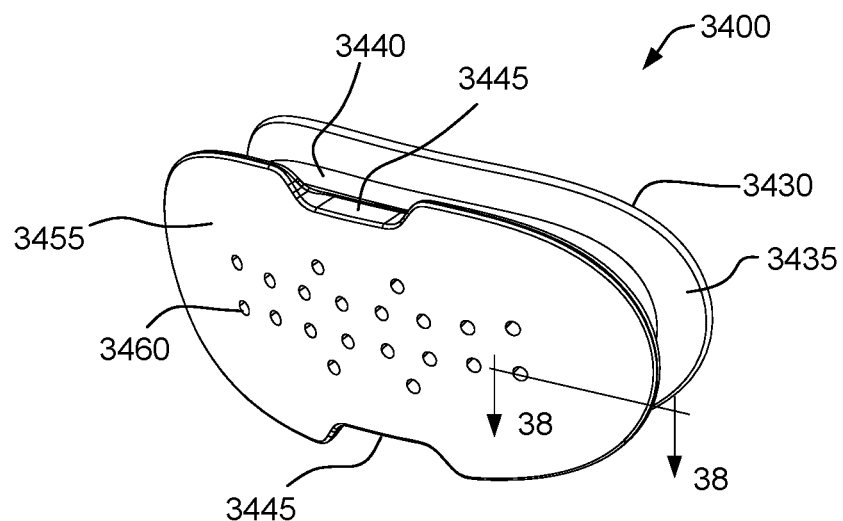

FIG. 37 shows another view of the vent of FIG. 36.

Figure 38:
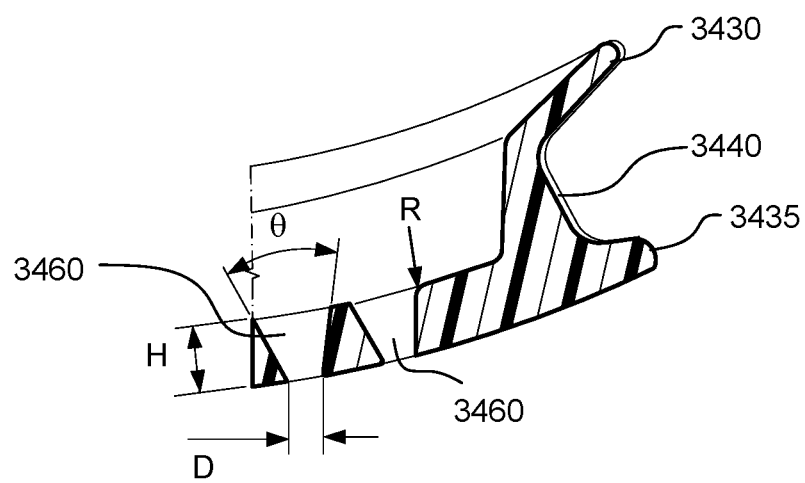

FIG. 38 shows a cross-sectional view of the vent of FIG. 36.

Figure 39:
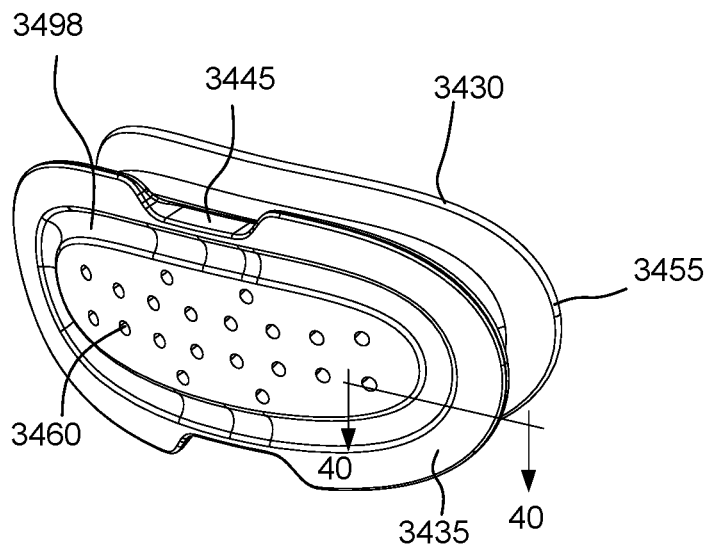

FIG. 39 shows a vent according to another aspect of the present technology.

Figure 40:
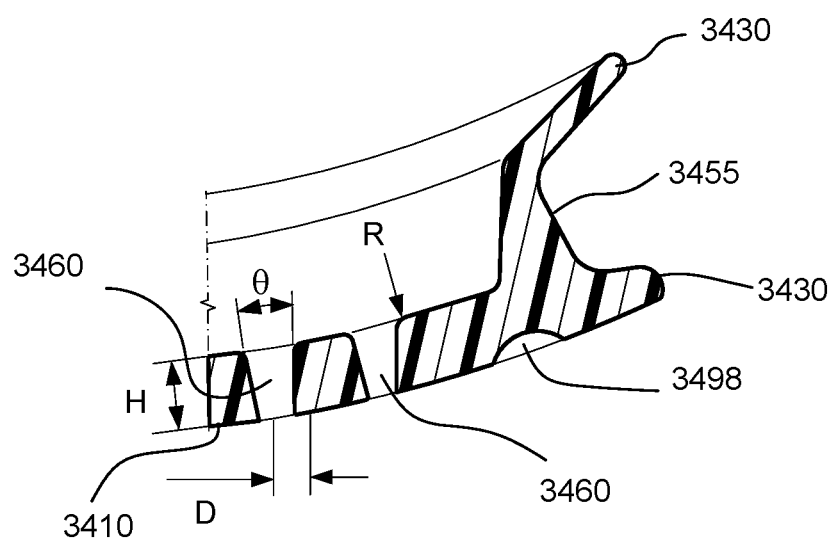

FIG. 40 shows a cross-sectional view of the vent of FIG. 39.

4 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

4.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and (optionally) a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

An unsealed patient interface 3800, in the form of a nasal cannula, includes nasal prongs 3810a, 3810b which can deliver air to respective nares of the patient 1000 via respective orifices in their tips. Such nasal prongs do not generally form a seal with the inner or outer skin surface of the nares. This type of interface results in one or more gaps that are present in use by design (intentional) but they are typically not fixed in size such that they may vary unpredictably by movement during use. This can present a complex pneumatic variable for a respiratory therapy system when pneumatic control and/or assessment is implemented, unlike other types of mask-based respiratory therapy systems. The air to the nasal prongs may be delivered by one or more air supply lumens 3820a, 3820b that are coupled with the nasal cannula-type unsealed patient interface 3800. The lumens 3820a, 3820b lead from the nasal cannula-type unsealed patient interface 3800 to a respiratory therapy device via an air circuit. The unsealed patient interface 3800 is particularly suitable for delivery of flow therapies, in which the RPT device generates the flow of air at controlled flow rates rather than controlled pressures. The "vent" or gap at the unsealed patient interface 3800, through which excess airflow escapes to ambient, is the passage between the end of the prongs 3810a and 3810b of the nasal cannula-type unsealed patient interface 3800 via the patient's nares to atmosphere.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH2O with respect to ambient.

The patient interface 3000 in accordance with one form of the present technology is constructed and arranged to be able to provide a supply of air at a positive pressure of at least 10 cmH2O with respect to ambient.

The patient interface 3000 in accordance with one form of the present technology is constructed and arranged to be able to provide a supply of air at a positive pressure of at least 20 cmH2O with respect to ambient.

4.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.1.2 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

4.3.1.3 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

4.3.1.4 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, a wall 3211 bounding at least part of the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the wall 3211 bounding at least part of the plenum chamber 3200 is constructed from a translucent material. The use of a translucent material can reduce the obtrusiveness of the patient interface, and help improve compliance with therapy.

4.3.3 Main Body

FIG. 6 shows an exemplary patient interface 3000 according to one aspect of the technology. As can be seen, the patient interface comprises a main body 3010 and a positioning and stabilising structure 3300 that supports the main body 3010. It should be understood that the patient interface 3000 may also be referred to as a patient interface assembly. When the patient interface 3000 is referred to as a patient interface assembly, the main body 3010 may be referred to as a patient interface.

Looking at FIG. 7, the main body 3010 may comprise the seal-forming structure 3100 and the wall 3211 bounding the plenum chamber 3200. It is contemplated that the main body 3010 may also be referred to as a core body of the patient interface 3000. The main body 3010 may also be referred to as a cushion and shell assembly, cushion and frame assembly, or cushion/frame with the seal-forming structure 3100 forming the cushion portion and the wall 3211 forming the shell or frame portion. It is contemplated that the wall 3211 may also be referred to as a frame or a shell.

The wall 3211 may form at least part of an anterior side of the plenum 3200. In addition, the positioning and stabilising structure 3300 may be connected to the main body 3010 at the wall 3211. In particular, the wall 3211 may include a pair of upper headgear connectors 3221 and a pair of lower headgear connectors 3231 that are positioned at a location that is inferior to the upper headgear connectors 3221.

The upper headgear connectors 3221 may be located on opposing lateral sides of the center of the main body 3010. In addition, the upper headgear connectors 3221 may be configured to connect to corresponding upper headgear straps and/or conduits of the positioning and stabilizing structure 3300. The upper headgear connectors 3221 may be in the form of openings in the wall 3211 and may function as gas or air inlets to the plenum 3200. In other words, pressurized respiratory gas from the RPT device 4000 may enter the main body 3010 by way of the upper headgear connectors 3221. In addition, the upper headgear connectors 3221 may form part of a magnetic connection and/or mechanical connection with the corresponding upper headgear strap and/or conduit.

The lower headgear connectors 3231 may be located on opposing lateral sides of the center of the main body 3010. In addition, the lower headgear connectors may be configured to corresponding lower headgear straps and/or conduits of the positioning and stabilizing structure 3300. The lower headgear connectors 3231 may have a different structure and may connect differently to the positioning and stabilizing structure 3300 than the upper headgear connectors 3221. The lower headgear connectors 3231 may form part of a magnetic connection and/or a mechanical connection with the corresponding lower headgear strap and/or conduit. In addition, it is contemplated that the lower headgear connectors 3231 may be rotatable and/or resiliently flexible. In addition, although the lower headgear connectors 3231 are illustrated as being components on the wall 3211 (see FIGS. 6 and 7), it is contemplated that the lower headgear connectors 3231 may be openings in the wall 3211.

In some configurations, either the upper headgear connectors 3221 or the lower headgear connectors 3231 may be omitted. In configurations with only the lower headgear connectors 3231, the lower headgear connectors 3231 may be openings in the wall 3211 that function as air/gas inlets into the plenum 3200. It is also contemplated that the structures of the upper headgear connectors 3221 and the lower headgear connectors 3231 may be swapped. That is the lower headgear connectors 3231 may be openings in the wall 3211, and the upper headgear connectors 3221 may be located on the wall 3211.

It is contemplated that the wall 3211 may have any number of shapes. One exemplary shape is illustrated in FIGS. 6 and 7. The exemplary shape of the wall 3211 of FIGS. 6 and 7 has inferior and superior sides that are further apart at the lateral sides than at the central portion. It is further contemplated that the wall 3211 may be curved so that an interior side of the wall 3211 (i.e., the side facing the plenum 3200) is concave while an exterior side of the wall 3211 (i.e., the side facing away from the plenum 3200) is convex. Accordingly, the entire exterior surface of the wall 3211 may be dome-shaped.

The seal-forming structure 3100 may be in the form of a flexible oro-nasal cushion that may comprise a mouth (or oral) portion 3105 configured to seal around the patient's mouth and may comprise a nasal portion 3110 configured to seal the patient's nares.

The mouth portion 3105 may cooperate with the wall 3211 to form the plenum 3200. In addition, the mouth portion 3105 may comprise a first opening 3115 that receives the wall 3211. The inferior and superior sides of the first opening 3115 may be further apart at the lateral sides than at the central portion. The wall 3211 may be secured to the mouth portion 3105 by a sonic weld, an adhesive, a mechanical bond, or mechanical fasteners. It is further contemplated that the wall 3211 may be molded to the mouth portion 3105.

The mouth portion 3105 may include a continuous target seal-forming region around the patient's mouth that is configured to engage the patient's upper lip and the patient's chin. The mouth portion 3105 may include a sealing flap on a posterior side that forms a rim around a second opening 3120 (see FIG. 8). The second opening 3120 may be positioned so that pressurized respiratory gas flowing through the second opening 3120 is directly discharged into the patient's mouth in use.

In addition, it is contemplated that the sealing flap may be saddle shaped in the regions intersected by a plane that bisects the main body 3010 into right and left sides (or the patient's sagittal plane) may be saddle shaped. That is both the central superior and central inferior sides of the sealing flap may be saddle shaped. In addition, each of the saddle shaped portions of the sealing flap may be positioned between dome shaped regions. Also, lateral sides of the sealing flap may have a cylindrical shape and may be positioned between opposing dome shaped regions.

It is contemplated that the mouth portion 3105 may include a third opening 3125 configured to receive a vent assembly 3400. The third opening 3125 may be located on an anterior facing side of the mouth portion 3105. The vent assembly 3400 will be described in more detail, later. It is contemplated that the surface of the mouth portion 3105 around the third opening may be dome shaped.

A superior (or upper) surface of the mouth portion 3105 may form a receptacle 3130 configured to receive the nasal portion 3110. The receptacle 3130 may be in the form of a recess in the mouth portion 3105 and may be referred to as any type of recess such as, for example, a pocket, an indentation, a bowl, a socket, a basin, a trough.

The receptacle 3130 may comprise a base 3135 at a base of the receptacle 3130 and at least one side wall 3140 extending from the base 3135, the at least one side wall 3140 terminating at an outer rim 3145 of the receptacle 3130. The base 3135 and the at least one side wall 3140 may form a receiving space 3150 that receives the nasal portion 3110. The receiving space 3150 may be shaped so that a perimeter of the receptacle 3130 at the outer rim 3145 is larger than the perimeter of the receptacle 3130 at the base 3135. In addition, the receiving space 3150 may be separated from the plenum 3200 by the base 3135 and the at least one side wall 3140. Also, a fourth opening 3155 of the mouth portion 3105 may be located in the base 3135. Pressurized respiratory gas in the plenum 3200 may be discharged through the fourth opening 3155 to the nasal portion 3110.

FIG. 8 illustrates the fourth opening 3155 being substantially trapezoidal shaped. However, the fourth opening 3155 may have any shape that allows the flow of pressurized respiratory gas to be discharged from the plenum 3200. In addition, it is contemplated that the rim around the fourth opening 3155 may be saddle shaped, while the outer rim 3145 may include alternating cylinder and dome shaped regions. A trough may be formed between the saddle shaped rim and the dome and cylinder shaped outer rim. Alternatively, the base 3135 of the receptacle 3130 may be flat and/or planar so that the receptacle 3130 does not have a trough. The shape of the receptacle 3130 may allow the nasal portion 3110 to be positioned closer to a central part of the main body 3010 to form a more compact structure when the nasal portion 3110 is secured to the mouth portion 3105.

It is contemplated that the wall 3211 (or shell) may extend over a superior side of the mouth portion 3105 so that the wall 3211 forms the receptacle 3130 and includes the fourth opening 3155. The shapes described above would also apply to a fourth opening 3155 and receptacle 3130 formed by the wall 3211.

The nasal portion 3110 may comprise a nasal base 3160 and a pair of nasal pillows 3165 extending from the nasal base 3160. The nasal base 3160 may be a hollow body that forms a nasal plenum 3170. In addition, at least part of the nasal base 3160 may have a shape that is complementary to the shape of the at least one side wall 3140 of the receptacle 3130. It is contemplated that the nasal base 3160 may be constructed from a soft, flexible, resilient material such as, for example, silicone. As such, the nasal base 3160 may be configured to conform to the shape of the at least one side wall 3140 of the receptacle 3130 when the nasal base 3160 is received within the receptacle 3130.

The central portions of the nasal base 3160 (including the portion between the nasal pillows 3165) may have a saddle shape. In addition, the lateral sides of the nasal base 3160 may be dome shaped.

An inlet opening 3175 may be located on a side of the nasal base 3160 that is opposite the nasal pillows 3165. It is contemplated that the inlet opening 3175 may have a similar or the same shape and size as the fourth opening 3155 in the mouth portion 3105. In addition, the inlet opening 3175 may be aligned with the fourth opening 3155 when the nasal portion 3110 is secured to the mouth portion 3105 so that pressurized respiratory gas in the plenum 3200 may flow through the fourth opening 3155 to the inlet opening 3175 and into the nasal plenum 3170. Also, the surface of the nasal base 3160 around the inlet opening 3175 may be planar or flat.

The pair of nasal pillows 3165 may form a seal with an interior of the patient's nares and/or an underside of the patient's nose. In addition, the pair of nasal pillows 3165 may be integrally formed with the nasal base 3160. Alternatively, each nasal pillow 3165 may be removable from the nasal base 3160. In yet another alternative configuration, the nasal pillows 3165 may be removable from the nasal base 3160 as a unit.

The nasal pillows 3165 may include openings through which the pressurized respiratory gas may be discharged into the patient's nasal passages. The surface (rim) around the openings in the nasal pillows 3165 may be saddle shaped. Also, it is contemplated that the nasal pillows may have a double wall structure (as illustrated in FIGS. 9, 13, 21, and 22) or a single wall structure (not shown).

The nasal portion 3110 may be secured to the mouth portion 3105 by any number of methods. For example, the nasal portion 3110 may be secured to the mouth portion 3105 by way of a clip or a magnetic connection.

4.3.3.1 Clip Connection

In one aspect of the technology illustrated in FIGS. 9-18, the nasal portion 3110 may be secured to the mouth portion 3105 by way of a clip (or cushion clip) 6000. The clip 6000 may be in the form of a tubular structure that is open at both ends. The clip 6000 may have a lumen (or bore) 6005 extending from one end to the other and forming a gas flow path through the clip 6000. The lumen may have a central longitudinal axis 6007. In addition, the clip may be formed from a rigid and/or molded material such, for example, plastic. Alternatively, the clip 6000 may be formed from a flexible material such as, for example, silicone.

The clip 6000 may be secured to the nasal base 3160 by way of an interference fit in which structures on the clip 6000 and the nasal base 3160 may interlock. For example, a portion of the clip 6000 may be inserted inside the nasal base 3160 so that one or more features on the outer surface of the clip 6000 may interlock with one or more features on an interior surface of the nasal base 3160. It is contemplated that the clip 6000 may be secured to the nasal base 3160 by any other method such as, for example, a threaded connection, a bayonet connection, a magnetic connection, a snap-fit connection, etc. The clip 6000 may also be secured to the nasal base 3160 by any combination of the connection types listed above. In addition, for configurations in which the clip 6000 is permanently attached to the nasal base 3160, the clip 6000 may be attached to the nasal base 3160 by way of adhesive, chemical bonding, co-molding, or any other permanent connection method.

It is contemplated that in some configurations a rim of the inlet opening 3175 of the nasal base 3160 may form part of the interference fit and may be in the form of an inwardly projecting flange (or lip) 3180. The flange 3180 may be tapered toward a free end of the flange 3180 so that the flange 3180 is thickest closest to its base at a side wall 3182 and is thinnest at its free end.

In addition, as can be seen in FIG. 9A, the flange 3180 may have an asymmetrical cross-sectional shape. In particular, the flange 3180 may have a first side 3185 facing toward the nasal pillows 3165 and a second side 3190 facing away from the nasal pillows 3165. The first side 3185 may form a first angle α with a line 3195 that extends through the furthest extent of the flange 3180 and is perpendicular with the side wall 3182. The second side 3190 may form a second angle β with the line 3195. The angle α may be smaller than the angle β so that the taper of the second side 3190 is greater than the taper of the first side 3185.

The clip 6000 may be bisected by a middle flange 6010 on an exterior surface of the clip 6000 that extends radially away from the lumen 6005 and around a perimeter of the clip 6000. In addition, the clip 6000 may comprise a first end flange (or nasal end flange) 6015 on one side of the middle flange 6010 and a second end flange (or mouth end flange) 6020 on the other side of the middle flange 6010. The middle flange 6010 and the first end flange 6015 together may form a first channel (or first groove or first trench) 6025 configured to receive the flange 3180 of the nasal base 3160. In addition, the middle flange 6010 and the second end flange 6020 together may form a second channel (or second groove or second trench) 6030 configured to receive a part of the receptacle 3130.

The middle flange 6010 may be a continuous structure that fully encircles the lumen 6005. Alternatively, the middle flange 6010 may be a discontinuous structure and/or may extend only partly around the lumen 6005 (e.g., partially encircle the lumen 6005). In addition, the middle flange 6010 may be tapered toward a free end of the middle flange 6010. Accordingly, the middle flange 6010 may be thickest closest to the lumen 6005 and may be thinnest at its free end.

As can be seen in FIG. 9B, the middle flange 6010 may have an asymmetrical cross-sectional shape. In particular, the middle flange 6010 may have a first side (or nasal portion facing side) 6035 forming part of the first channel 6025. The middle flange 6010 may have a second side (or mouth portion facing side) 6040 forming part of the second channel 6030. The first side 6035 may form an angle γ with a line 6045 that extends through the free end of the middle flange 6010 and is perpendicular with a side wall 6047 of the lumen 6005. The second side 6040 may form an angle δ with the line 6045. The angle γ may be greater than the angle δ so that the taper of the first side 6035 is greater than the taper of the second side 6040.

Similar to the middle flange 6010, the first end flange 6015 may also be tapered (FIG. 9C). In particular, a channel side 6050 of the first end flange 6015 may form an angle φ with a line 6055 that extends through the furthest extend of the first end flange 6015 and is perpendicular with the side wall 6047. The angle of taper for the channel side 6050 may match the angle of taper of the first side 3185 of the flange 3180. In addition, the angle of taper of the first side 6035 of the middle flange 6010 may match the angle of taper of the second side 3190 of the flange 3180. That way, the shape of the first channel 6025 of the clip 6000 may be complimentary to the shape of the flange 3180.

When the clip 6000 is inserted into the nasal base 3160 to connect the clip 6000 to the nasal base 3160, the flange 3180 may be received within the first channel 6025. Because the shape of the first channel 6025 may be complimentary to the shape of the flange 3180, the flange 3180 may form an air-tight seal with the first end flange 6015 and the middle flange 6010. In addition, the flange 3180 may resist movement of the clip 6000 relative to the nasal base 3160 along the central longitudinal axis 6007 (i.e., axial movement of the clip 6000).

It should be understood that the asymmetrical cross-section of the flange 3180 allows the clip 6000 to be pushed into the nasal base 3160 with less force than is necessary to remove the clip 6000 from the nasal base 3160. In other words, the flange 3180 may provide more resistance to the removal of the clip 6000 from the nasal base 3160 than the insertion of the clip 6000 into the nasal base 3160. In particular, the larger taper angle of the second side 3190 of the flange 3180 may offer less resistance to the insertion (inward movement) of the first end flange 6015 of the clip 6000 than the resistance offered by the first side 3185 to the removal (outward movement) of the first end flange 6015 of the clip 6000.

It is contemplated that the clip 6000 may optionally include a pair of wings (or extensions or supplemental flanges) 6060 that may enhance the retention force keeping the clip 6000 secured to the nasal base 3160. In one example, a form of the clip 6000 without the wings 6060 may have retention force between 10 and 12 N. In other words it may take at least 10 to 12 N to remove the clip 6000 without wings 6060 from the nasal base 3160. On the other hand, a form of the clip 6000 with wings 6060 may have a retention force between 19 and 20 N. In other words, it may take at least 19 to 20 N to remove the clip 6000 with wings 6060 from the nasal base 3160. Thus, in the example provided above, the wings 6060 increased the retention force keeping the clip 6000 secured to the nasal base 3160 by as much as 100% (i.e., doubled the retention force).

As can be seen in FIG. 14, each wing 6060 may extend from the nasal pillow facing side 6065 of the first end flange 6015. In addition, the wings 6060 may be positioned on opposite lateral sides of the clip 6000 so that the lumen 6005 intervenes between the two wings 6060. The base 6070 of each wing 6060 may extend around one side of the lumen 6005 from an anterior side of the first end flange 6015 to a posterior side of the first end flange 6015. As a result, the ends 6075 of the base 6070 may be closest to the central longitudinal axis 6007 of the lumen 6005, while a middle part of the base 6070 may be furthest from the central longitudinal axis 6007 of the lumen 6005. In addition, the extent to which each wing 6060 projects from the first end flange 6015 may gradually increase from each end 6075 of the base 6070 to a maximum distance at a middle portion of the wing 6060.

Each wing 6060 may be oriented so that each wing 6060 extends from the first end flange 6015 in an axial and lateral direction so that each wing 6060 extends beyond the first end flange 6015 both laterally and axially. In addition, the outer surfaces of the wings 6060 may engage the lateral sides of the inner surface of the nasal plenum 3170. It is contemplated that the shape of the outer surfaces of the wings 6060 may be complimentary to the shape of the inner surface of the nasal plenum 3170. In addition, the wings 6060 may remain unfixed (i.e., movable) relative to the sides of the nasal plenum 3170 even after the clip 6000 is secured to the nasal plenum 3170. For example, the wings 6060 may slide along the inner surface of the nasal plenum 3170 if the nasal plenum 3170 is compressed and portions of the inner surface of the nasal plenum 3170 move or fold due to the compression of the nasal plenum 3170.

The wings 6060 may add rigidity and provide support to the lateral sides of the nasal plenum 3170 so that the lateral sides of the nasal plenum 3170 have more rigidity than the central anterior and posterior sides. The height of the wings 6060 as measured from the first end flange 6015 may increase toward the lateral sides of the clip 6000 and may decrease toward the central posterior and central anterior sides of the clip 6000 so that the maximum height may be at the furthest lateral extent of the wing 6060. It is contemplated that the increase in height may be gradual and may form a curved shape at an edge of the wing 6060. This way, the nasal plenum 3170 may be more flexible at the central region than at the lateral sides. By limiting the wings 6060 to the lateral sides of the nasal plenum 3170 and by varying the height of the wings 6060, the patient's comfort may be maintained while also strengthening the connection between the nasal portion 3110 and the clip 6000. In particular, if the wings 6060 were located toward the central portion of the nasal plenum 3170 or if the maximum height of the wings 6060 was located toward the central portion of the nasal plenum 3170, the wings 6060 would be more likely to press against the patient's upper lip or nose tip if the nasal plenum 3170 was compressed. However, since the wings 6060 are located on the lateral sides of the nasal plenum 3170, the wings 6060 are aligned on either side of the patient's nose and are less likely to press against any sensitive portion of the patient's face.

As illustrated in FIG. 17, the clip 6000 may similarly be secured to the mouth portion 3105 by way of an interference fit in which structures on the clip 6000 and the receptacle 3130 may interlock. For example, a portion of the clip 6000 may be inserted inside the plenum 3200 so that one or more features on the outer surface of the clip 6000 may interlock with one or more features on a surface of the receptacle 3130. It is contemplated that the clip 6000 may be secured to the mouth portion 3105 by any other method such as, for example, a threaded connection, a bayonet connection, a magnetic connection, a snap-fit connection, etc. Also, the clip 6000 may be secured to the mouth portion 3105 by any combination of the connection types listed above.

It is contemplated that in some configurations a rim of the fourth opening 3155 of the receptacle 3130 may form part of the interference fit and may be in the form of an inwardly projecting flange (or lip) 3197. The flange 3197 may be tapered toward a free end of the flange 3197 so that the flange 3197 is thickest closest to its base at the at least one side wall 3140 and is thinnest at its free end.

4.3.3.2 Magnetic Connection

In another aspect of the technology illustrated in FIGS. 19-23, the nasal portion 3110 may be secured to the mouth portion 3105 by way of a magnetic connection. The magnetic connection may be in the form of a pair of nasal module magnets 7000 located on the nasal base 3160 and a pair of receptacle magnets 7005 located in the receptacle 3130. Unlike the clip connection, the magnetic connection may eliminate a rigid body between the flexible bodies of the nasal portion 3110 and the mouth portion 3105. In other words, the magnetic connection may be a direct connection between flexible bodies.

As illustrated in FIGS. 20 and 21, the nasal module magnets 7000 may be located on opposing lateral sides of the nasal base 3160 so that the lumen 6005 intervenes between the nasal module magnets 7000. In addition, the nasal module magnets 7000 may be arranged so that one side of one magnet 7000 having a first polarity (i.e., north or south polarity) faces the general direction of the side of the other magnet 7000 having the opposite polarity. This will help position the nasal portion 3110 in the correct orientation when attached to the mouth portion 3105.

Also, the rim around the inlet opening 3175 may include a lip seal 7010 configured to sealingly engage the base 3135 of the receptacle 3130. It is contemplated that the nasal module magnets 7000 may be overmolded to the side wall 3182 of the nasal base 3160. Alternatively, the nasal module magnets 7000 may be secured to the nasal base 3160 by way of an adhesive, a mechanical fastener, or any other method that can secure the nasal module magnets 7000 to the nasal base 3160.

As illustrated in FIGS. 22 and 23, the receptacle magnets 7005 may be located on opposing lateral sides of the receptacle 3130 so that when the nasal portion 3110 is received within the receptacle 3130, the nasal base 3160 intervenes between the receptacle magnets 7005. In addition, similar to the nasal module magnets 7000, the receptacle magnets 7005 may be arranged so that one side of one magnet 7005 having a first polarity (i.e., north or south polarity) faces the general direction of the side of the other magnet 7005 having the opposite polarity. This will help position the nasal portion 3110 in the correct orientation when attached to the mouth portion 3105.

Also, the shape of the receiving space 3150 and the shape of the nasal base 3160 may be complimentary so that when the nasal base 3160 is received in the receiving space 3150 in the correct orientation, each nasal module magnet 7000 is automatically aligned with a corresponding one of the receptacle magnets 7005.

It is contemplated that the receptacle magnets 7005 may be overmolded to the at least one side wall 3140 of the receptacle 3130. Alternatively, the receptacle magnets 7005 may be secured to the mouth portion 3105 by way of an adhesive, a mechanical fastener, or any other method that can secure the receptacle magnets 7005 to the mouth portion 3105.

When the nasal base 3160 is fully received within the receptacle 3130, the lip seal 7010 may engage with the rim of the fourth opening 3155 to form a seal. The lip seal 7010 may be below the nasal module magnets 7000 and the receptacle magnets 7005 when the nasal base 3160 is fully received within the receptacle 3130. In addition, the nasal module magnets 7000 may be positioned between the receptacle magnets. It should be understood that the magnetic force between the nasal module magnets 7000 and the receptacle magnets 7005 may be sufficient to overcome the air pressure in the plenum 3200 and keep the lip seal 7010 in sealed engagement with the rim of the fourth opening 3155.

As illustrated in FIG. 24, the magnets 7000, 7005 may have a core 7015 in the form of a ring magnet. An outside diameter od of the core 7015 may be about 7 mm. An inner diameter id of the core 7015 may be about 2.5 mm. In addition, a thickness t of the core 7015 may be about 2 mm. Although the core 7015 is illustrated as a ring magnet, the core 7015 may have other shapes such as for example, a disc, a plate, or any other shape that allows for the sealed attachment of the nasal portion 3110 to the mouth portion 3105. In addition, the magnets 7000, 7005 may have a silicone rubber covering 7020 that is overmolded onto the core 7015. The silicone rubber covering 7020 may have a thickness of about 0.5 mm. It should be understood that the term "about" as used to describe the above dimensions allows for manufacturing tolerances.

It is contemplated that each of the nasal module magnets 7000 may have a different polarity. Similarly, each of the receptacle magnets 7005 may have a different polarity. Accordingly, if the nasal portion 3110 is inserted into the receptacle 3130 in the wrong orientation, a repellent magnetic force would prevent the nasal portion 3110 from being secured to the mouth portion 3105. It is contemplated that the magnets may be polarized and magnetized prior to or after being overmolded to the nasal portion 3110 or the mouth portion 3105.

4.3.3.3 Alignment Indicator

As illustrated in FIG. 6, the mouth portion 3105 may have a printed indicia 8000 located adjacent a rim of the receptacle 3130. At the same time, the nasal base 3160 may have a printed indicia 8005 positioned to align with the printed indicia 8000 when the nasal portion 3110 is correctly oriented within the receptacle 3130.

It is contemplated that the clip 6000 may have a keyed connection with the receptacle 3130. In particular, the clip 6000 may have an indentation or notch 8010 that is shaped complementary to a tab or rib 8015 located on a rim of the fourth opening 3155. The tab 8015 may prevent the clip 6000 from being secured to the receptacle 3130 if the nasal portion 3110 is positioned within the receptacle 3130 in the wrong orientation. Alternatively, the rib 8015 may be located on the clip 6000 and the indentation 8010 may be in the rim of the fourth opening 3155.

4.3.4 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another suitable for a small sized head, but not a large sized head.

4.3.4.1 Headgear Tubing

In some forms of the present technology, the positioning and stabilising structure 3300 comprises one or more tubes 3350 that deliver pressurised air received from a conduit forming part of the air circuit 4170 from the RPT device to the patient's airways, for example through the main body 3010. In the form of the present technology illustrated in FIG. 6, the positioning and stabilising structure 3300 may comprise two tubes 3350 that deliver air to the seal-forming structure 3100 from the air circuit 4170. The tubes 3350 may be an integral part of the positioning and stabilising structure 3300 of patient interface 3000 to position and stabilise the seal-forming structure 3100 of the patient interface to the appropriate part of the patient's face (for example, the nose and/or mouth). This may allow the conduit of air circuit 4170 to provide the flow of pressurised air to connect to a connection port 3600 of the patient interface in a position other than in front of the patient's face which may be unsightly to some people. While a pair of tubes 3350 have some advantages (described below), in some examples, the positioning and stabilising structure 3300 may comprise only a single tube 3350 configured to overlie the patient's head on one side. A strap or other stabilising component may be provided to the other side of the patient's head between the top end of the single tube 3350 and the seal-forming structure 3100, to provide balanced forces on the seal-forming structure 3100.

Since air can be contained and passed through headgear tubing 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIG. 6, the positioning and stabilising structure 3300 comprises the headgear tubing 3350, which is inflatable, and the straps 3310, which are not inflatable.

In certain forms of the present technology, the patient interface 3000 may comprise a connection port 3600 located proximal a top, side or rear portion of a patient's head. For example, in the form of the present technology illustrated in FIG. 6, the connection port 3600 is located on top of the patient's head. In this example the patient interface 3000 comprises an elbow 3610 to which the connection port 3600 is provided. The elbow 3610 may swivel with respect to the positioning and stabilising structure 3300 in order to decouple movement of a conduit connected to the connection port 3600 from the positioning and stabilising structure 3300. Additionally, or alternatively, a conduit connected to the connection port 3600 may swivel with respect to the elbow 3610. In the illustrated example, elbow 3610 comprises a swivelling conduit connector to which a conduit of the air circuit 4170 is able to connect such that the conduit can rotate about its longitudinal axis with respect to the elbow 3610.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the form of the present technology illustrated in FIG. 6, the positioning and stabilising structure 3300 comprises two tubes 3350, each tube 3350 being positioned in use on a different side of the patient's head and extending across the respective cheek region, above the respective ear (superior to the otobasion superior on the patient's head) to the elbow 3610 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the form of the technology shown in FIG. 6 the two tubes 3350 are fluidly connected at their upper ends to each other and to connection port 3600. In one embodiment, the two tubes are integrally formed while in other embodiments the tubes are separate components that are connected together in use and may be disconnected, for example for cleaning or storage. Where separate tubes are used they may be indirectly connected together, for example each may be connected to a T-shaped conduit having two conduit arms each fluidly connectable to the tubes 3350 and a third conduit arm or opening acting as the connection port 3600 and connectable in use to the air circuit 4170. The connection port 3600 may comprise an elbow 3610 received in fluid connection at the centre of two integrally formed tubes 3350.

The tubes 3350 may be formed of a semi-rigid material such as an elastomeric material, e.g. silicone. For example, the tubes 3350, from the left-side non-extendable tube section 3363 to the right side non-extendable tube section 3363, may be formed (e.g., by molding) from a single homogeneous piece of material, such as silicone. The tubes may have a natural, preformed shape and be able to be bent or moved into another shape if a force is applied to the tubes. For example, the tubes may be generally arcuate or curved in a shape approximating the contours of a patient's head between the top of the head and the nasal or oral region.

As described in U.S. Pat. No. 6,044,844, the contents of which are incorporated herein, the tubes 3350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 3350 during use. A crush resistant tube may be advantageous where only a single tube 3350 is present as if the single tube becomes blocked during use the flow of gas would be restricted and therapy will stop or reduce in efficacy.

In certain forms of the technology, one or more portions of the tubes 3350 may be rigidised by one or more rigidising or stiffening elements. Examples of rigidising elements include: sections of the tubes 3350 that are comparatively thicker than other sections; sections of the tubes 3350 that are formed from a material that is comparatively more rigid that the material forming other sections; and a rigid member attached to the inside, outside or embedded in a section of tube. The use of such rigidising elements helps to control how the positioning and stabilising structure 3300 will function in use, for example where the tubes 3350 is more likely to deform if forces are applied to them and where the shape of the tubes 3350 is more likely to be maintained if forces are applied. The selection of where such rigidising elements are positioned in the tubes 3350 can therefore help to promote comfort when the patient interface 3000 is worn and can help to maintain a good seal at the seal-forming structure 3100 during use. Rigidising or stiffening elements may be in positioning and stabilising structures 3300 which are configured to support relatively heavy seal-forming structures such as full face or oro-nasal cushion assemblies.

The tubes 3350 in the form of the technology shown in FIG. 6 have a length of between 15 and 30 cm each, for example between 20 and 27 cm each. In one example each of the tubes are around 26 cm long. In another example each of the tubes is around 23 cm long. The length of the tubes is selected to be appropriate for the dimensions of the heads of typical patients, for example the distance between the region proximate the top of the head where the upper end of the tubes 3350 are situated, and the region proximate the openings to the patient's airways at which the lower end of the tubes 3350 connect to the wall 3211 when following a generally arcuate path down the sides of the heads and across the patient's cheek region such as is shown in FIG. 6. As described in more detail below, the patient interface 3000 is configured so that the length of the tubes 3350 can be varied in some forms of the technology and the above lengths may apply to the tube in a contracted, stretched or neutral state. It will be appreciated that the length of the tubes 3350 will depend on the length of other components in the patient interface 3000, for example the length of arms of a T-shaped conduit to which the upper ends of tubes 3350 connect and/or the size of the plenum chamber 3200.

4.3.4.2 Headgear Straps

In certain forms of the present technology, the positioning and stabilising structure 3300 comprises at least one headgear strap acting in addition to the tubes 3350 to position and stabilise the seal-forming structure 3100 in sealing position at the entrance to the patient's airways. As shown in FIG. 6, the patient interface 3000 comprises a strap 3310 forming part of the positioning and stabilising structure 3300. The strap 3310 may be known as a back strap or a rear headgear strap, for example. In other examples of the present technology, one or more further straps may be provided. For example, a patient interface 3000 according to an example of the present technology having a full face or oro-nasal cushion module may have a second, lower, strap configured to overlie the back of the patient's neck.

4.3.5 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

4.3.5.1 Single Use Vent

In one aspect of the technology illustrated in FIGS. 6, 7, 19, and 25-36, the vent 3400 may allow for the washout of exhaled gases through the third opening 3125 of the mouth portion 3105. In addition, the vent 3400 may be positioned away from any air inlet into the plenum 3200. For example, the vent 3400 may be positioned within the third opening 3125 of the mouth portion 3105. Alternatively, the vent 3400 may be positioned in another opening (not shown) in the wall 3211 that may allow for the washout of exhaled gases through the wall 3211. Preferably, the vent 3400 may be configured to be permanently retained within the third opening 3125. However, it is contemplated that the vent 3400 may be removable from the third opening 3125 for cleaning.

The vent 3400 may be an assembly comprising a main body 3405, a cover 3410, and a diffuser 3415 sandwiched between the main body 3405 and the cover 3410.

The main body 3405 may be formed of a rigid material such as plastic and may be the part of the vent 3400 that anchors the vent 3400 to the mouth portion 3105. The main body 3405 may comprise a frame 3420 with features that secure the vent 3400 to the mouth portion 3105 and a receptacle (or retaining portion) 3425 with a receiving space that is bound by the frame 3420.

The frame 3420 may include a first flange 3430 that extends around a perimeter of the frame 3420. A second flange 3435 may be located opposite the first flange 3430. The first flange 3430 and the second flange 3435 may together form a channel 3440. When the vent 3400 is assembled to the mouth portion 3105, at least a portion of the rim of the third opening 3125 may be received within the channel 3440 so that the first flange 3430 and the second flange 3435 may hold the frame 3420 in place within the third opening 3125. In addition, the engagement of the first flange 3430 and the second flange 3435 with the rim of the third opening 3125 may form a seal so that the exhaled gas may flow through the vent 3400 and not around the vent 3400.

In addition, it is contemplated that there may be one or more gaps (or notches) 3445 in the first flange 3430 and/or the second flange 3435. The gaps 3445 may be positioned, sized, and shaped to be complimentary to a tab 3450 extending from the rim of the third opening 3125. The tab 3450 may be received by corresponding one of the gaps 3445 when the frame 3420 is in the correct orientation. The tab 3450 may prevent the frame 3420 from being received within the third opening 3125 when the frame 3420 is in the wrong orientation. It should be understood that the locations of the gaps 3445 and the tabs 3450 may be swapped so that the gaps 3445 are located on the rim of the third opening 3125 and the tabs 3450 are located on the first flange 3430 and/or the second flange 3435. It is further contemplated that the vent 3400 may have other alignment indicators such as printed indicia.

The receptacle 3425 may include a vent wall 3455 with a plurality of vent holes 3460. The receptacle 3425 may also include one or more side walls 3465 that extend from a perimeter of the vent wall 3455 toward the second flange 3435. In addition, a pair of anchor blocks 3470 may be located on opposing lateral sides of the receptacle 3425.

It is contemplated that the vent wall 3455 is contoured so that a side of the vent wall 3455 facing the interior of the receptacle 3425 has a convex shape, and an opposite side of the vent wall 3455 is concave. The plurality of vent holes 3460 may be arranged in any pattern. For example, as shown in FIG. 33, the vent wall 3455 may comprise 16 vent holes 3460 arranged in two rows.

Each vent holes 3460 may be tapered toward the convex side of the vent wall 3455 (i.e., the side facing the receptacle 3425 and facing away from the plenum 3200). In other words, the cross-sectional area of the vent path through each vent hole 3460 may decrease as the vented gas moves further away from the plenum 3200. Accordingly, each vent hole 3460 may have a larger cross-sectional area at the concave side of the vent wall 3455 than the cross-sectional area at the convex side of the vent wall 3455 (i.e., the side facing the plenum 3200). The angle of taper $\theta$ of each vent hole 3460 (the angle formed by the side walls of the vent hole 3460) may be between 10 and 35 degrees. For example, the angle of taper $\theta$ may be 30.4 degrees or 14.0 degrees. In addition, the diameter D of each vent hole 3460 at the smaller end may be between 0.5 and 2 mm. For example, the diameter D may be 0.89, 0.98, 1.17 mm, or 1.01 mm. The thickness of the vent wall 3455 (and the height of each vent hole 3460) H may be between 1.5 and 2.5 mm. For example, the thickness H may be 2.0 mm.

As illustrated in FIG. 28, each vent hole may flare outward at the larger side (i.e., side adjacent the plenum 3200). The flared portions of the vent holes 3460 may have a radius of curvature R between 0.2 mm and 0.4 mm. For example, the radius of curvature may be 0.25 mm or 0.3 mm.

The cover 3410 may be secured to the main body 3405 at the anchor blocks 3470. The cover 3410 may be secured by way of a friction fit, a snap fit, an adhesive, a mechanical fastener, or any other fastening method.

Each anchor block 3470 may be located at a lateral side of the main body 3405 and may include an interfacing surface 3475 that is inside the receptacle 3425 and is offset from the vent wall 3455. The interfacing surface 3475 may have an anchor hole (socket) 3480 that receives a corresponding anchor peg (or anchor post) 3485 that extends from cover 3410. The anchor hole 3480 may be keyed with the anchor peg 3485. In other words, the anchor hole 3480 may be shaped complimentarily to the shape of the anchor peg 3485. It is contemplated that the anchor hole 3480 may extend into the anchor block 3470 as far as the channel 3440 (FIG. 30). It is further contemplated that the anchor hole 3480 may extend beyond the channel 3440 and may narrow toward the bottom of the anchor hole 3480 (FIG. 36). Extending and narrowing the anchor hole 3480 may allow for more surface contact and may allow the anchor pegs 3485 of the cover 3410 to fit more tightly and become more edged in the anchor holes 3480, thereby increasing the retaining force acting on the anchor pegs 3485. In addition, each anchor hole 3480 may have a different shape and/or size so that the anchor pegs 3485 cannot be inserted into the anchor holes 3480 unless the cover 3410 is in the correct orientation.

As shown in FIGS. 27 and 33, the vent wall 3455 may include a first support strip 3490 across a lateral length of the vent wall 3455. The first support strip 3490 may extend from one of the anchor blocks 3470 to the other anchor block 3470. A pair of second support strips 3495 may position on opposite sides of the first support strip 3490 and may extend in a direction perpendicular to the first support strip 3490.

The diffuser 3415 may rest on the first support strip 3490 and the second support strips 3495 when the diffuser 3415 is received within the receptacle 3425. Thus, the diffuser 3415 may be spaced away from the vent wall 3455 so that a space is maintained between the diffuser 3415 and the vent wall 3455. The first support strip 3490 and the pair of support strips 3495 may also have the effect of dividing the air flow as the vented gas exits the vent holes 3460.

Because exhalation gas has a level of humidity, the diffuser 3415 is prone to getting wet when exhaled gas flows through the diffuser 3415. Spacing the diffuser away from the vent wall 3455 may allow the diffuser 3415 to dry between therapy sessions, which in turn may prevent the growth of mold, bacteria, or other undesired contaminants.

It is contemplated that the diffuser 3415 may be a continuous body made of any porous material such as open cell foam, cotton, or any other fibrous material. It is also contemplated that the diffuser 3415 may be hydrophobic or hydrophilic.

As illustrated in FIGS. 25, 27, and 32, the anchor blocks 3470 extend all the way or almost all of the way to the second flange 3435. It is contemplated that the depth of the anchor blocks 3470 may be equal to or larger than the thickness of the diffuser 3415. This way, attaching the cover 3410 to the main body 3405 will not compress the diffuser 3415 or will not compress the diffuser beyond a desired and/or a predetermined threshold so that the air paths within the diffuser 3415 are not restricted beyond a desired or predetermined limit. In addition, the lateral sides of the diffuser 3415 may be shaped complimentarily to the shape of the anchor blocks 3470 so that the lateral sides of the diffuser 3415 may abut and/or conform to the anchor blocks 3470 without being compressed more than a desired and/or predetermined amount. This way, the anchor blocks 3470 may prevent lateral movement of diffuser 3415. Accordingly, the size of the diffuser 3415 may be maximized and the diffuser 3415 may be fixed in place without compressing the diffuser 3415 or without compressing the diffuser 3415 by more than a desired and/or predetermined amount.

After the diffuser 3415 has been received in the receptacle 3425, the cover may be positioned on the main body 3405 and the anchor holes 3480 may receive the anchor pegs 3485 to secure the cover 3410 to the main body 3405, thereby locking the diffuser 3415 in place. It should be understood that the cover 3410 may be anchored to the main body 3405 at the lateral sides of the main body 3405 so that the diffuser 3415 is positioned between the anchor points (or the attachment mechanisms) that secure the cover 3410 to the main body 2405.

The cover 3410 may have a solid surface with no holes and may be smaller than the receptacle 3425. Accordingly, when the cover 3410 is secured the main body 3405, a gap 3497 is formed between the perimeter of the receptacle 3425 and the perimeter of the cover 3410. The underside of the cover 3410 may also have a plurality of projections 3499. One projection 3499 may extend lengthwise across a central portion of the cover 3410. A pair of projections 3499 may extend widthwise across lateral sides of the cover 3410 (or perpendicular to the lengthwise projection 3499). It is contemplated that the lengthwise projection 3499 may extend from one widthwise projection 3499 to another widthwise projection 3499. In addition, the lengthwise projection 3499 may extend across a center line of the cover 3410. The projections 3499 may have the effect of compressing the diffuser 3415 to a predetermined extent, thereby compressing the air paths through the diffuser 3415. The projections 3499 may also serve as a flow separator to the air flowing through the diffuser 3415. Thus, the flow path of exhaled gas from the plenum 3200 may flow through the vent holes 3460, through the diffuser 3415, and around the perimeter of the cover 3410. It is contemplated that the projections 3499 may have any cross-sectional shape. For example, a cross-sectional shape of the projections 3499 may be triangular. It is also contemplated that different projections 3499 may have different cross-sectional shapes or the same cross-sectional shape.

4.3.5.2 Multiple Use Vent

In another aspect of the technology illustrated in FIGS. 37-40, the vent 3400 may allow for the washout of exhaled gases through the third opening 3125 of the mouth portion 3105. In addition, the vent 3400 may be positioned away from any air inlet into the plenum 3200. For example, the vent 3400 may be positioned within the third opening 3125 of the mouth portion 3105. Alternatively, the vent 3400 may be positioned in another opening (not shown) in the wall 3211 that may allow for the washout of exhaled gases through the wall 3211. Preferably, in this configuration, the vent 3400 may be configured to be removable from the third opening 3125 for cleaning. However, it is contemplated that the vent 3400 may be permanently retained within the third opening 3125.

The vent 3400 may be a unitary body with a main body 3405 integrally formed with a cover 3410. In this configuration, the diffuser may be omitted. The vent 3400 may be formed of a rigid material such as plastic. The main body 3405 may be the part of the vent 3400 that anchors the vent 3400 to the mouth portion 3105.

The main body 3405 may include a first flange 3430 that extends around a perimeter of the main body 3405. A second flange 3435 may be located opposite the first flange 3430. The first flange 3430 and the second flange 3435 may together form a channel 3440. When the vent 3400 is assembled to the mouth portion 3105, at least a portion of the rim of the third opening 3125 may be received within the channel 3440 so that the first flange 3430 and the second flange 3435 may hold the main body 3405 in place within the third opening 3125. In addition, the engagement of the first flange 3430 and the second flange 3435 with the rim of the third opening 3125 may form a seal so that the exhaled gas may flow through the vent 3400 and not around the vent 3400.

In addition, it is contemplated that there may be one or more gaps (or notches) 3445 in the first flange 3430 and/or the second flange 3435. The gaps 3445 may be positioned, sized, and shaped to be complimentary to a tab 3450 extending from the rim of the third opening 3125. The tab 3450 may be received by corresponding one of the gaps 3445 when the frame 3420 is in the correct orientation. The tab 3450 may prevent the frame 3420 from being received within the third opening 3125 when the frame 3420 is in the wrong orientation. It should be understood that the locations of the gaps 3445 and the tabs 3450 may be swapped so that the gaps 3445 are located on the rim of the third opening 3125 and the tabs 3450 are located on the first flange 3430 and/or the second flange 3435. It is further contemplated that the vent 3400 may have other alignment indicators such as printed indicia.

The cover 3410 may include a vent wall 3455 with a plurality of vent holes 3460. In addition the vent 3400 may include one or more side walls 3465 that extend from a perimeter of the vent wall 3455 toward the first flange 3430. Accordingly, the cover 3410 may be spaced away from the third opening 3125 when the vent 3400 is secured to the mouth portion 3105.

It is contemplated that the vent wall 3455 may be contoured so that a side of the vent wall 3455 facing the interior of the vent 3400 has a concave shape, and an opposite side of the vent wall 3455 is convex. The plurality of vent holes 3460 may be arranged in any pattern. For example, as shown in FIG. 37, the vent wall 3455 may comprise 20 vent holes 3460 with 16 vent holes 3460 arranged in two rows and two additional rows of vent holes 3460 (two vent holes 3460 each) are positioned on opposite sides of the two rows of 16 vent holes 3460.

Each vent holes 3460 may be tapered toward the convex side of the vent wall 3455 (i.e., the side facing away from the third opening 3125). In other words, the cross-sectional area of the vent path through each vent hole 3460 may decrease as the vented gas moves further away from the plenum 3200. Accordingly, each vent hole 3460 may have a larger cross-sectional area at the concave side of the vent wall 3455 than the cross-sectional area at the convex side of the vent wall 3455 (i.e., the side facing the plenum 3200). The angle of taper θ of each vent hole 3460 (the angle formed by the side walls of the vent hole 3460) may be between 10 and 35 degrees. For example, the angle of taper θ may be 30.4 degrees or 14.0 degrees. In addition, the diameter D of each vent hole 3460 at the smaller end may be between 0.5 and 2 mm. For example, the diameter D may be 0.89, 0.98, 1.17 mm, or 1.01 mm. The thickness of the vent wall 3455 (and the height of each vent hole 3460) H may be between 1.5 and 2.5 mm. For example, the thickness H may be 2.0 mm.

As illustrated in FIG. 38, each vent hole may flare outward at the larger side (i.e., side adjacent the plenum 3200). The flared portions of the vent holes 3460 may have a radius of curvature R between 0.2 mm and 0.4 mm. For example, the radius of curvature may be 0.25 mm or 0.3 mm.

As discussed above, the cover 3410 may be integrally formed with the main body 3405. In one configuration, the cover 3410 may have a smooth continuous surface. However, in another configuration, the outer surface of the cover 3410 may have a channel 3498 that completely encircles the array of vent holes 3460. The channel 3498 may help reduce sink marks that may form during the manufacturing process.

4.3.6 Decoupling Structure(s)

In one form the patient interface 3000 includes at least one decoupling structure, for example, a swivel or a ball and socket.

4.3.7 Connection Port

Connection port 3600 allows for connection to the air circuit 4170.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

4.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH2O, or at least 10 cmH2O, or at least 20 cmH2O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

4.4.1 RPT Device Mechanical & Pneumatic Components

An RPT device may comprise one or more of the following components in an integral unit. In an alternative form, one or more of the following components may be located as respective separate units.

4.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000 or 3800.

4.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000 or 3800.

4.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH2O to about 20 cmH2O, or in other forms up to about 30 cmH2O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

4.4.1.4 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

4.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

In other forms of the present technology, some portion or all of the algorithms 4300 may be implemented by a controller of an external device such as the local external device 4288 or the remote external device 4286. In such forms, data representing the input signals and/or intermediate algorithm outputs necessary for the portion of the algorithms 4300 to be executed at the external device may be communicated to the external device via the local external communication network 4284 or the remote external communication network 4282. In such forms, the portion of the algorithms 4300 to be executed at the external device may be expressed as computer programs, such as with processor control instructions to be executed by one or more processor(s), stored in a non-transitory computer readable storage medium accessible to the controller of the external device. Such programs configure the controller of the external device to execute the portion of the algorithms 4300.

In such forms, the therapy parameters generated by the external device via the therapy engine module 4320 (if such forms part of the portion of the algorithms 4300 executed by the external device) may be communicated to the central controller 4230 to be passed to the therapy control module 4330.

4.5 Air Circuit

An air circuit 4170 in accordance with an aspect of the present technology is a conduit or a tube constructed and arranged to allow, in use, a flow of air to travel between two components such as RPT device 4000 and the patient interface 3000 or 3800.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

4.6 Humidifier 4.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

4.6.2 Humidifier Components 4.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

4.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

4.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

4.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

4.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

4.7 Glossary

For the purposes of the present technology disclosure, in certain forms of the present technology, one or more of the following definitions may apply. In other forms of the present technology, alternative definitions may apply.

4.7.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation.

In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal (1 hectopascal=100 Pa=100 $N/m^2$=1 millibar~0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

4.7.1.1 Materials & their Properties (Durometer Hardness (Indentation Hardness): A material property measured by indentation of an indentor (e.g. As measured in accordance with ASTM D2240).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45.

Polycarbonate: a thermoplastic polymer of Bisphenol-A Carbonate.

4.7.1.2 Mechanics

Axes:
a. Neutral axis: An axis in the cross-section of a beam or plate along which there are no longitudinal stresses or strains.
b. Longitudinal axis
c. Circumferential axis
d. Radial axis Deformation: The process where the original geometry of a member changes when subjected to forces, e.g. a force in a direction with respect to an axis. The process may include stretching or compressing, bending and, twisting.

Stiffness: The ability of a structure or component to resist deformation in response to an applied load. A structure or component may have an axial stiffness, a bending stiffness, and a torsional stiffness. A structure or component is said to be stiff when it does not deform easily when subject to mechanical forces. Stiffness of a structure or component is related to its material properties and its shape. The inverse of stiffness is flexibility.

Elasticity: The ability of a material to return to its original geometry after deformation.

Viscous: The ability of a material to resist flow.

Visco-elasticity: The ability of a material to display both elastic and viscous behaviour in deformation.

Yield: The situation when a material can no longer return back to its original geometry after deformation.

4.7.1.3 Structural Elements

Thin structures:
a. Beams,
b. Membranes, Plates & Shells

Thick structures: Solids

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Membrane: Membrane will be taken to mean a typically thin element that has, preferably, substantially no resistance to bending, but has resistance to being stretched.

Load transfer member: A structural member which transfers load from one location to another member.

Load support member: A structural member which transfers load from one location to a non-structural item, such as the face.

Tension member: A structural element that resists tensional forces

Tie (noun): A structure designed to resist tension.

Compression member: A structural element that resists compression forces.

Strut: A strut will be taken to be a structural component designed to increase the compression resistance of another component in at least one direction. Stiffener Stiffener: A stiffener will be taken to mean a structural component designed to increase the bending resistance of another component in at least one direction.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

4.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

Inhalation Time (Ti): The duration of the inspiratory portion of the respiratory flow rate waveform.

Exhalation Time (Te): The duration of the expiratory portion of the respiratory flow rate waveform.

Total Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired interface pressure which the ventilator will attempt to achieve at a given time.

End expiratory pressure (EEP): Desired interface pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired interface pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts, pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator, or other respiratory therapy device such as an RPT device or portable oxygen concentrator, delivers a volume of breathable gas to a spontaneously breathing patient, it is said to be triggered to do so. Triggering usually takes place at or near the initiation of the respiratory portion of the breathing cycle by the patient's efforts.

4.7.4 Anatomy
4.7.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 4.7.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.7.5 Patient Interface

Anti-asphyxia valve (AAV): The component or sub-assembly of a mask system that, by opening to atmosphere in a failsafe manner, reduces the risk of excessive CO2 rebreathing by a patient.

Functional dead space: (description to be inserted here)

Headgear: Headgear will be taken to mean a form of positioning and stabilizing structure designed to hold a device, e.g. a mask, on a head.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.7.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill) See FIG. 3E (relatively small negative curvature compared to FIG. 3F) and FIG. 3F (relatively large negative curvature compared to FIG. 3E). Such curves are often referred to as convex.

4.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill)

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.7.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 4.9 REFERENCE SIGNS LIST | |
|---|---|
| patient | 1000 |
| bed partner | 1100 |
| main body | 2405 |
| patient interface | 3000 |
| main body | 3010 |
| seal - forming structure | 3100 |
| mouth portion | 3105 |
| oral portion | 3105 |
| nasal portion | 3110 |
| first opening | 3115 |
| second opening | 3120 |
| third opening | 3125 |
| receptacle | 3130 |
| base | 3135 |
| one side wall | 3140 |
| outer rim | 3145 |
| pace | 3150 |
| fourth opening | 3155 |
| nasal base | 3160 |
| nasal pillow | 3165 |
| nasal plenum | 3170 |
| inlet opening | 3175 |
| flange | 3180 |
| side wall | 3182 |
| first side | 3185 |
| second side | 3190 |
| line | 3195 |
| flange | 3197 |
| plenum | 3200 |
| chord | 3210 |
| wall | 3211 |
| superior point | 3220 |
| upper headgear connectors | 3221 |
| inferior point | 3230 |
| lower headgear connectors | 3231 |
| structure | 3300 |
| strap | 3310 |
| tube | 3350 |
| non - extendable tube section | 3363 |
| vent | 3400 |
| main body | 3405 |
| cover | 3410 |
| diffuser | 3415 |

4.9 REFERENCE SIGNS LIST

| | |
|---|---|
| frame | 3420 |
| receptacle | 3425 |
| first flange | 3430 |
| second flange | 3435 |
| channel | 3440 |
| gaps | 3445 |
| tab | 3450 |
| vent wall | 3455 |
| vent hole | 3460 |
| side walls | 3465 |
| anchor block | 3470 |
| surface | 3475 |
| anchor hole | 3480 |
| anchor peg | 3485 |
| first support strip | 3490 |
| second support strips | 3495 |
| gap | 3497 |
| channel | 3498 |
| Projection | 3499 |
| connection port | 3600 |
| elbow | 3610 |
| forehead support | 3700 |
| ISO | 3744 |
| patient interface | 3800 |
| RPT device | 4000 |
| external housing | 4010 |
| upper portion | 4012 |
| portion | 4014 |
| panel s | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| electrical components | 4200 |
| PCBA | 4202 |
| electrical power supply | 4210 |
| input devices | 4220 |
| central controller | 4230 |
| therapy device controller | 4240 |
| protection circuits | 4250 |
| memory | 4260 |
| transducers | 4270 |
| pressure sensors | 4272 |
| flow rate sensors | 4274 |
| data communication interface | 4280 |
| remote external communication network | 4282 |
| local external communication network | 4284 |
| remote external device | 4286 |
| local external device | 4288 |
| output devices | 4290 |
| algorithms | 4300 |
| therapy engine module | 4320 |
| therapy control module | 4330 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |
| clip | 6000 |
| lumen | 6005 |
| central longitudinal axis | 6007 |
| middle flange | 6010 |
| first end flange | 6015 |
| flange | 6020 |
| first channel | 6025 |
| second channel | 6030 |
| first side | 6035 |
| second side | 6040 |
| side wall | 6047 |
| channel side | 6050 |
| wing | 6060 |
| nasal pillow facing side | 6065 |
| base | 6070 |
| end | 6075 |
| nasal module magnet | 7000 |
| receptacle magnet | 7005 |
| lip seal | 7010 |
| core | 7015 |
| core | 7016 |
| silicone rubber covering | 7020 |
| indicia | 8000 |
| indicia | 8005 |
| indentation | 8010 |
| tab | 8015 |
| nasal prongs | 3810a |
| nasal prongs | 3810b |
| lumens | 3820a |
| lumens | 3820b |

The invention claimed is:

1. A patient interface comprising:
a mouth plenum pressurisable to a therapeutic pressure of at least 6 cmH2O above ambient air pressure, said mouth plenum including a plenum chamber inlet port sized and structured to receive a flow of air at the therapeutic pressure for breathing by a patient,
a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the mouth plenum throughout the patient's respiratory cycle in use, the seal-forming structure comprising:
a mouth portion that forms at least part of the mouth plenum and is configured to seal around the patient's mouth;
a nasal portion that is configured to seal with the patient's nares, the nasal portion comprising a nasal plenum and an inlet opening positioned to receive pressurized gas from the mouth plenum; and
a clip configured to connect the mouth plenum to the nasal plenum and act as a conduit for the flow of the pressurized gas from the mouth plenum to the nasal plenum, the clip comprising:
a main body that forms an airflow path between the mouth plenum and the nasal plenum, the main body comprising a mouth portion end configured to engage the mouth portion and a nasal portion end configured to engage the nasal portion;
a nasal end flange that extends radially from the airflow path at the nasal portion end of the main body;
a middle flange that extends radially from the airflow path and forms a nasal end channel together with the nasal end flange that is configured to receive a rim of the inlet opening of the nasal plenum; and a pair of wings protruding from the nasal end flange into an interior of the nasal plenum so that the wings engage an interior surface of the nasal plenum, a base of each wing being positioned on opposing lateral sides of the clip;

a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breathe from ambient through their mouth in the absence of a flow of pressurised air through the plenum chamber inlet port.

2. The patient interface of claim 1, wherein the wings are separate and distinct from each other.

3. The patient interface of claim 1, wherein a height of each wing is a distance each wing projects from the nasal portion end of the clip, and the maximum height of each wing is at the laterally furthest point on the wing.

4. The patient interface of claim 3, wherein the height of each wing varies gradually to form a smooth curve, and wherein the height of each wing decreases to a value of zero toward a central region of the nasal portion end of the clip.

5. The patient interface of claim 1, wherein the mouth plenum comprises an outlet opening, and wherein the clip comprises a mouth end flange that together forms a mouth end channel that receives a rim of the outlet opening of the mouth plenum.

6. The patient interface of claim 5, wherein the mouth end flange is configured to be inserted into the mouth plenum.

7. The patient interface of claim 6, wherein a rim of the outlet opening of the mouth plenum comprises a tab and there is a notch in the mouth end flange of the clip, and wherein the notch is positioned to receive the tab when the nasal portion is connected to the mouth portion in the correct orientation.

8. The patient interface of claim 7, wherein the tab is configured to prevent the nasal portion from being secured to the mouth portion in a wrong orientation.

9. The patient interface of claim 1, wherein an outer surface of the mouth portion comprises a first printed indicia, an outer surface of the nasal portion comprises a second printed indicia that lines up with the first printed indicia when the nasal portion is connected to the mouth portion in the correct orientation.

10. The patient interface of claim 1, wherein the nasal portion comprises a flexible base and a pair of nasal pillows attached to the flexible base, the nasal pillows being configured to seal with an interior of the patient's nostrils.

11. The patient interface of claim 1, wherein the mouth portion comprises a flange having an inside surface and an outside surface, and wherein the flange comprises a target seal-forming region located on an outside surface thereof.

12. The patient interface of claim 11, wherein the outside surface comprises a lip region constructed to have a lip saddle-shaped region.

13. The patient interface of claim 12, wherein at a point on the outside surface of the mouth portion where the mid-contact plane touches the target seal-forming region, the curvature of the lip saddle-shaped region in the inferior-superior direction has a negative sign and a magnitude that is larger than a magnitude of the curvature of the lip saddle-shaped region in the left-right direction.

14. The patient interface of claim 11, wherein the outside surface comprises a left corner region and a right corner region.

15. The patient interface of claim 14, wherein the outside surface is constructed to have a first convex dome-shaped region in said left corner region.

16. The patient interface of claim 14, wherein the outside surface is constructed to have a second convex dome-shaped region in said right corner region.

17. The patient interface of claim 11, wherein the outside surface of said flange has an inner edge, said hole is bounded by said inner edge, and said inner edge includes an inner edge lip region.

18. The patient interface of claim 17, wherein the inner edge of said flange is constructed so that a space curve on the outside surface of the flange at said inner edge in said left corner region has a left-hand positive torsion.

19. The patient interface of claim 17, wherein the inner edge of said flange is constructed so that a space curve on the outside surface of the flange at said inner edge in said right corner region has a right-hand positive torsion.

20. The patient interface of claim 1, wherein the mouth plenum is partly formed by a shell, which has a shell inside surface and shell outside surface, and wherein the shell inside surface is arranged to be at said therapeutic pressure in use, and said shell outside surface is arranged to be at ambient pressure in use.

21. The patient interface of claim 20, wherein the shell is structured to be rigid when subject to an internal pressure of 30 cmH2O above ambient pressure or less.

22. The patient interface of claim 20, wherein the shell is constructed from a hard plastic material.

23. The patient interface of claim 20, wherein the shell is constructed from a transparent material.

24. The patient interface of claim 20, wherein the shell inside surface is constructed to include a concave dome-shaped region.

25. The patient interface of claim 1, wherein the positioning and stabilising structure includes a second tie, the second tie being constructed and arranged so that at least a portion of a superior edge thereof passes inferior to an otobasion inferior of the patient's head and to overlay or lie inferior to the occipital bone of the patient's head.

26. The patient interface of claim 1, wherein the positioning and stabilising structure includes a low profile side portion configured to be positioned under the patient's head while the patient is lying in a side sleeping position.

27. The patient interface of claim 1, wherein the mouth plenum is constructed from a transparent material.

28. The patient interface of claim 1, configured so that no part of the patient interface enters the patient's mouth in use.

29. The patient interface of claim 1, constructed and arranged so that the mouth plenum does not cover the patient's eyes in use.

* * * * *